(12) United States Patent
Kataoka et al.

(10) Patent No.: US 7,547,531 B2
(45) Date of Patent: Jun. 16, 2009

(54) L-AMINO ACID PRODUCING MICROORGANISM WHICH HAS BEEN MODIFIED TO INACTIVE THE FIMH GENE, AND A METHOD FOR PRODUCING I-AMINO ACID

(75) Inventors: Saori Kataoka, Kawasaki (JP); Yuuta Nakai, Kawasaki (JP); Takuji Ueda, Kawasaki (JP); Yuji Joe, Kawasaki (JP); Hisao Ito, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 370 days.

(21) Appl. No.: 11/275,562

(22) Filed: Jan. 17, 2006

(65) Prior Publication Data
US 2006/0160191 A1    Jul. 20, 2006

Related U.S. Application Data

(60) Provisional application No. 60/644,040, filed on Jan. 18, 2005, provisional application No. 60/673,338, filed on Apr. 21, 2005.

(30) Foreign Application Priority Data

Jan. 18, 2005  (JP) .............................. 2005-009826
Apr. 18, 2005  (JP) .............................. 2005-120222

(51) Int. Cl.
*C12P 13/04* (2006.01)
*C12P 13/14* (2006.01)
*C12P 13/08* (2006.01)
*C12N 15/00* (2006.01)
*C12N 1/21* (2006.01)
*C12P 21/00* (2006.01)
*C07K 14/00* (2006.01)
*C07H 21/00* (2006.01)

(52) U.S. Cl. ...................... 435/106; 435/110; 435/115; 435/320.1; 435/69.1; 435/252.33; 536/23.1; 530/350

(58) Field of Classification Search .............. 435/320.1, 435/69.1, 325, 252.3, 106, 110, 115; 530/350; 536/23.1
See application file for complete search history.

(56) References Cited

U.S. PATENT DOCUMENTS

| | | | |
|---|---|---|---|
| 6,720,139 B1 * | 4/2004 | Zyskind et al. ................. | 435/6 |
| 6,737,063 B2 * | 5/2004 | Langermann et al. .... | 424/190.1 |
| 2002/0160461 A1 | 10/2002 | Nakai et al. | |
| 2003/0077764 A1 | 4/2003 | Tsujimoto et al. | |
| 2004/0121428 A1 | 6/2004 | Sugimoto et al. | |
| 2005/0170474 A1 | 8/2005 | Yamamoto et al. | |
| 2005/0196846 A1 | 9/2005 | Hara et al. | |
| 2005/0260720 A1 | 11/2005 | Ito et al. | |
| 2005/0277179 A1 | 12/2005 | Takai et al. | |
| 2006/0019355 A1 | 1/2006 | Ueda et al. | |

OTHER PUBLICATIONS

GeneBank, Accession No. NP_418740, Dec. 20, 2007.*
Lewin B., Genes V. Oxford University Press Inc., New York, 1994, p. 1236.*
Schembri et al., FEMS Microbiology Letters 137:257-263, 1996.*

* cited by examiner

*Primary Examiner*—Delia M Ramirez
(74) *Attorney, Agent, or Firm*—Shelly Guest Cermak; Cermak Keneally Vaidya & Nakajima LLP

(57) ABSTRACT

An L-amino acid producing bacterium of the Enterobacteriaceae family is described, wherein the bacterium has been modified so as to not produce type I fimbrial adhesin protein is cultured in a medium to produce and excrete said L-amino acid in the medium, and collecting said L-amino acid from the medium.

2 Claims, 2 Drawing Sheets

SEQUENCE LISTING

```
<160> NUMBER OF SEQ ID NOS: 61

<210> SEQ ID NO 1
<211> LENGTH: 903
<212> TYPE: DNA
<213> ORGANISM: Escherichia coli
<220> FEATURE:
<221> NAME/KEY: CDS
<222> LOCATION: (1)..(903)
<223> OTHER INFORMATION: fimH

<400> SEQUENCE: 1 atg aaa cga gtt att acc ctg ttt gct gta ctg ctg atg ggc tgg tcg    48
Met Lys Arg Val Ile Thr Leu Phe Ala Val Leu Leu Met Gly Trp Ser
1               5                   10                  15 gta aat gcc tgg tca ttc gcc tgt aaa acc gcc aat ggt acc gct atc    96
Val Asn Ala Trp Ser Phe Ala Cys Lys Thr Ala Asn Gly Thr Ala Ile
                20                  25                  30 cct att ggc ggt ggc agc gcc aat gtt tat gta aac ctt gcg ccc gtc   144
Pro Ile Gly Gly Gly Ser Ala Asn Val Tyr Val Asn Leu Ala Pro Val
            35                  40                  45 gtg aat gtg ggg caa aac ctg gtc gtg gat ctt tcg acg caa atc ttt   192
Val Asn Val Gly Gln Asn Leu Val Val Asp Leu Ser Thr Gln Ile Phe
        50                  55                  60 tgc cat aac gat tat ccg gaa acc att aca gac tat gtc aca ctg caa   240
Cys His Asn Asp Tyr Pro Glu Thr Ile Thr Asp Tyr Val Thr Leu Gln
65                  70                  75                  80 cga ggc tcg gct tat ggc ggc gtg tta tct aat ttt tcc ggg acc gta   288
Arg Gly Ser Ala Tyr Gly Gly Val Leu Ser Asn Phe Ser Gly Thr Val
                85                  90                  95 aaa tat agt ggc agt agc tat cca ttt cct acc acc agc gaa acg ccg   336
Lys Tyr Ser Gly Ser Ser Tyr Pro Phe Pro Thr Thr Ser Glu Thr Pro
            100                 105                 110
```

| | | | | | | | | | | | | | | | |
|---|---|---|---|---|---|---|---|---|---|---|---|---|---|---|---|
| cgc | gtt | gtt | tat | aat | tcg | aga | acg | gat | aag | ccg | tgg | ccg | gtg | gcg | ctt | 384
| Arg | Val | Val | Tyr | Asn | Ser | Arg | Thr | Asp | Lys | Pro | Trp | Pro | Val | Ala | Leu |
| | | | 115 | | | | 120 | | | | 125 | | | | |

```
cgc gtt gtt tat aat tcg aga acg gat aag ccg tgg ccg gtg gcg ctt      384
Arg Val Val Tyr Asn Ser Arg Thr Asp Lys Pro Trp Pro Val Ala Leu
            115                 120                 125 tat ttg acg cct gtg agc agt gcg ggc ggg gtg gcg att aaa gct ggc      432
Tyr Leu Thr Pro Val Ser Ser Ala Gly Gly Val Ala Ile Lys Ala Gly
130                 135                 140 tca tta att gcc gtg ctt att ttg cga cag acc aac aac tat aac agc      480
Ser Leu Ile Ala Val Leu Ile Leu Arg Gln Thr Asn Asn Tyr Asn Ser
145                 150                 155                 160 gat gat ttc cag ttt gtg tgg aat att tac gcc aat aat gat gtg gtg      528
Asp Asp Phe Gln Phe Val Trp Asn Ile Tyr Ala Asn Asn Asp Val Val
            165                 170                 175 gtg cct act ggc ggc tgc gat gtt tct gct cgt gat gtc acc gtt act      576
Val Pro Thr Gly Gly Cys Asp Val Ser Ala Arg Asp Val Thr Val Thr
                180                 185                 190 ctg ccg gac tac cct ggt tca gtg cca att cct ctt acc gtt tat tgt      624
Leu Pro Asp Tyr Pro Gly Ser Val Pro Ile Pro Leu Thr Val Tyr Cys
                    195                 200                 205 gcg aaa agc caa aac ctg ggg tat tac ctc tcc ggc aca acc gca gat      672
Ala Lys Ser Gln Asn Leu Gly Tyr Tyr Leu Ser Gly Thr Thr Ala Asp
        210                 215                 220 gcg ggc aac tcg att ttc acc aat acc gcg tcg ttt tca cct gca cag      720
Ala Gly Asn Ser Ile Phe Thr Asn Thr Ala Ser Phe Ser Pro Ala Gln
225                 230                 235                 240 ggc gtc ggc gta cag ttg acg cgc aac ggt acg att att cca gcg aat      768
Gly Val Gly Val Gln Leu Thr Arg Asn Gly Thr Ile Ile Pro Ala Asn
                    245                 250                 255 aac acg gta tcg tta gga gca gta ggg act tcg gcg gtg agt ctg gga      816
Asn Thr Val Ser Leu Gly Ala Val Gly Thr Ser Ala Val Ser Leu Gly
        260                 265                 270 tta acg gca aat tat gca cgt acc gga ggg cag gtg act gca ggg aat      864
Leu Thr Ala Asn Tyr Ala Arg Thr Gly Gly Gln Val Thr Ala Gly Asn
                275                 280                 285 gtg caa tcg att att ggc gtg act ttt gtt tat caa taa                  903
Val Gln Ser Ile Ile Gly Val Thr Phe Val Tyr Gln
                    290                 295                 300

<210> SEQ ID NO 2
<211> LENGTH: 300
<212> TYPE: PRT
<213> ORGANISM: Escherichia coli

<400> SEQUENCE: 2

Met Lys Arg Val Ile Thr Leu Phe Ala Val Leu Leu Met Gly Trp Ser
1               5                   10                  15

Val Asn Ala Trp Ser Phe Ala Cys Lys Thr Ala Asn Gly Thr Ala Ile
            20                  25                  30

Pro Ile Gly Gly Gly Ser Ala Asn Val Tyr Val Asn Leu Ala Pro Val
        35                  40                  45

Val Asn Val Gly Gln Asn Leu Val Val Asp Leu Ser Thr Gln Ile Phe
    50                  55                  60

Cys His Asn Asp Tyr Pro Glu Thr Ile Thr Asp Tyr Val Thr Leu Gln
65                  70                  75                  80

Arg Gly Ser Ala Tyr Gly Gly Val Leu Ser Asn Phe Ser Gly Thr Val
                85                  90                  95

Lys Tyr Ser Gly Ser Ser Tyr Pro Phe Pro Thr Thr Ser Glu Thr Pro
            100                 105                 110

Arg Val Val Tyr Asn Ser Arg Thr Asp Lys Pro Trp Pro Val Ala Leu
        115                 120                 125
```

```
Tyr Leu Thr Pro Val Ser Ser Ala Gly Gly Val Ala Ile Lys Ala Gly
    130                 135                 140

Ser Leu Ile Ala Val Leu Ile Leu Arg Gln Thr Asn Asn Tyr Asn Ser
145                 150                 155                 160

Asp Asp Phe Gln Phe Val Trp Asn Ile Tyr Ala Asn Asn Asp Val Val
                165                 170                 175

Val Pro Thr Gly Gly Cys Asp Val Ser Ala Arg Asp Val Thr Val Thr
                180                 185                 190

Leu Pro Asp Tyr Pro Gly Ser Val Pro Ile Pro Leu Thr Val Tyr Cys
            195                 200                 205

Ala Lys Ser Gln Asn Leu Gly Tyr Tyr Leu Ser Gly Thr Thr Ala Asp
    210                 215                 220

Ala Gly Asn Ser Ile Phe Thr Asn Thr Ala Ser Phe Ser Pro Ala Gln
225                 230                 235                 240

Gly Val Gly Val Gln Leu Thr Arg Asn Gly Thr Ile Ile Pro Ala Asn
                245                 250                 255

Asn Thr Val Ser Leu Gly Ala Val Gly Thr Ser Ala Val Ser Leu Gly
                260                 265                 270

Leu Thr Ala Asn Tyr Ala Arg Thr Gly Gly Gln Val Thr Ala Gly Asn
            275                 280                 285

Val Gln Ser Ile Ile Gly Val Thr Phe Val Tyr Gln
    290                 295                 300

<210> SEQ ID NO 3
<211> LENGTH: 54
<212> TYPE: DNA
<213> ORGANISM: Artificial Sequence
<220> FEATURE:
<223> OTHER INFORMATION: primer

<400> SEQUENCE: 3
tttgctttct tctttcaata ccttaacggt atagcgtgaa gcctgctttt ttat         54

<210> SEQ ID NO 4
<211> LENGTH: 54
<212> TYPE: DNA
<213> ORGANISM: Artificial Sequence
<220> FEATURE:
<223> OTHER INFORMATION: primer

<400> SEQUENCE: 4
agatatgact atgaacgtta ttgcaatatt gaatcacgct caagttagta taaa         54

<210> SEQ ID NO 5
<211> LENGTH: 54
<212> TYPE: DNA
<213> ORGANISM: Artificial Sequence
<220> FEATURE:
<223> OTHER INFORMATION: primer

<400> SEQUENCE: 5
ggaggaacac atgaacatca ttgccattat gggacctgaa gcctgctttt ttat         54

<210> SEQ ID NO 6
<211> LENGTH: 53
<212> TYPE: DNA
<213> ORGANISM: Artificial Sequence
<220> FEATURE:
<223> OTHER INFORMATION: primer

<400> SEQUENCE: 6
```
cgccattttt aggactcgta cgcggtaaac gccgtccgtc aagttagtat aaa        53

<210> SEQ ID NO 7
<211> LENGTH: 54
<212> TYPE: DNA
<213> ORGANISM: Artificial Sequence
<220> FEATURE:
<223> OTHER INFORMATION: primer

<400> SEQUENCE: 7
gatgattgta atgaaacgag ttattaccct gtttgctgaa gcctgctttt ttat       54

<210> SEQ ID NO 8
<211> LENGTH: 53
<212> TYPE: DNA
<213> ORGANISM: Artificial Sequence
<220> FEATURE:
<223> OTHER INFORMATION: primer

<400> SEQUENCE: 8
ataaacaaaa gtcacgccaa taatcgattg cacattcgtc aagttagtat aaa        53

<210> SEQ ID NO 9
<211> LENGTH: 101
<212> TYPE: DNA
<213> ORGANISM: Artificial Sequence
<220> FEATURE:
<223> OTHER INFORMATION: primer

<400> SEQUENCE: 9 cctgctttt tatactaagt tggcattata aaaagcatt gcttatcaat tgttgcaac    60 gaacaggtca ctatcagtca aataaaatc attatttgat t                      101

<210> SEQ ID NO 10
<211> LENGTH: 172
<212> TYPE: DNA
<213> ORGANISM: Artificial Sequence
<220> FEATURE:
<223> OTHER INFORMATION: primer

<400> SEQUENCE: 10
gcgctaatgc tctgttacag gtcactaata ccatctaagt agttgattca tagtgactgc   60
atatgttgtg ttttacagta ttatgtagtc tgttttttat gcaaaatcta atttaatata  120
ttgatattta tatcatttta cgtttctcgt tcagcttttt tatactaact tg          172

<210> SEQ ID NO 11
<211> LENGTH: 120
<212> TYPE: DNA
<213> ORGANISM: Artificial Sequence
<220> FEATURE:
<223> OTHER INFORMATION: primer

<400> SEQUENCE: 11
agatcttgaa gcctgctttt ttatactaag ttggcattat aaaaagcat tgcttatcaa   60 tttgttgcaa cgaacaggtc actatcagtc aaaataaaat cattatttga tttcgaattc  120

<210> SEQ ID NO 12
<211> LENGTH: 184
<212> TYPE: DNA
<213> ORGANISM: Artificial Sequence
<220> FEATURE:
<223> OTHER INFORMATION: primer

<400> SEQUENCE: 12

```
ctgcagtctg ttacaggtca ctaataccat ctaagtagtt gattcatagt gactgcatat      60
gttgtgtttt acagtattat gtagtctgtt ttttatgcaa aatctaattt aatatattga     120
tatttatatc attttacgtt tctcgttcag cttttttata ctaacttgag cgtctagaaa     180
gctt                                                                   184
```

<210> SEQ ID NO 13
<211> LENGTH: 1071
<212> TYPE: DNA
<213> ORGANISM: Artificial Sequence
<220> FEATURE:
<221> NAME/KEY: CDS
<222> LOCATION: (1)..(1071)
<223> OTHER INFORMATION: primer

<400> SEQUENCE: 13

```
atg gga aga agg cga agt cat gag cgc cgg gat tta ccc cct aac ctt       48
Met Gly Arg Arg Arg Ser His Glu Arg Arg Asp Leu Pro Pro Asn Leu
1               5                   10                  15 tat ata aga aac aat gga tat tac tgc tac agg gac cca agg acg ggt       96
Tyr Ile Arg Asn Asn Gly Tyr Tyr Cys Tyr Arg Asp Pro Arg Thr Gly
            20                  25                  30 aaa gag ttt gga tta ggc aga gac agg cga atc gca atc act gaa gct      144
Lys Glu Phe Gly Leu Gly Arg Asp Arg Arg Ile Ala Ile Thr Glu Ala
        35                  40                  45 ata cag gcc aac att gag tta ttt tca gga cac aaa cac aag cct ctg      192
Ile Gln Ala Asn Ile Glu Leu Phe Ser Gly His Lys His Lys Pro Leu
    50                  55                  60 aca gcg aga atc aac agt gat aat tcc gtt acg tta cat tca tgg ctt      240
Thr Ala Arg Ile Asn Ser Asp Asn Ser Val Thr Leu His Ser Trp Leu
65                  70                  75                  80 gat cgc tac gaa aaa atc ctg gcc agc aga gga atc aag cag aag aca      288
Asp Arg Tyr Glu Lys Ile Leu Ala Ser Arg Gly Ile Lys Gln Lys Thr
                85                  90                  95 ctc ata aat tac atg agc aaa att aaa gca ata agg agg ggt ctg cct      336
Leu Ile Asn Tyr Met Ser Lys Ile Lys Ala Ile Arg Arg Gly Leu Pro
            100                 105                 110 gat gct cca ctt gaa gac atc acc aca aaa gaa att gcg gca atg ctc      384
Asp Ala Pro Leu Glu Asp Ile Thr Thr Lys Glu Ile Ala Ala Met Leu
        115                 120                 125 aat gga tac ata gac gag ggc aag gcg gcg tca gcc aag tta atc aga      432
Asn Gly Tyr Ile Asp Glu Gly Lys Ala Ala Ser Ala Lys Leu Ile Arg
    130                 135                 140 tca aca ctg agc gat gca ttc cga gag gca ata gct gaa ggc cat ata      480
Ser Thr Leu Ser Asp Ala Phe Arg Glu Ala Ile Ala Glu Gly His Ile
145                 150                 155                 160 aca aca aac cat gtc gct gcc act cgc gca gca aaa tca gag gta agg      528
Thr Thr Asn His Val Ala Ala Thr Arg Ala Ala Lys Ser Glu Val Arg
                165                 170                 175 aga tca aga ctt acg gct gac gaa tac ctg aaa att tat caa gca gca      576
Arg Ser Arg Leu Thr Ala Asp Glu Tyr Leu Lys Ile Tyr Gln Ala Ala
            180                 185                 190 gaa tca tca cca tgt tgg ctc aga ctt gca atg gaa ctg gct gtt gtt      624
Glu Ser Ser Pro Cys Trp Leu Arg Leu Ala Met Glu Leu Ala Val Val
        195                 200                 205 acc ggg caa cga gtt ggt gat tta tgc gaa atg aag tgg tct gat atc      672
Thr Gly Gln Arg Val Gly Asp Leu Cys Glu Met Lys Trp Ser Asp Ile
    210                 215                 220
```

```
gta gat gga tat ctt tat gtc gag caa agc aaa aca ggc gta aaa att    720
Val Asp Gly Tyr Leu Tyr Val Glu Gln Ser Lys Thr Gly Val Lys Ile
225                 230                 235                 240 gcc atc cca aca gca ttg cat att gat gct ctc gga ata tca atg aag    768
Ala Ile Pro Thr Ala Leu His Ile Asp Ala Leu Gly Ile Ser Met Lys
            245                 250                 255 gaa aca ctt gat aaa tgc aaa gag att ctt ggc gga gaa acc ata att    816
Glu Thr Leu Asp Lys Cys Lys Glu Ile Leu Gly Gly Glu Thr Ile Ile
        260                 265                 270 gca tct act cgt cgc gaa ccg ctt tca tcc ggc aca gta tca agg tat    864
Ala Ser Thr Arg Arg Glu Pro Leu Ser Ser Gly Thr Val Ser Arg Tyr
    275                 280                 285 ttt atg cgc gca cga aaa gca tca ggt ctt tcc ttc gaa ggg gat ccg    912
Phe Met Arg Ala Arg Lys Ala Ser Gly Leu Ser Phe Glu Gly Asp Pro
290                 295                 300 cct acc ttt cac gag ttg cgc agt ttg tct gca aga ctc tat gag aag    960
Pro Thr Phe His Glu Leu Arg Ser Leu Ser Ala Arg Leu Tyr Glu Lys
305                 310                 315                 320 cag ata agc gat aag ttt gct caa cat ctt ctc ggg cat aag tcg gac    1008
Gln Ile Ser Asp Lys Phe Ala Gln His Leu Leu Gly His Lys Ser Asp
            325                 330                 335 acc atg gca tca cag tat cgt gat gac aga ggc agg gag tgg gac aaa    1056
Thr Met Ala Ser Gln Tyr Arg Asp Asp Arg Gly Arg Glu Trp Asp Lys
        340                 345                 350 att gaa atc aaa taa                                                1071
Ile Glu Ile Lys
    355

<210> SEQ ID NO 14
<211> LENGTH: 356
<212> TYPE: PRT
<213> ORGANISM: Artificial Sequence
<220> FEATURE:
<223> OTHER INFORMATION: primer

<400> SEQUENCE: 14

Met Gly Arg Arg Arg Ser His Glu Arg Arg Asp Leu Pro Pro Asn Leu
1               5                   10                  15

Tyr Ile Arg Asn Asn Gly Tyr Tyr Cys Tyr Arg Asp Pro Arg Thr Gly
            20                  25                  30

Lys Glu Phe Gly Leu Gly Arg Asp Arg Arg Ile Ala Ile Thr Glu Ala
        35                  40                  45

Ile Gln Ala Asn Ile Glu Leu Phe Ser Gly His Lys His Lys Pro Leu
    50                  55                  60

Thr Ala Arg Ile Asn Ser Asp Asn Ser Val Thr Leu His Ser Trp Leu
65                  70                  75                  80

Asp Arg Tyr Glu Lys Ile Leu Ala Ser Arg Gly Ile Lys Gln Lys Thr
                85                  90                  95

Leu Ile Asn Tyr Met Ser Lys Ile Lys Ala Ile Arg Arg Gly Leu Pro
            100                 105                 110

Asp Ala Pro Leu Glu Asp Ile Thr Thr Lys Glu Ile Ala Ala Met Leu
        115                 120                 125

Asn Gly Tyr Ile Asp Glu Gly Lys Ala Ala Ser Ala Lys Leu Ile Arg
    130                 135                 140

Ser Thr Leu Ser Asp Ala Phe Arg Glu Ala Ile Ala Glu Gly His Ile
145                 150                 155                 160

Thr Thr Asn His Val Ala Ala Thr Arg Ala Ala Lys Ser Glu Val Arg
                165                 170                 175
```

```
Arg Ser Arg Leu Thr Ala Asp Glu Tyr Leu Lys Ile Tyr Gln Ala Ala
            180                 185                 190

Glu Ser Ser Pro Cys Trp Leu Arg Leu Ala Met Glu Leu Ala Val Val
            195                 200                 205

Thr Gly Gln Arg Val Gly Asp Leu Cys Glu Met Lys Trp Ser Asp Ile
        210                 215                 220

Val Asp Gly Tyr Leu Tyr Val Glu Gln Ser Lys Thr Gly Val Lys Ile
225                 230                 235                 240

Ala Ile Pro Thr Ala Leu His Ile Asp Ala Leu Gly Ile Ser Met Lys
                245                 250                 255

Glu Thr Leu Asp Lys Cys Lys Glu Ile Leu Gly Gly Glu Thr Ile Ile
            260                 265                 270

Ala Ser Thr Arg Arg Glu Pro Leu Ser Ser Gly Thr Val Ser Arg Tyr
        275                 280                 285

Phe Met Arg Ala Arg Lys Ala Ser Gly Leu Ser Phe Glu Gly Asp Pro
290                 295                 300

Pro Thr Phe His Glu Leu Arg Ser Leu Ser Ala Arg Leu Tyr Glu Lys
305                 310                 315                 320

Gln Ile Ser Asp Lys Phe Ala Gln His Leu Leu Gly His Lys Ser Asp
                325                 330                 335

Thr Met Ala Ser Gln Tyr Arg Asp Asp Arg Gly Arg Glu Trp Asp Lys
            340                 345                 350

Ile Glu Ile Lys
        355

<210> SEQ ID NO 15
<211> LENGTH: 219
<212> TYPE: DNA
<213> ORGANISM: Artificial sequence
<220> FEATURE:
<221> NAME/KEY: CDS
<222> LOCATION: (1)..(219)
<223> OTHER INFORMATION: primer

<400> SEQUENCE: 15 atg tac ttg aca ctt cag gag tgg aac gca cgc cag cga cgt cca aga      48
Met Tyr Leu Thr Leu Gln Glu Trp Asn Ala Arg Gln Arg Arg Pro Arg
1               5                   10                  15 agc ctt gaa aca gtt cgt cga tgg gtt cgg gaa tgc agg ata ttc cca      96
Ser Leu Glu Thr Val Arg Arg Trp Val Arg Glu Cys Arg Ile Phe Pro
            20                  25                  30 cct ccg gtt aag gat gga aga gag tat ctg ttc cac gaa tca gcg gta     144
Pro Pro Val Lys Asp Gly Arg Glu Tyr Leu Phe His Glu Ser Ala Val
        35                  40                  45 aag gtt gac tta aat cga cca gta aca ggt ggc ctt ttg aag agg atc     192
Lys Val Asp Leu Asn Arg Pro Val Thr Gly Gly Leu Leu Lys Arg Ile
50                  55                  60 aga aat ggg aag aag gcg aag tca tga                                 219
Arg Asn Gly Lys Lys Ala Lys Ser
65                  70

<210> SEQ ID NO 16
<211> LENGTH: 72
<212> TYPE: PRT
<213> ORGANISM: Artificial Sequence
<220> FEATURE:
<223> OTHER INFORMATION: primer

<400> SEQUENCE: 16

Met Tyr Leu Thr Leu Gln Glu Trp Asn Ala Arg Gln Arg Arg Pro Arg
```

```
  1               5                  10                 15
Ser Leu Glu Thr Val Arg Arg Trp Val Arg Glu Cys Arg Ile Phe Pro
             20                 25                 30

Pro Pro Val Lys Asp Gly Arg Glu Tyr Leu Phe His Glu Ser Ala Val
         35                 40                 45

Lys Val Asp Leu Asn Arg Pro Val Thr Gly Gly Leu Leu Lys Arg Ile
     50                 55                 60

Arg Asn Gly Lys Lys Ala Lys Ser
 65                 70
```

<210> SEQ ID NO 17
<211> LENGTH: 40
<212> TYPE: DNA
<213> ORGANISM: Artificial Sequence
<220> FEATURE:
<223> OTHER INFORMATION: oligonucleotide P1

<400> SEQUENCE: 17
ctagtaagat cttgaagcct gctttttat actaagttgg                    40

<210> SEQ ID NO 18
<211> LENGTH: 41
<212> TYPE: DNA
<213> ORGANISM: Artificial Sequence
<220> FEATURE:
<223> OTHER INFORMATION: oligonucleotide P2

<400> SEQUENCE: 18
atgatcgaat tcgaaatcaa ataatgattt tattttgact g                 41

<210> SEQ ID NO 19
<211> LENGTH: 41
<212> TYPE: DNA
<213> ORGANISM: Artificial Sequence
<220> FEATURE:
<223> OTHER INFORMATION: oligonucleotide P3

<400> SEQUENCE: 19
atgccactgc agtctgttac aggtcactaa taccatctaa g                 41

<210> SEQ ID NO 20
<211> LENGTH: 46
<212> TYPE: DNA
<213> ORGANISM: Artificial Sequence
<220> FEATURE:
<223> OTHER INFORMATION: oligonucleotide P4

<400> SEQUENCE: 20
accgttaagc tttctagacg ctcaagttag tataaaaaag ctgaac            46

<210> SEQ ID NO 21
<211> LENGTH: 38
<212> TYPE: DNA
<213> ORGANISM: Artificial Sequence
<220> FEATURE:
<223> OTHER INFORMATION: oligonucleotide P5

<400> SEQUENCE: 21
ttcttagacg tcaggtggca cttttcgggg aaatgtgc                     38

<210> SEQ ID NO 22
<211> LENGTH: 37
<212> TYPE: DNA
<213> ORGANISM: Artificial Sequence
<220> FEATURE:
<223> OTHER INFORMATION: oligonucleotide P6

<400> SEQUENCE: 22
taacagagat ctcgcgcaga aaaaaaggat ctcaaga          37

<210> SEQ ID NO 23
<211> LENGTH: 46
<212> TYPE: DNA
<213> ORGANISM: Artificial Sequence
<220> FEATURE:
<223> OTHER INFORMATION: oligonucleotide P7

<400> SEQUENCE: 23
aacagagatc taagcttaga tcctttgcct ggcggcagta gcgcgg          46

<210> SEQ ID NO 24
<211> LENGTH: 35
<212> TYPE: DNA
<213> ORGANISM: Artificial Sequence
<220> FEATURE:
<223> OTHER INFORMATION: oligonucleotide P8

<400> SEQUENCE: 24
ataaactgca gcaaaaagag tttgtagaaa cgcaa          35

<210> SEQ ID NO 25
<211> LENGTH: 36
<212> TYPE: DNA
<213> ORGANISM: Artificial Sequence
<220> FEATURE:
<223> OTHER INFORMATION: oligonucleotide P9

<400> SEQUENCE: 25
agtaattcta gaaagcttaa cacagaaaaa agcccg          36

<210> SEQ ID NO 26
<211> LENGTH: 43
<212> TYPE: DNA
<213> ORGANISM: Artificial Sequence
<220> FEATURE:
<223> OTHER INFORMATION: oligonucleotide P10

<400> SEQUENCE: 26
ctagtaggat ccctgcagtg gtcgaaaaaa aaagcccgca ctg          43

<210> SEQ ID NO 27
<211> LENGTH: 37
<212> TYPE: DNA
<213> ORGANISM: Artificial Sequence
<220> FEATURE:
<223> OTHER INFORMATION: oligonucleotide P11

<400> SEQUENCE: 27
atcgaggtac cagatctccg gataagtaga cagcctg          37

<210> SEQ ID NO 28
<211> LENGTH: 32
<212> TYPE: DNA
<213> ORGANISM: Artificial Sequence
<220> FEATURE:
<223> OTHER INFORMATION: oligonucleotide P12

<400> SEQUENCE: 28
gaaggtctag agcgcccggt tgacgctgct ag          32

<210> SEQ ID NO 29
<211> LENGTH: 1388
<212> TYPE: DNA
<213> ORGANISM: Artificial Sequence
<220> FEATURE:
<223> OTHER INFORMATION: cloned DNA fragment EcoRI-PstI including gene
for tetracycline resistance (small EcoRI-Van91I fragment of
pBR322) and transcription terminator ter_thrL

<400> SEQUENCE: 29

```
gaattctcat gtttgacagc ttatcatcga taagctttaa tgcggtagtt tatcacagtt        60
aaattgctaa cgcagtcagg caccgtgtat gaaatctaac aatgcgctca tcgtcatcct       120
cggcaccgtc accctggatg ctgtaggcat aggcttggtt atgccggtac tgccgggcct       180
cttgcgggat atcgtccatt ccgacagcat cgccagtcac tatggcgtgc tgctagcgct       240
atatgcgttg atgcaatttc tatgcgcacc cgttctcgga gcactgtccg accgctttgg       300
ccgccgccca gtcctgctcg cttcgctact tggagccact atcgactacg cgatcatggc       360
gaccacaccc gtcctgtgga tcctctacgc cggacgcatc gtggccggca tcaccggcgc       420
cacaggtgcg gttgctggcg cctatatcgc cgacatcacc gatggggaag atcgggctcg       480
ccacttcggg ctcatgagcg cttgtttcgg cgtgggtatg gtggcaggcc ccgtggccgg       540
gggactgttg ggcgccatct ccttgcatgc accattcctt gcggcggcgg tgctcaacgg       600
cctcaaccta ctactgggct gcttcctaat gcaggagtcg cataagggag agcgtcgacc       660
gatgcccttg agagccttca acccagtcag ctccttccgg tgggcgcggg gcatgactat       720
cgtcgccgca cttatgactg tcttctttat catgcaactc gtaggacagg tgccggcagc       780
gctctgggtc attttcggcg aggaccgctt tcgctggagc gcgacgatga tcggcctgtc       840
gcttgcggta ttcggaatct tgcacgccct cgctcaagcc ttcgtcactg gtcccgccac       900
caaacgtttc ggcgagaagc aggccattat cgccggcatg gcggccgacg cgctgggcta       960
cgtcttgctg gcgttcgcga cgcgaggctg gatggccttc cccattatga ttcttctcgc      1020
ttccggcggc atcgggatgc cgcgttgca ggccatgctg tccaggcagg tagatgacga      1080
ccatcaggga cagcttcaag atcgctcgc ggctcttacc agcctaactt cgatcactgg      1140
accgctgatc gtcacggcga tttatgccgc ctcggcgagc acatggaacg ggttggcatg      1200
gattgtaggc gccgccctat accttgtctg cctccccgcg ttgcgtcgcg gtgcatggag      1260
ccgggccacc tcgacctgaa tggaagccgg cggcacctcg ctaacggatt caccactcca      1320
actagaaagc ttaacacaga aaaaagcccg cacctgacag tgcgggcttt ttttttcgac      1380
cactgcag                                                              1388
```

<210> SEQ ID NO 30
<211> LENGTH: 1162
<212> TYPE: DNA
<213> ORGANISM: Artificial Sequence
<220> FEATURE:
<223> OTHER INFORMATION: cloned DNA fragment containing artificial DNA
fragment including promoter PA2 (early promoter of phage T7), cat
gene for chloramphenicol resistance (CmR), transcription
terminator ter_thrL and attR

<400> SEQUENCE: 30

```
agatctccgg ataagtagac agcctgataa gtcgcacgaa aacaggtat tgacaacatg        60
aagtaacatg cagtaagata caaatcgcta ggtaacacta gcagcgtcaa ccgggcgctc       120
tagctagagc caagctagct tggccggatc cgagattttc aggagctaag gaagctaaaa       180
```

```
tggagaaaaa aatcactgga tataccaccg ttgatatatc ccaatggcat cgtaaagaac    240
attttgaggc atttcagtca gttgctcaat gtacctataa ccagaccgtt cagctggata    300
ttacggcctt tttaaagacc gtaaagaaaa ataagcacaa gttttatccg gcctttattc    360
acattcttgc ccgcctgatg aatgctcatc cggaattccg tatggcaatg aaagacggtg    420
agctggtgat atgggatagt gttcacccct gttacaccgt tttccatgag caaactgaaa    480
cgttttcatc gctctggagt gaataccacg acgatttccg gcagtttcta cacatatatt    540
cgcaagatgt ggcgtgttac ggtgaaaacc tggcctattt ccctaaaggg tttattgaga    600
atatgttttt cgtctcagcc aatccctggg tgagtttcac cagttttgat ttaaacgtgg    660
ccaatatgga caacttcttc gccccgtttt tcaccatggg caaatattat acgcaaggcg    720
acaaggtgct gatgccgctg gcgattcagg ttcatcatgc cgtctgtgat ggcttccatg    780
tcggcagaat gcttaatgaa ttacaacagt actgcgatga gtggcagggc ggggcgtaat    840 tttttaagg cagttattgg tgcccttaaa cgcctggtgc tacgcctgaa taagtgataa    900
taagcggatg aatggcagaa attcgtcgaa gcttaacaca gaaaaaagcc cgcacctgac    960
agtgcgggct ttttttttcg accactgcag tctgttacag gtcactaata ccatctaagt   1020
agttgattca tagtgactgc atatgttgtg ttttacagta ttatgtagtc tgttttttat   1080
gcaaaatcta atttaatata ttgatattta tatcatttta cgtttctcgt tcagcttttt   1140
tatactaact tgagcgtcta ga                                             1162
```

<210> SEQ ID NO 31
<211> LENGTH: 27
<212> TYPE: DNA
<213> ORGANISM: Artificial Sequence
<220> FEATURE:
<223> OTHER INFORMATION: oligonucleotide P1'

<400> SEQUENCE: 31

```
ctaatatcga tgaagattct tgctcaa                                          27
```

<210> SEQ ID NO 32
<211> LENGTH: 34
<212> TYPE: DNA
<213> ORGANISM: Artificial Sequence
<220> FEATURE:
<223> OTHER INFORMATION: oligonucleotide P2'

<400> SEQUENCE: 32

```
gcgttgaatt ccatacaacc tccttagtac atgc                                  34
```

<210> SEQ ID NO 33
<211> LENGTH: 34
<212> TYPE: DNA
<213> ORGANISM: Artificial Sequence
<220> FEATURE:
<223> OTHER INFORMATION: oligonucleotide P3'

<400> SEQUENCE: 33

```
gtactagaat tcgtgtaatt gcggagactt tgcg                                  34
```

<210> SEQ ID NO 34
<211> LENGTH: 41
<212> TYPE: DNA
<213> ORGANISM: Artificial Sequence
<220> FEATURE:
<223> OTHER INFORMATION: oligonucleotide P4'

<400> SEQUENCE: 34
aatagcctgc agttatttga tttcaattt gtcccactcc c            41

<210> SEQ ID NO 35
<211> LENGTH: 38
<212> TYPE: DNA
<213> ORGANISM: Artificial Sequence
<220> FEATURE:
<223> OTHER INFORMATION: oligonucleotide P5'

<400> SEQUENCE: 35
ttcttagacg tcaggtggca cttttcgggg aaatgtgc               38

<210> SEQ ID NO 36
<211> LENGTH: 37
<212> TYPE: DNA
<213> ORGANISM: Artificial Sequence
<220> FEATURE:
<223> OTHER INFORMATION: oligonucleotide P6'

<400> SEQUENCE: 36
taacagagat ctagcgcaga aaaaaggat ctcaaga                 37

<210> SEQ ID NO 37
<211> LENGTH: 35
<212> TYPE: DNA
<213> ORGANISM: Artificial Sequence
<220> FEATURE:
<223> OTHER INFORMATION: oligonucleotide P7'

<400> SEQUENCE: 37
ataaactgca gcaaaaagag tttgtagaaa cgcaa                  35

<210> SEQ ID NO 38
<211> LENGTH: 34
<212> TYPE: DNA
<213> ORGANISM: Artificial Sequence
<220> FEATURE:
<223> OTHER INFORMATION: oligonucleotide P8'

<400> SEQUENCE: 38
aacagaagct ttttgcctgg cggcagtagc gcgg                   34

<210> SEQ ID NO 39
<211> LENGTH: 879
<212> TYPE: DNA
<213> ORGANISM: Artificial Sequence
<220> FEATURE:
<223> OTHER INFORMATION: cloned DNA fragment containing cI repressor
      gene and promoter regions

<400> SEQUENCE: 39
tcgatgaaga ttcttgctca attgttatca gctatgcgcc gaccagaaca ccttgccgat    60
cagccaaacg tctcttcagg ccactgacta gcgataactt tccccacaac ggaacaactc   120
tcattgcatg ggatcattgg gtactgtggg tttagtggtt gtaaaacac ctgaccgcta    180 tccctgatca gtttcttgaa ggtaaactca tcacccccaa gtctggctat gcagaaatca   240
cctggctcaa cagcctgctc agggtcaacg agaattaaca ttccgtcagg aaagcttggc   300
ttggagcctg ttggtgcggt catgaatta ccttcaacct caagccagaa tgcagaatca    360
ctggcttttt tggttgtgct tacccatctc tccgcatcac ctttggtaaa ggttctaagc   420
tcaggtgaga acatccctgc ctgaacatga gaaaaacag ggtactcata ctcacttcta    480
agtgacggct gcatactaac cgcttcatac atctcgtaga tttctctggc gattgaaggg   540

```
ctaaattctt caacgctaac tttgagaatt tttgcaagca atgcggcgtt ataagcattt      600
aatgcattga tgccattaaa taaagcacca acgcctgact gccccatccc catcttgtct      660
gcgacagatt cctgggataa gccaagttca ttttcttttt tttcataaat tgctttaagg      720
cgacgtgcgt cctcaagctg ctcttgtgtt aatggtttct tttttgtgct catacgttaa      780
atctatcacc gcaagggata aatatctaac accgtgcgtg ttgactattt tacctctggc      840
ggtgataatg gttgcatgta ctaaggaggt tgtatggaa                             879
```

<210> SEQ ID NO 40
<211> LENGTH: 1290
<212> TYPE: DNA
<213> ORGANISM: Artificial Sequence
<220> FEATURE:
<223> OTHER INFORMATION: cloned DNA fragment containing int-xis genes

<400> SEQUENCE: 40

```
attatttgat tcaattttg tcccactccc tgcctctgtc atcacgatac tgtgatgcca       60
tggtgtccga cttatgcccg agaagatgtt gagcaaactt atcgcttatc tgcttctcat      120
agagtcttgc agacaaactg cgcaactcgt gaaaggtagg cggatcccct tcgaaggaaa      180
gacctgatgc ttttcgtgcg cgcataaaat accttgatac tgtgccggat gaaagcggtt      240
cgcgacgagt agatgcaatt atggtttctc cgccaagaat ctctttgcat ttatcaagtg      300
tttccttcat tgatattccg agagcatcaa tatgcaatgc tgttgggatg gcaatttta      360 cgcctgtttt gctttgctcg acataaagat atccatctac gatatcagac cacttcattt      420
cgcataaatc accaactcgt tgcccggtaa caacagccag ttccattgca agtctgagcc      480
aacatggtga tgattctgct gcttgataaa ttttcaggta ttcgtcagcc gtaagtcttg      540
atctccttac ctctgatttt gctgcgcgag tggcagcgac atggtttgtt gttatatggc      600
cttcagctat tgcctctcgg aatgcatcgc tcagtgttga tctgattaac ttggctgacg      660
ccgccttgcc ctcgtctatg tatccattga gcattgccgc aatttctttt gtggtgatgt      720
cttcaagtgg agcatcaggc agacccctcc ttattgcttt aattttgctc atgtaattta      780
tgagtgtctt ctgcttgatt cctctgctgg ccaggatttt ttcgtagcga tcaagccatg      840
aatgtaacgt aacggaatta tcactgttga ttctcgctgt cagaggcttg tgttgtgtc      900 ctgaaaataa ctcaatgttg gcctgtatag cttcagtgat tgcgattcgc ctgtctctgc      960
ctaatccaaa ctctttaccc gtccttgggt ccctgtagca gtaatatcca ttgtttctta      1020
tataaaggtt aggggggtaaa tcccggcgct catgacttcg ccttcttccc atttctgatc      1080
ctcttcaaaa ggccacctgt tactggtcga tttaagtcaa cctttaccgc tgattcgtgg      1140
aacagatact ctcttccatc cttaaccgga ggtgggaata tcctgcattc ccgaacccat      1200
cgacgaactg tttcaaggct tcttggacgt cgctggcgtg cgttccactc ctgaagtgtc      1260
aagtacatcg caaagtctcc gcaattacac                                      1290
```

<210> SEQ ID NO 41
<211> LENGTH: 351
<212> TYPE: DNA
<213> ORGANISM: Artificial Sequence
<220> FEATURE:
<223> OTHER INFORMATION: ter_rrnB fragment (complement)

<400> SEQUENCE: 41

```
caaaaagagt ttgtagaaac gcaaaaaggc catccgtcag gatggccttc tgcttaattt      60
```

```
gatgcctggc agtttatggc gggcgtcctg cccgccaccc tccgggccgt tgcttcgcaa      120
cgttcaaatc cgctcccggc ggatttgtcc tactcaggag agcgttcacc gacaaacaac      180
agataaaacg aaaggcccag tctttcgact gagcctttcg tttatttga tgcctggcag       240 ttccctactc tcgcatgggg agaccccaca ctaccatcgg cgctacggcg tttcacttct      300
gagttcggca tggggtcagg tgggaccacc gcgctactgc cgccaggcaa a               351
```

<210> SEQ ID NO 42
<211> LENGTH: 2148
<212> TYPE: DNA
<213> ORGANISM: Escherichia coli
<220> FEATURE:
<221> NAME/KEY: CDS
<222> LOCATION: (1)..(2148)

<400> SEQUENCE: 42

```
atg aac gtt att gca ata ttg aat cac atg ggg gtt tat ttt aaa gaa       48
Met Asn Val Ile Ala Ile Leu Asn His Met Gly Val Tyr Phe Lys Glu
1               5                   10                  15 gaa ccc atc cgt gaa ctt cat cgc gcg ctt gaa cgt ctg aac ttc cag       96
Glu Pro Ile Arg Glu Leu His Arg Ala Leu Glu Arg Leu Asn Phe Gln
            20                  25                  30 att gtt tac ccg aac gac cgt gac gac tta tta aaa ctg atc gaa aac      144
Ile Val Tyr Pro Asn Asp Arg Asp Asp Leu Leu Lys Leu Ile Glu Asn
        35                  40                  45 aat gcg cgt ctg tgc ggc gtt att ttt gac tgg gat aaa tat aat ctc      192
Asn Ala Arg Leu Cys Gly Val Ile Phe Asp Trp Asp Lys Tyr Asn Leu
    50                  55                  60 gag ctg tgc gaa gaa att agc aaa atg aac gag aac ctg ccg ttg tac      240
Glu Leu Cys Glu Glu Ile Ser Lys Met Asn Glu Asn Leu Pro Leu Tyr
65                  70                  75                  80 gcg ttc gct aat acg tat tcc act ctc gat gta agc ctg aat gac ctg      288
Ala Phe Ala Asn Thr Tyr Ser Thr Leu Asp Val Ser Leu Asn Asp Leu
                85                  90                  95 cgt tta cag att agc ttc ttt gaa tat gcg ctg ggt gct gct gaa gat      336
Arg Leu Gln Ile Ser Phe Phe Glu Tyr Ala Leu Gly Ala Ala Glu Asp
            100                 105                 110 att gct aat aag atc aag cag acc act gac gaa tat atc aac act att      384
Ile Ala Asn Lys Ile Lys Gln Thr Thr Asp Glu Tyr Ile Asn Thr Ile
        115                 120                 125 ctg cct ccg ctg act aaa gca ctg ttt aaa tat gtt cgt gaa ggt aaa      432
Leu Pro Pro Leu Thr Lys Ala Leu Phe Lys Tyr Val Arg Glu Gly Lys
    130                 135                 140 tat act ttc tgt act cct ggt cac atg ggc ggt act gca ttc cag aaa      480
Tyr Thr Phe Cys Thr Pro Gly His Met Gly Gly Thr Ala Phe Gln Lys
145                 150                 155                 160 agc ccg gta ggt agc ctg ttc tat gat ttc ttt ggt ccg aat acc atg      528
Ser Pro Val Gly Ser Leu Phe Tyr Asp Phe Phe Gly Pro Asn Thr Met
                165                 170                 175 aaa tct gat att tcc att tca gta tct gaa ctg ggt tct ctg ctg gat      576
Lys Ser Asp Ile Ser Ile Ser Val Ser Glu Leu Gly Ser Leu Leu Asp
            180                 185                 190 cac agt ggt cca cac aaa gaa gca gaa cag tat atc gct cgc gtc ttt      624
His Ser Gly Pro His Lys Glu Ala Glu Gln Tyr Ile Ala Arg Val Phe
        195                 200                 205 aac gca gac cgc agc tac atg gtg acc aac ggt act tcc act gcg aac      672
Asn Ala Asp Arg Ser Tyr Met Val Thr Asn Gly Thr Ser Thr Ala Asn
    210                 215                 220 aaa att gtt ggt atg tac tct gct cca gca ggc agc acc att ctg att      720
Lys Ile Val Gly Met Tyr Ser Ala Pro Ala Gly Ser Thr Ile Leu Ile
```

|  |  |  |  |  | 225 |  |  |  |  | 230 |  |  |  |  | 235 |  |  |  |  | 240 |  |
|---|---|---|---|---|---|---|---|---|---|---|---|---|---|---|---|---|---|---|---|---|---|

```
gac cgt aac tgc cac aaa tcg ctg acc cac ctg atg atg atg agc gat      768
Asp Arg Asn Cys His Lys Ser Leu Thr His Leu Met Met Met Ser Asp
                    245                 250                 255 gtt acg cca atc tat ttc cgc ccg acc cgt aac gct tac ggt att ctt      816
Val Thr Pro Ile Tyr Phe Arg Pro Thr Arg Asn Ala Tyr Gly Ile Leu
        260                 265                 270 ggt ggt atc cca cag agt gaa ttc cag cac gct acc att gct aag cgc      864
Gly Gly Ile Pro Gln Ser Glu Phe Gln His Ala Thr Ile Ala Lys Arg
            275                 280                 285 gtg aaa gaa aca cca aac gca acc tgg ccg gta cat gct gta att acc      912
Val Lys Glu Thr Pro Asn Ala Thr Trp Pro Val His Ala Val Ile Thr
290                 295                 300 aac tct acc tat gat ggt ctg ctg tac aac acc gac ttc atc aag aaa      960
Asn Ser Thr Tyr Asp Gly Leu Leu Tyr Asn Thr Asp Phe Ile Lys Lys
305                 310                 315                 320 aca ctg gat gtg aaa tcc atc cac ttt gac tcc gcg tgg gtg cct tac     1008
Thr Leu Asp Val Lys Ser Ile His Phe Asp Ser Ala Trp Val Pro Tyr
                    325                 330                 335 acc aac ttc tca ccg att tac gaa ggt aaa tgc ggt atg agc ggt ggc     1056
Thr Asn Phe Ser Pro Ile Tyr Glu Gly Lys Cys Gly Met Ser Gly Gly
        340                 345                 350 cgt gta gaa ggg aaa gtg att tac gaa acc cag tcc act cac aaa ctg     1104
Arg Val Glu Gly Lys Val Ile Tyr Glu Thr Gln Ser Thr His Lys Leu
            355                 360                 365 ctg gcg gcg ttc tct cag gct tcc atg atc cac gtt aaa ggt gac gta     1152
Leu Ala Ala Phe Ser Gln Ala Ser Met Ile His Val Lys Gly Asp Val
370                 375                 380 aac gaa gaa acc ttt aac gaa gcc tac atg atg cac acc acc act tct     1200
Asn Glu Glu Thr Phe Asn Glu Ala Tyr Met Met His Thr Thr Thr Ser
385                 390                 395                 400 ccg cac tac ggt atc gtg gcg tcc act gaa acc gct gcg gcg atg atg     1248
Pro His Tyr Gly Ile Val Ala Ser Thr Glu Thr Ala Ala Ala Met Met
                    405                 410                 415 aaa ggc aat gca ggt aag cgt ctg atc aac ggt tct att gaa cgt gcg     1296
Lys Gly Asn Ala Gly Lys Arg Leu Ile Asn Gly Ser Ile Glu Arg Ala
        420                 425                 430 atc aaa ttc cgt aaa gag atc aaa cgt ctg aga acg gaa tct gat ggc     1344
Ile Lys Phe Arg Lys Glu Ile Lys Arg Leu Arg Thr Glu Ser Asp Gly
            435                 440                 445 tgg ttc ttt gat gta tgg cag ccg gat cat atc gat acg act gaa tgc     1392
Trp Phe Phe Asp Val Trp Gln Pro Asp His Ile Asp Thr Thr Glu Cys
450                 455                 460 tgg ccg ctg cgt tct gac agc acc tgg cac ggc ttc aaa aac atc gat     1440
Trp Pro Leu Arg Ser Asp Ser Thr Trp His Gly Phe Lys Asn Ile Asp
465                 470                 475                 480 aac gag cac atg tat ctt gac ccg atc aaa gtc acc ctg ctg act ccg     1488
Asn Glu His Met Tyr Leu Asp Pro Ile Lys Val Thr Leu Leu Thr Pro
                    485                 490                 495 ggg atg gaa aaa gac ggc acc atg agc gac ttt ggt att ccg gcc agc     1536
Gly Met Glu Lys Asp Gly Thr Met Ser Asp Phe Gly Ile Pro Ala Ser
        500                 505                 510 atc gtg gcg aaa tac ctc gac gaa cat ggc atc gtt gtt gag aaa acc     1584
Ile Val Ala Lys Tyr Leu Asp Glu His Gly Ile Val Val Glu Lys Thr
            515                 520                 525 ggt ccg tat aac ctg ctg ttc ctg ttc agc atc ggt atc gat aag acc     1632
Gly Pro Tyr Asn Leu Leu Phe Leu Phe Ser Ile Gly Ile Asp Lys Thr
530                 535                 540 aaa gca ctg agc ctg ctg cgt gct ctg act gac ttt aaa cgt gcg ttc     1680
```

```
Lys Ala Leu Ser Leu Leu Arg Ala Leu Thr Asp Phe Lys Arg Ala Phe
545                 550                 555                 560 gac ctg aac ctg cgt gtg aaa aac atg ctg ccg tct ctg tat cgt gaa      1728
Asp Leu Asn Leu Arg Val Lys Asn Met Leu Pro Ser Leu Tyr Arg Glu
                565                 570                 575 gat cct gaa ttc tat gaa aac atg cgt att cag gaa ctg gct cag aat      1776
Asp Pro Glu Phe Tyr Glu Asn Met Arg Ile Gln Glu Leu Ala Gln Asn
            580                 585                 590 atc cac aaa ctg att gtt cac cac aat ctg ccg gat ctg atg tat cgc      1824
Ile His Lys Leu Ile Val His His Asn Leu Pro Asp Leu Met Tyr Arg
        595                 600                 605 gca ttt gaa gtg ctg ccg acg atg gta atg act ccg tat gct gca ttc      1872
Ala Phe Glu Val Leu Pro Thr Met Val Met Thr Pro Tyr Ala Ala Phe
    610                 615                 620 cag aaa gag ctg cac ggt atg acc gaa gaa gtt tac ctc gac gaa atg      1920
Gln Lys Glu Leu His Gly Met Thr Glu Glu Val Tyr Leu Asp Glu Met
625                 630                 635                 640 gta ggt cgt att aac gcc aat atg atc ctt ccg tac ccg ccg gga gtt      1968
Val Gly Arg Ile Asn Ala Asn Met Ile Leu Pro Tyr Pro Pro Gly Val
                645                 650                 655 cct ctg gta atg ccg ggt gaa atg atc acc gaa gaa agc cgt ccg gtt      2016
Pro Leu Val Met Pro Gly Glu Met Ile Thr Glu Glu Ser Arg Pro Val
            660                 665                 670 ctg gag ttc ctg cag atg ctg tgt gaa atc ggc gct cac tat ccg ggc      2064
Leu Glu Phe Leu Gln Met Leu Cys Glu Ile Gly Ala His Tyr Pro Gly
        675                 680                 685 ttt gaa acc gat att cac ggt gca tac cgt cag gct gat ggc cgc tat      2112
Phe Glu Thr Asp Ile His Gly Ala Tyr Arg Gln Ala Asp Gly Arg Tyr
    690                 695                 700 acc gtt aag gta ttg aaa gaa gaa agc aaa aaa taa                      2148
Thr Val Lys Val Leu Lys Glu Glu Ser Lys Lys
705                 710                 715

<210> SEQ ID NO 43
<211> LENGTH: 715
<212> TYPE: PRT
<213> ORGANISM: Escherichia coli

<400> SEQUENCE: 43

Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
```

```
                        145                 150                 155                 160
            Ser Pro Val Gly Ser Leu Phe Tyr Asp Phe Phe Gly Pro Asn Thr Met
                        165                 170                 175
            Lys Ser Asp Ile Ser Ile Ser Val Ser Glu Leu Gly Ser Leu Leu Asp
                        180                 185                 190
            His Ser Gly Pro His Lys Glu Ala Glu Gln Tyr Ile Ala Arg Val Phe
                        195                 200                 205
            Asn Ala Asp Arg Ser Tyr Met Val Thr Asn Gly Thr Ser Thr Ala Asn
                        210                 215                 220
            Lys Ile Val Gly Met Tyr Ser Ala Pro Ala Gly Ser Thr Ile Leu Ile
            225                 230                 235                 240
            Asp Arg Asn Cys His Lys Ser Leu Thr His Leu Met Met Met Ser Asp
                        245                 250                 255
            Val Thr Pro Ile Tyr Phe Arg Pro Thr Arg Asn Ala Tyr Gly Ile Leu
                        260                 265                 270
            Gly Gly Ile Pro Gln Ser Glu Phe Gln His Ala Thr Ile Ala Lys Arg
                        275                 280                 285
            Val Lys Glu Thr Pro Asn Ala Thr Trp Pro Val His Ala Val Ile Thr
                        290                 295                 300
            Asn Ser Thr Tyr Asp Gly Leu Leu Tyr Asn Thr Asp Phe Ile Lys Lys
            305                 310                 315                 320
            Thr Leu Asp Val Lys Ser Ile His Phe Asp Ser Ala Trp Val Pro Tyr
                        325                 330                 335
            Thr Asn Phe Ser Pro Ile Tyr Glu Gly Lys Cys Gly Met Ser Gly Gly
                        340                 345                 350
            Arg Val Glu Gly Lys Val Ile Tyr Glu Thr Gln Ser Thr His Lys Leu
                        355                 360                 365
            Leu Ala Ala Phe Ser Gln Ala Ser Met Ile His Val Lys Gly Asp Val
                        370                 375                 380
            Asn Glu Glu Thr Phe Asn Glu Ala Tyr Met Met His Thr Thr Thr Ser
            385                 390                 395                 400
            Pro His Tyr Gly Ile Val Ala Ser Thr Glu Thr Ala Ala Ala Met Met
                        405                 410                 415
            Lys Gly Asn Ala Gly Lys Arg Leu Ile Asn Gly Ser Ile Glu Arg Ala
                        420                 425                 430
            Ile Lys Phe Arg Lys Glu Ile Lys Arg Leu Arg Thr Glu Ser Asp Gly
                        435                 440                 445
            Trp Phe Phe Asp Val Trp Gln Pro Asp His Ile Asp Thr Thr Glu Cys
                        450                 455                 460
            Trp Pro Leu Arg Ser Asp Ser Thr Trp His Gly Phe Lys Asn Ile Asp
            465                 470                 475                 480
            Asn Glu His Met Tyr Leu Asp Pro Ile Lys Val Thr Leu Leu Thr Pro
                        485                 490                 495
            Gly Met Glu Lys Asp Gly Thr Met Ser Asp Phe Gly Ile Pro Ala Ser
                        500                 505                 510
            Ile Val Ala Lys Tyr Leu Asp Glu His Gly Ile Val Val Glu Lys Thr
                        515                 520                 525
            Gly Pro Tyr Asn Leu Leu Phe Leu Phe Ser Ile Gly Ile Asp Lys Thr
                        530                 535                 540
            Lys Ala Leu Ser Leu Leu Arg Ala Leu Thr Asp Phe Lys Arg Ala Phe
            545                 550                 555                 560
            Asp Leu Asn Leu Arg Val Lys Asn Met Leu Pro Ser Leu Tyr Arg Glu
                        565                 570                 575
```

```
Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
    595                 600                 605

Ala Phe Glu Val Leu Pro Thr Met Val Met Thr Pro Tyr Ala Ala Phe
610                 615                 620

Gln Lys Glu Leu His Gly Met Thr Glu Val Tyr Leu Asp Glu Met
625                 630                 635                 640

Val Gly Arg Ile Asn Ala Asn Met Ile Leu Pro Tyr Pro Gly Val
            645                 650                 655

Pro Leu Val Met Pro Gly Glu Met Ile Thr Glu Ser Arg Pro Val
            660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
            690                 695                 700

Thr Val Lys Val Leu Lys Glu Ser Lys Lys
705                 710                 715

<210> SEQ ID NO 44
<211> LENGTH: 2142
<212> TYPE: DNA
<213> ORGANISM: Escherichia coli
<220> FEATURE:
<221> NAME/KEY: CDS
<222> LOCATION: (1)..(2142)

<400> SEQUENCE: 44 atg aac atc att gcc att atg gga ccg cat ggc gtc ttt tat aaa gat        48
Met Asn Ile Ile Ala Ile Met Gly Pro His Gly Val Phe Tyr Lys Asp
1               5                   10                  15 gag ccc atc aaa gaa ctg gag tcg gcg ctg gtg gcg caa ggc ttt cag        96
Glu Pro Ile Lys Glu Leu Glu Ser Ala Leu Val Ala Gln Gly Phe Gln
                20                  25                  30 att atc tgg cca caa aac agc gtt gat ttg ctg aaa ttt atc gag cat       144
Ile Ile Trp Pro Gln Asn Ser Val Asp Leu Leu Lys Phe Ile Glu His
        35                  40                  45 aac cct cga att tgc ggc gtg att ttt gac tgg gat gag tac agt ctc       192
Asn Pro Arg Ile Cys Gly Val Ile Phe Asp Trp Asp Glu Tyr Ser Leu
    50                  55                  60 gat tta tgt agc gat atc aat cag ctt aat gaa tat ctc ccg ctt tat       240
Asp Leu Cys Ser Asp Ile Asn Gln Leu Asn Glu Tyr Leu Pro Leu Tyr
65                  70                  75                  80 gcc ttc atc aac acc cac tcg acg atg gat gtc agc gtg cag gat atg       288
Ala Phe Ile Asn Thr His Ser Thr Met Asp Val Ser Val Gln Asp Met
                85                  90                  95 cgg atg gcg ctc tgg ttt ttt gaa tat gcg ctg ggg cag gcg gaa gat       336
Arg Met Ala Leu Trp Phe Phe Glu Tyr Ala Leu Gly Gln Ala Glu Asp
            100                 105                 110 atc gcc att cgt atg cgt cag tac acc gac gaa tat ctt gat aac att       384
Ile Ala Ile Arg Met Arg Gln Tyr Thr Asp Glu Tyr Leu Asp Asn Ile
        115                 120                 125 aca ccg ccg ttc acg aaa gcc ttg ttt acc tac gtc aaa gag cgg aag       432
Thr Pro Pro Phe Thr Lys Ala Leu Phe Thr Tyr Val Lys Glu Arg Lys
    130                 135                 140 tac acc ttt tgt acg ccg ggg cat atg ggc ggc acc gca tat caa aaa       480
Tyr Thr Phe Cys Thr Pro Gly His Met Gly Gly Thr Ala Tyr Gln Lys
145                 150                 155                 160
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| agc | ccg | gtt | ggc | tgt | ctg | ttt | tat | gat | ttt | ttc | ggc | ggg | aat | act | ctt | 528 |
| Ser | Pro | Val | Gly | Cys | Leu | Phe | Tyr | Asp | Phe | Phe | Gly | Gly | Asn | Thr | Leu | |
| | | | | 165 | | | | | 170 | | | | | 175 | | |
| aag | gct | gat | gtc | tct | att | tcg | gtc | acc | gag | ctt | ggt | tcg | ttg | ctc | gac | 576 |
| Lys | Ala | Asp | Val | Ser | Ile | Ser | Val | Thr | Glu | Leu | Gly | Ser | Leu | Leu | Asp | |
| | | | 180 | | | | | 185 | | | | | 190 | | | |
| cac | acc | ggg | cca | cac | ctg | gaa | gcg | gaa | gag | tac | atc | gcg | cgg | act | ttt | 624 |
| His | Thr | Gly | Pro | His | Leu | Glu | Ala | Glu | Glu | Tyr | Ile | Ala | Arg | Thr | Phe | |
| | | 195 | | | | | 200 | | | | | 205 | | | | |
| ggc | gcg | gaa | cag | agt | tat | atc | gtt | acc | aac | gga | aca | tcg | acg | tcg | aac | 672 |
| Gly | Ala | Glu | Gln | Ser | Tyr | Ile | Val | Thr | Asn | Gly | Thr | Ser | Thr | Ser | Asn | |
| | 210 | | | | | 215 | | | | | 220 | | | | | |
| aaa | att | gtg | ggt | atg | tac | gcc | gcg | cca | tcc | ggc | agt | acg | ctg | ttg | atc | 720 |
| Lys | Ile | Val | Gly | Met | Tyr | Ala | Ala | Pro | Ser | Gly | Ser | Thr | Leu | Leu | Ile | |
| 225 | | | | 230 | | | | | 235 | | | | | 240 | | |
| gac | cgc | aat | tgt | cat | aaa | tcg | ctg | gcg | cat | ctg | ttg | atg | atg | aac | gat | 768 |
| Asp | Arg | Asn | Cys | His | Lys | Ser | Leu | Ala | His | Leu | Leu | Met | Met | Asn | Asp | |
| | | | | 245 | | | | | 250 | | | | | 255 | | |
| gta | gtg | cca | gtc | tgg | ctg | aaa | ccg | acg | cgt | aat | gcg | ttg | ggg | att | ctt | 816 |
| Val | Val | Pro | Val | Trp | Leu | Lys | Pro | Thr | Arg | Asn | Ala | Leu | Gly | Ile | Leu | |
| | | | 260 | | | | | 265 | | | | | 270 | | | |
| ggt | ggg | atc | ccg | cgc | cgt | gaa | ttt | act | cgc | gac | agc | atc | gaa | gag | aaa | 864 |
| Gly | Gly | Ile | Pro | Arg | Arg | Glu | Phe | Thr | Arg | Asp | Ser | Ile | Glu | Glu | Lys | |
| | | 275 | | | | | 280 | | | | | 285 | | | | |
| gtc | gct | gct | acc | acg | caa | gca | caa | tgg | ccg | gtt | cat | gcg | gtg | atc | acc | 912 |
| Val | Ala | Ala | Thr | Thr | Gln | Ala | Gln | Trp | Pro | Val | His | Ala | Val | Ile | Thr | |
| | 290 | | | | | 295 | | | | | 300 | | | | | |
| aac | tcc | acc | tat | gat | ggc | ttg | ctc | tac | aac | acc | gac | tgg | atc | aaa | cag | 960 |
| Asn | Ser | Thr | Tyr | Asp | Gly | Leu | Leu | Tyr | Asn | Thr | Asp | Trp | Ile | Lys | Gln | |
| 305 | | | | 310 | | | | | 315 | | | | | 320 | | |
| acg | ctg | gat | gtc | ccg | tcg | att | cac | ttc | gat | tct | gcc | tgg | gtg | ccg | tac | 1008 |
| Thr | Leu | Asp | Val | Pro | Ser | Ile | His | Phe | Asp | Ser | Ala | Trp | Val | Pro | Tyr | |
| | | | | 325 | | | | | 330 | | | | | 335 | | |
| acc | cat | ttt | cat | ccg | atc | tac | cag | ggt | aaa | agt | ggt | atg | agc | ggc | gag | 1056 |
| Thr | His | Phe | His | Pro | Ile | Tyr | Gln | Gly | Lys | Ser | Gly | Met | Ser | Gly | Glu | |
| | | | 340 | | | | | 345 | | | | | 350 | | | |
| cgt | gtt | gcg | gga | aaa | gtg | atc | ttc | gaa | acg | caa | tcg | acc | cac | aaa | atg | 1104 |
| Arg | Val | Ala | Gly | Lys | Val | Ile | Phe | Glu | Thr | Gln | Ser | Thr | His | Lys | Met | |
| | | 355 | | | | | 360 | | | | | 365 | | | | |
| ctg | gcg | gcg | tta | tcg | cag | gct | tcg | ctg | atc | cac | att | aaa | ggc | gag | tat | 1152 |
| Leu | Ala | Ala | Leu | Ser | Gln | Ala | Ser | Leu | Ile | His | Ile | Lys | Gly | Glu | Tyr | |
| | 370 | | | | | 375 | | | | | 380 | | | | | |
| gac | gaa | gag | gcc | ttt | aac | gaa | gcc | ttt | atg | atg | cat | acc | acc | acc | tcg | 1200 |
| Asp | Glu | Glu | Ala | Phe | Asn | Glu | Ala | Phe | Met | Met | His | Thr | Thr | Thr | Ser | |
| 385 | | | | 390 | | | | | 395 | | | | | 400 | | |
| ccc | agt | tat | ccc | att | gtt | gct | tcg | gtt | gag | acg | gcg | gcg | gcg | atg | ctg | 1248 |
| Pro | Ser | Tyr | Pro | Ile | Val | Ala | Ser | Val | Glu | Thr | Ala | Ala | Ala | Met | Leu | |
| | | | | 405 | | | | | 410 | | | | | 415 | | |
| cgt | ggt | aat | ccg | ggc | aaa | cgg | ctg | att | aac | cgt | tca | gta | gaa | cga | gct | 1296 |
| Arg | Gly | Asn | Pro | Gly | Lys | Arg | Leu | Ile | Asn | Arg | Ser | Val | Glu | Arg | Ala | |
| | | | 420 | | | | | 425 | | | | | 430 | | | |
| ctg | cat | ttt | cgc | aaa | gag | gtc | cag | cgg | ctg | cgg | gaa | gag | tct | gac | ggt | 1344 |
| Leu | His | Phe | Arg | Lys | Glu | Val | Gln | Arg | Leu | Arg | Glu | Glu | Ser | Asp | Gly | |
| | | 435 | | | | | 440 | | | | | 445 | | | | |
| tgg | ttt | ttc | gat | atc | tgg | caa | ccg | ccg | cag | gtg | gat | gaa | gcc | gaa | tgc | 1392 |
| Trp | Phe | Phe | Asp | Ile | Trp | Gln | Pro | Pro | Gln | Val | Asp | Glu | Ala | Glu | Cys | |
| | 450 | | | | | 455 | | | | | 460 | | | | | |
| tgg | ccc | gtt | gcg | cct | ggc | gaa | cag | tgg | cac | ggc | ttt | aac | gat | gcg | gat | 1440 |
| Trp | Pro | Val | Ala | Pro | Gly | Glu | Gln | Trp | His | Gly | Phe | Asn | Asp | Ala | Asp | |
| 465 | | | | 470 | | | | | 475 | | | | | 480 | | |

```
gcc gat cat atg ttt ctc gat ccg gtt aaa gtc act att ttg aca ccg    1488
Ala Asp His Met Phe Leu Asp Pro Val Lys Val Thr Ile Leu Thr Pro
            485                 490                 495 ggg atg gac gag cag ggc aat atg agc gag gag ggg atc ccg gcg gcg    1536
Gly Met Asp Glu Gln Gly Asn Met Ser Glu Glu Gly Ile Pro Ala Ala
        500                 505                 510 ctg gta gca aaa ttc ctc gac gaa cgt ggg atc gta gta gag aaa acc    1584
Leu Val Ala Lys Phe Leu Asp Glu Arg Gly Ile Val Val Glu Lys Thr
                515                 520                 525 ggc cct tat aac ctg ctg ttt ctc ttt agt att ggc atc gat aaa acc    1632
Gly Pro Tyr Asn Leu Leu Phe Leu Phe Ser Ile Gly Ile Asp Lys Thr
    530                 535                 540 aaa gca atg gga tta ttg cgt ggg tta acg gaa ttc aaa cgc tct tac    1680
Lys Ala Met Gly Leu Leu Arg Gly Leu Thr Glu Phe Lys Arg Ser Tyr
545                 550                 555                 560 gat ctc aac ctg cgg atc aaa aat atg cta ccc gat ctc tat gca gaa    1728
Asp Leu Asn Leu Arg Ile Lys Asn Met Leu Pro Asp Leu Tyr Ala Glu
                565                 570                 575 gat ccc gat ttc tac cgc aat atg cgt att cag gat ctg gca caa ggg    1776
Asp Pro Asp Phe Tyr Arg Asn Met Arg Ile Gln Asp Leu Ala Gln Gly
            580                 585                 590 atc cat aag ctg att cgt aaa cac gat ctt ccc ggt ttg atg ttg cgg    1824
Ile His Lys Leu Ile Arg Lys His Asp Leu Pro Gly Leu Met Leu Arg
        595                 600                 605 gca ttc gat act ttg ccg gag atg atc atg acg cca cat cag gca tgg    1872
Ala Phe Asp Thr Leu Pro Glu Met Ile Met Thr Pro His Gln Ala Trp
    610                 615                 620 caa cga caa att aaa ggc gaa gta gaa acc att gcg ctg gaa caa ctg    1920
Gln Arg Gln Ile Lys Gly Glu Val Glu Thr Ile Ala Leu Glu Gln Leu
625                 630                 635                 640 gtc ggt aga gta tcg gca aat atg atc ctg cct tat cca ccg ggc gta    1968
Val Gly Arg Val Ser Ala Asn Met Ile Leu Pro Tyr Pro Pro Gly Val
                645                 650                 655 ccg ctg ttg atg cct gga gaa atg ctg acc aaa gag agc cgc aca gta    2016
Pro Leu Leu Met Pro Gly Glu Met Leu Thr Lys Glu Ser Arg Thr Val
            660                 665                 670 ctc gat ttt cta ctg atg ctt tgt tcc gtc ggg caa cat tac ccc ggt    2064
Leu Asp Phe Leu Leu Met Leu Cys Ser Val Gly Gln His Tyr Pro Gly
        675                 680                 685 ttt gaa acg gat att cac ggc gcg aaa cag gac gaa gac ggc gtt tac    2112
Phe Glu Thr Asp Ile His Gly Ala Lys Gln Asp Glu Asp Gly Val Tyr
    690                 695                 700 cgc gta cga gtc cta aaa atg gcg gga taa                            2142
Arg Val Arg Val Leu Lys Met Ala Gly
705                 710

<210> SEQ ID NO 45
<211> LENGTH: 713
<212> TYPE: PRT
<213> ORGANISM: Escherichia coli

<400> SEQUENCE: 45

Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
            20                  25                  30

Ile Ile Trp Pro Gln Asn Ser Val Asp Leu Leu Lys Phe Ile Glu His
        35                  40                  45

Asn Pro Arg Ile Cys Gly Val Ile Phe Asp Trp Asp Glu Tyr Ser Leu
```

-continued

```
             50                  55                  60
Asp Leu Cys Ser Asp Ile Asn Gln Leu Asn Glu Tyr Leu Pro Leu Tyr
 65                  70                  75                  80

Ala Phe Ile Asn Thr His Ser Thr Met Asp Val Ser Val Gln Asp Met
                 85                  90                  95

Arg Met Ala Leu Trp Phe Phe Glu Tyr Ala Leu Gly Gln Ala Glu Asp
            100                 105                 110

Ile Ala Ile Arg Met Arg Gln Tyr Thr Asp Glu Tyr Leu Asp Asn Ile
        115                 120                 125

Thr Pro Pro Phe Thr Lys Ala Leu Phe Thr Tyr Val Lys Glu Arg Lys
130                 135                 140

Tyr Thr Phe Cys Thr Pro Gly His Met Gly Gly Thr Ala Tyr Gln Lys
145                 150                 155                 160

Ser Pro Val Gly Cys Leu Phe Tyr Asp Phe Phe Gly Gly Asn Thr Leu
                165                 170                 175

Lys Ala Asp Val Ser Ile Ser Val Thr Glu Leu Gly Ser Leu Leu Asp
            180                 185                 190

His Thr Gly Pro His Leu Glu Ala Glu Glu Tyr Ile Ala Arg Thr Phe
        195                 200                 205

Gly Ala Glu Gln Ser Tyr Ile Val Thr Asn Gly Thr Ser Thr Ser Asn
210                 215                 220

Lys Ile Val Gly Met Tyr Ala Ala Pro Ser Gly Ser Thr Leu Leu Ile
225                 230                 235                 240

Asp Arg Asn Cys His Lys Ser Leu Ala His Leu Leu Met Met Asn Asp
                245                 250                 255

Val Val Pro Val Trp Leu Lys Pro Thr Arg Asn Ala Leu Gly Ile Leu
            260                 265                 270

Gly Gly Ile Pro Arg Arg Glu Phe Thr Arg Asp Ser Ile Glu Glu Lys
        275                 280                 285

Val Ala Ala Thr Thr Gln Ala Gln Trp Pro Val His Ala Val Ile Thr
290                 295                 300

Asn Ser Thr Tyr Asp Gly Leu Leu Tyr Asn Thr Asp Trp Ile Lys Gln
305                 310                 315                 320

Thr Leu Asp Val Pro Ser Ile His Phe Asp Ser Ala Trp Val Pro Tyr
                325                 330                 335

Thr His Phe His Pro Ile Tyr Gln Gly Lys Ser Gly Met Ser Gly Glu
            340                 345                 350

Arg Val Ala Gly Lys Val Ile Phe Glu Thr Gln Ser Thr His Lys Met
        355                 360                 365

Leu Ala Ala Leu Ser Gln Ala Ser Leu Ile His Ile Lys Gly Glu Tyr
370                 375                 380

Asp Glu Glu Ala Phe Asn Glu Ala Phe Met Met His Thr Thr Thr Ser
385                 390                 395                 400

Pro Ser Tyr Pro Ile Val Ala Ser Val Glu Thr Ala Ala Ala Met Leu
                405                 410                 415

Arg Gly Asn Pro Gly Lys Arg Leu Ile Asn Arg Ser Val Glu Arg Ala
            420                 425                 430

Leu His Phe Arg Lys Glu Val Gln Arg Leu Arg Glu Glu Ser Asp Gly
        435                 440                 445

Trp Phe Phe Asp Ile Trp Gln Pro Gln Val Asp Glu Ala Glu Cys
450                 455                 460

Trp Pro Val Ala Pro Gly Glu Gln Trp His Gly Phe Asn Asp Ala Asp
465                 470                 475                 480
```

```
Ala Asp His Met Phe Leu Asp Pro Val Lys Val Thr Ile Leu Thr Pro
            485                 490                 495
Gly Met Asp Glu Gln Gly Asn Met Ser Glu Glu Gly Ile Pro Ala Ala
        500                 505                 510
Leu Val Ala Lys Phe Leu Asp Glu Arg Gly Ile Val Glu Lys Thr
        515                 520                 525
Gly Pro Tyr Asn Leu Leu Phe Leu Phe Ser Ile Gly Ile Asp Lys Thr
    530                 535                 540
Lys Ala Met Gly Leu Leu Arg Gly Leu Thr Glu Phe Lys Arg Ser Tyr
545                 550                 555                 560
Asp Leu Asn Leu Arg Ile Lys Asn Met Leu Pro Asp Leu Tyr Ala Glu
                565                 570                 575
Asp Pro Asp Phe Tyr Arg Asn Met Arg Ile Gln Asp Leu Ala Gln Gly
            580                 585                 590
Ile His Lys Leu Ile Arg Lys His Asp Leu Pro Gly Leu Met Leu Arg
        595                 600                 605
Ala Phe Asp Thr Leu Pro Glu Met Ile Met Thr Pro His Gln Ala Trp
        610                 615                 620
Gln Arg Gln Ile Lys Gly Glu Val Glu Thr Ile Ala Leu Glu Gln Leu
625                 630                 635                 640
Val Gly Arg Val Ser Ala Asn Met Ile Leu Pro Tyr Pro Pro Gly Val
                645                 650                 655
Pro Leu Leu Met Pro Gly Glu Met Leu Thr Lys Glu Ser Arg Thr Val
            660                 665                 670
Leu Asp Phe Leu Leu Met Leu Cys Ser Val Gly Gln His Tyr Pro Gly
        675                 680                 685
Phe Glu Thr Asp Ile His Gly Ala Lys Gln Asp Glu Asp Gly Val Tyr
        690                 695                 700
Arg Val Arg Val Leu Lys Met Ala Gly
705                 710

<210> SEQ ID NO 46
<211> LENGTH: 603
<212> TYPE: DNA
<213> ORGANISM: Escherichia coli
<220> FEATURE:
<221> NAME/KEY: CDS
<222> LOCATION: (1)..(603)
<223> OTHER INFORMATION: fimB

<400> SEQUENCE: 46 atg aag aat aag gct gat aac aaa aaa agg aac ttc ctg acc cat agt      48
Met Lys Asn Lys Ala Asp Asn Lys Lys Arg Asn Phe Leu Thr His Ser
1               5                   10                  15 gaa atc gaa tca ctc ctt aaa gca gca aat acc ggg cct cat gca gca      96
Glu Ile Glu Ser Leu Leu Lys Ala Ala Asn Thr Gly Pro His Ala Ala
            20                  25                  30 cgt aat tat tgt ctg act ttg ctt tgt ttt att cat ggt ttc cgg gcg     144
Arg Asn Tyr Cys Leu Thr Leu Leu Cys Phe Ile His Gly Phe Arg Ala
        35                  40                  45 agt gaa att tgt cga ttg agg att tcg gat att gat ctt aag gca aag     192
Ser Glu Ile Cys Arg Leu Arg Ile Ser Asp Ile Asp Leu Lys Ala Lys
    50                  55                  60 tgt ata tat atc cat cga tta aaa aaa ggc ttt tca aca acg cac ccg     240
Cys Ile Tyr Ile His Arg Leu Lys Lys Gly Phe Ser Thr Thr His Pro
65                  70                  75                  80 cta ttg aat aaa gaa gtt cag gct tta aaa aac tgg ttg agt atc cgt     288
```

```
Leu Leu Asn Lys Glu Val Gln Ala Leu Lys Asn Trp Leu Ser Ile Arg
                85                  90                  95 act tcg tac ccg cat gct gag agc gag tgg gta ttt tta tca cgt aag      336
Thr Ser Tyr Pro His Ala Glu Ser Glu Trp Val Phe Leu Ser Arg Lys
            100                 105                 110 ggg aat ccg ctt tct cgg caa cag ttt tac cat att atc tcg act tcc      384
Gly Asn Pro Leu Ser Arg Gln Gln Phe Tyr His Ile Ile Ser Thr Ser
        115                 120                 125 ggt ggt aat gcc ggg ttg tca ctg gag att cat ccg cac atg tta cgc      432
Gly Gly Asn Ala Gly Leu Ser Leu Glu Ile His Pro His Met Leu Arg
130                 135                 140 cat tcg tgt ggt ttt gct ttg gcg aat atg gga ata gat acg cga ctt      480
His Ser Cys Gly Phe Ala Leu Ala Asn Met Gly Ile Asp Thr Arg Leu
145                 150                 155                 160 atc cag gat tat ctt ggg cat cgc aat att cgt cat act gtc tgg tat      528
Ile Gln Asp Tyr Leu Gly His Arg Asn Ile Arg His Thr Val Trp Tyr
                165                 170                 175 acc gcc agc aat gca ggg cgt ttt tac ggc atc tgg gat aga gcc aga      576
Thr Ala Ser Asn Ala Gly Arg Phe Tyr Gly Ile Trp Asp Arg Ala Arg
            180                 185                 190 gga cga cag cgt cac gct gtt tta tag                                  603
Gly Arg Gln Arg His Ala Val Leu
        195                 200

<210> SEQ ID NO 47
<211> LENGTH: 200
<212> TYPE: PRT
<213> ORGANISM: Escherichia coli

<400> SEQUENCE: 47

Met Lys Asn Lys Ala Asp Asn Lys Lys Arg Asn Phe Leu Thr His Ser
1               5                   10                  15

Glu Ile Glu Ser Leu Leu Lys Ala Ala Asn Thr Gly Pro His Ala Ala
            20                  25                  30

Arg Asn Tyr Cys Leu Thr Leu Leu Cys Phe Ile His Gly Phe Arg Ala
        35                  40                  45

Ser Glu Ile Cys Arg Leu Arg Ile Ser Asp Ile Asp Leu Lys Ala Lys
    50                  55                  60

Cys Ile Tyr Ile His Arg Leu Lys Lys Gly Phe Ser Thr Thr His Pro
65                  70                  75                  80

Leu Leu Asn Lys Glu Val Gln Ala Leu Lys Asn Trp Leu Ser Ile Arg
                85                  90                  95

Thr Ser Tyr Pro His Ala Glu Ser Glu Trp Val Phe Leu Ser Arg Lys
            100                 105                 110

Gly Asn Pro Leu Ser Arg Gln Gln Phe Tyr His Ile Ile Ser Thr Ser
        115                 120                 125

Gly Gly Asn Ala Gly Leu Ser Leu Glu Ile His Pro His Met Leu Arg
130                 135                 140

His Ser Cys Gly Phe Ala Leu Ala Asn Met Gly Ile Asp Thr Arg Leu
145                 150                 155                 160

Ile Gln Asp Tyr Leu Gly His Arg Asn Ile Arg His Thr Val Trp Tyr
                165                 170                 175

Thr Ala Ser Asn Ala Gly Arg Phe Tyr Gly Ile Trp Asp Arg Ala Arg
            180                 185                 190

Gly Arg Gln Arg His Ala Val Leu
        195                 200
```

-continued

```
<210> SEQ ID NO 48
<211> LENGTH: 597
<212> TYPE: DNA
<213> ORGANISM: Escherichia coli
<220> FEATURE:
<221> NAME/KEY: CDS
<222> LOCATION: (1)..(597)
<223> OTHER INFORMATION: fimE

<400> SEQUENCE: 48 gtg agt aaa cgt cgt tat ctt acc ggt aaa gaa gtt cag gcc atg atg     48
Val Ser Lys Arg Arg Tyr Leu Thr Gly Lys Glu Val Gln Ala Met Met
 1               5                  10                  15 cag gcg gtt tgt tac ggg gca acg gga gcc aga gat tat tgt ctt att     96
Gln Ala Val Cys Tyr Gly Ala Thr Gly Ala Arg Asp Tyr Cys Leu Ile
            20                  25                  30 ctg ttg gca tat cgg cat ggg atg cgt att agt gaa ctg ctt gat ctg    144
Leu Leu Ala Tyr Arg His Gly Met Arg Ile Ser Glu Leu Leu Asp Leu
        35                  40                  45 cat tat cag gac ctt gac ctt aat gaa ggt aga ata aat att cgc cga    192
His Tyr Gln Asp Leu Asp Leu Asn Glu Gly Arg Ile Asn Ile Arg Arg
    50                  55                  60 ctg aag aac gga ttt tct acc gtt cac ccg tta cgt ttt gat gag cgt    240
Leu Lys Asn Gly Phe Ser Thr Val His Pro Leu Arg Phe Asp Glu Arg
65                  70                  75                  80 gaa gcc gtg gaa cgc tgg acc cag gaa cgt gct aac tgg aaa ggc gct    288
Glu Ala Val Glu Arg Trp Thr Gln Glu Arg Ala Asn Trp Lys Gly Ala
                85                  90                  95 gac cgg act gac gct ata ttt att tct cgc cgc ggg agt cgg ctt tct    336
Asp Arg Thr Asp Ala Ile Phe Ile Ser Arg Arg Gly Ser Arg Leu Ser
            100                 105                 110 cgc cag cag gcc tat cgc att att cgc gat gcc ggt att gaa gct gga    384
Arg Gln Gln Ala Tyr Arg Ile Ile Arg Asp Ala Gly Ile Glu Ala Gly
        115                 120                 125 acc gta acg cag act cat cct cat atg tta agg cat gct tgc ggt tat    432
Thr Val Thr Gln Thr His Pro His Met Leu Arg His Ala Cys Gly Tyr
    130                 135                 140 gaa ttg gcg gag cgt ggt gca gat act cgt tta att cag gat tat ctc    480
Glu Leu Ala Glu Arg Gly Ala Asp Thr Arg Leu Ile Gln Asp Tyr Leu
145                 150                 155                 160 ggg cat cga aat att cgc cat act gtg cgt tat acc gcc agt aat gct    528
Gly His Arg Asn Ile Arg His Thr Val Arg Tyr Thr Ala Ser Asn Ala
                165                 170                 175 gct cgt ttt gcc gga tta tgg gaa aga aat aat ctc ata aac gaa aaa    576
Ala Arg Phe Ala Gly Leu Trp Glu Arg Asn Asn Leu Ile Asn Glu Lys
            180                 185                 190 tta aaa aga gaa gag gtt tga                                        597
Leu Lys Arg Glu Glu Val
        195

<210> SEQ ID NO 49
<211> LENGTH: 198
<212> TYPE: PRT
<213> ORGANISM: Escherichia coli

<400> SEQUENCE: 49

Val Ser Lys Arg Arg Tyr Leu Thr Gly Lys Glu Val Gln Ala Met Met
 1               5                  10                  15

Gln Ala Val Cys Tyr Gly Ala Thr Gly Ala Arg Asp Tyr Cys Leu Ile
            20                  25                  30

Leu Leu Ala Tyr Arg His Gly Met Arg Ile Ser Glu Leu Leu Asp Leu
        35                  40                  45
```

```
His Tyr Gln Asp Leu Asp Leu Asn Glu Gly Arg Ile Asn Ile Arg Arg
     50                  55                  60

Leu Lys Asn Gly Phe Ser Thr Val His Pro Leu Arg Phe Asp Glu Arg
 65                  70                  75                  80

Glu Ala Val Glu Arg Trp Thr Gln Glu Arg Ala Asn Trp Lys Gly Ala
                 85                  90                  95

Asp Arg Thr Asp Ala Ile Phe Ile Ser Arg Arg Gly Ser Arg Leu Ser
            100                 105                 110

Arg Gln Gln Ala Tyr Arg Ile Ile Arg Asp Ala Gly Ile Glu Ala Gly
        115                 120                 125

Thr Val Thr Gln Thr His Pro His Met Leu Arg His Ala Cys Gly Tyr
130                 135                 140

Glu Leu Ala Glu Arg Gly Ala Asp Thr Arg Leu Ile Gln Asp Tyr Leu
145                 150                 155                 160

Gly His Arg Asn Ile Arg His Thr Val Arg Tyr Thr Ala Ser Asn Ala
                165                 170                 175

Ala Arg Phe Ala Gly Leu Trp Glu Arg Asn Asn Leu Ile Asn Glu Lys
            180                 185                 190

Leu Lys Arg Glu Glu Val
        195

<210> SEQ ID NO 50
<211> LENGTH: 549
<212> TYPE: DNA
<213> ORGANISM: Escherichia coli
<220> FEATURE:
<221> NAME/KEY: CDS
<222> LOCATION: (1)..(549)
<223> OTHER INFORMATION: fimA

<400> SEQUENCE: 50 atg aaa att aaa act ctg gca atc gtt gtt ctg tcg gct ctg tcc ctc     48
Met Lys Ile Lys Thr Leu Ala Ile Val Val Leu Ser Ala Leu Ser Leu
 1               5                  10                  15 agt tct aca gcg gct ctg gcc gct gcc acg acg gtt aat ggt ggg acc     96
Ser Ser Thr Ala Ala Leu Ala Ala Ala Thr Thr Val Asn Gly Gly Thr
             20                  25                  30 gtt cac ttt aaa ggg gaa gtt gtt aac gcc gct tgc gca gtt gat gca    144
Val His Phe Lys Gly Glu Val Val Asn Ala Ala Cys Ala Val Asp Ala
         35                  40                  45 ggc tct gtt gat caa acc gtt cag tta gga cag gtt cgt acc gca tcg    192
Gly Ser Val Asp Gln Thr Val Gln Leu Gly Gln Val Arg Thr Ala Ser
     50                  55                  60 ctg gca cag gaa gga gca acc agt tct gct gtc ggt ttt aac att cag    240
Leu Ala Gln Glu Gly Ala Thr Ser Ser Ala Val Gly Phe Asn Ile Gln
 65                  70                  75                  80 ctg aat gat tgc gat acc aat gtt gca tct aaa gcc gct gtt gcc ttt    288
Leu Asn Asp Cys Asp Thr Asn Val Ala Ser Lys Ala Ala Val Ala Phe
                 85                  90                  95 tta ggt acg gcg att gat gcg ggt cat acc aac gtt ctg gct ctg cag    336
Leu Gly Thr Ala Ile Asp Ala Gly His Thr Asn Val Leu Ala Leu Gln
            100                 105                 110 agt tca gct gcg ggt agc gca aca aac gtt ggt gtg cag atc ctg gac    384
Ser Ser Ala Ala Gly Ser Ala Thr Asn Val Gly Val Gln Ile Leu Asp
        115                 120                 125 aga acg ggt gct gcg ctg acg ctg gat ggt gcg aca ttt agt tca gaa    432
Arg Thr Gly Ala Ala Leu Thr Leu Asp Gly Ala Thr Phe Ser Ser Glu
130                 135                 140
```

```
aca acc ctg aat aac gga acc aat acc att ccg ttc cag gcg cgt tat        480
Thr Thr Leu Asn Asn Gly Thr Asn Thr Ile Pro Phe Gln Ala Arg Tyr
145                 150                 155                 160 ttt gca acc ggg gcc gca acc ccg ggt gct gct aat gcg gat gcg acc        528
Phe Ala Thr Gly Ala Ala Thr Pro Gly Ala Ala Asn Ala Asp Ala Thr
                165                 170                 175 ttc aag gtt cag tat caa taa                                            549
Phe Lys Val Gln Tyr Gln
            180
```

<210> SEQ ID NO 51
<211> LENGTH: 182
<212> TYPE: PRT
<213> ORGANISM: Escherichia coli

<400> SEQUENCE: 51

```
Met Lys Ile Lys Thr Leu Ala Ile Val Val Leu Ser Ala Leu Ser Leu
1               5                   10                  15

Ser Ser Thr Ala Ala Leu Ala Ala Ala Thr Thr Val Asn Gly Gly Thr
                20                  25                  30

Val His Phe Lys Gly Glu Val Val Asn Ala Ala Cys Ala Val Asp Ala
            35                  40                  45

Gly Ser Val Asp Gln Thr Val Gln Leu Gly Gln Val Arg Thr Ala Ser
        50                  55                  60

Leu Ala Gln Glu Gly Ala Thr Ser Ser Ala Val Gly Phe Asn Ile Gln
65                  70                  75                  80

Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
        115                 120                 125

Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Thr Gly Ala Ala Thr Pro Gly Ala Ala Asn Ala Asp Ala Thr
                165                 170                 175

Phe Lys Val Gln Tyr Gln
            180
```

<210> SEQ ID NO 52
<211> LENGTH: 648
<212> TYPE: DNA
<213> ORGANISM: Escherichia coli
<220> FEATURE:
<221> NAME/KEY: CDS
<222> LOCATION: (1)..(648)
<223> OTHER INFORMATION: fimI

<400> SEQUENCE: 52

```
gtg ctg cta atg cgg atg cga cct tca agg ttc agt atc aat aac cta        48
Val Leu Leu Met Arg Met Arg Pro Ser Arg Phe Ser Ile Asn Asn Leu
1               5                   10                  15 ccc agg ttc agg gac gtc att acg ggc agg gat gcc cac cct tgt gcg        96
Pro Arg Phe Arg Asp Val Ile Thr Gly Arg Asp Ala His Pro Cys Ala
                20                  25                  30 ata aaa ata acg atg aaa agg aag aga tta ttt cta tta gcg tcg ttg       144
Ile Lys Ile Thr Met Lys Arg Lys Arg Leu Phe Leu Leu Ala Ser Leu
            35                  40                  45
```

```
ctg cca atg ttt gct ctg gcc gga aat aaa tgg aat acc acg ttg ccc        192
Leu Pro Met Phe Ala Leu Ala Gly Asn Lys Trp Asn Thr Thr Leu Pro
    50                  55                  60 ggc gga aat atg caa ttt cag ggc gtc att att gcg gaa act tgc cgg        240
Gly Gly Asn Met Gln Phe Gln Gly Val Ile Ile Ala Glu Thr Cys Arg
65                  70                  75                  80 att gaa gcc ggt gat aaa caa atg acg gtc aat atg ggg caa atc agc        288
Ile Glu Ala Gly Asp Lys Gln Met Thr Val Asn Met Gly Gln Ile Ser
                85                  90                  95 agt aac cgg ttt cat gcg gtt ggg gaa gat agc gca ccg gtg cct ttt        336
Ser Asn Arg Phe His Ala Val Gly Glu Asp Ser Ala Pro Val Pro Phe
            100                 105                 110 gtt att cat tta cgg gaa tgt agc acg gtg gtg agt gaa cgt gta ggt        384
Val Ile His Leu Arg Glu Cys Ser Thr Val Val Ser Glu Arg Val Gly
        115                 120                 125 gtg gcg ttt cac ggt gtc gcg gat ggt aaa aat ccg gat gtg ctt tcc        432
Val Ala Phe His Gly Val Ala Asp Gly Lys Asn Pro Asp Val Leu Ser
130                 135                 140 gtg gga gag ggg cca ggg ata gcc acc aat att ggc gta gcg ttg ttt        480
Val Gly Glu Gly Pro Gly Ile Ala Thr Asn Ile Gly Val Ala Leu Phe
145                 150                 155                 160 gat gat gaa gga aac ctc gta ccg att aat cgt cct cca gca aac tgg        528
Asp Asp Glu Gly Asn Leu Val Pro Ile Asn Arg Pro Pro Ala Asn Trp
                165                 170                 175 aaa cgg ctt tat tca ggc tct act tcg cta cat ttc atc gcc aaa tat        576
Lys Arg Leu Tyr Ser Gly Ser Thr Ser Leu His Phe Ile Ala Lys Tyr
            180                 185                 190 cgt gct acc ggg cgt cgg gtt act ggc ggc atc gcc aat gcc cag gcc        624
Arg Ala Thr Gly Arg Arg Val Thr Gly Gly Ile Ala Asn Ala Gln Ala
        195                 200                 205 tgg ttc tct tta acc tat cag taa                                        648
Trp Phe Ser Leu Thr Tyr Gln
    210                 215

<210> SEQ ID NO 53
<211> LENGTH: 215
<212> TYPE: PRT
<213> ORGANISM: Escherichia coli

<400> SEQUENCE: 53

Val Leu Leu Met Arg Met Arg Pro Ser Arg Phe Ser Ile Asn Asn Leu
1               5                   10                  15

Pro Arg Phe Arg Asp Val Ile Thr Gly Arg Asp Ala His Pro Cys Ala
            20                  25                  30

Ile Lys Ile Thr Met Lys Arg Lys Arg Leu Phe Leu Leu Ala Ser Leu
        35                  40                  45

Leu Pro Met Phe Ala Leu Ala Gly Asn Lys Trp Asn Thr Thr Leu Pro
    50                  55                  60

Gly Gly Asn Met Gln Phe Gln Gly Val Ile Ile Ala Glu Thr Cys Arg
65                  70                  75                  80

Ile Glu Ala Gly Asp Lys Gln Met Thr Val Asn Met Gly Gln Ile Ser
                85                  90                  95

Ser Asn Arg Phe His Ala Val Gly Glu Asp Ser Ala Pro Val Pro Phe
            100                 105                 110

Val Ile His Leu Arg Glu Cys Ser Thr Val Val Ser Glu Arg Val Gly
        115                 120                 125

Val Ala Phe His Gly Val Ala Asp Gly Lys Asn Pro Asp Val Leu Ser
130                 135                 140
```

Val Gly Glu Gly Pro Gly Ile Ala Thr Asn Ile Gly Val Ala Leu Phe
145                 150                 155                 160

Asp Asp Glu Gly Asn Leu Val Pro Ile Asn Arg Pro Pro Ala Asn Trp
                165                 170                 175

Lys Arg Leu Tyr Ser Gly Ser Thr Ser Leu His Phe Ile Ala Lys Tyr
            180                 185                 190

Arg Ala Thr Gly Arg Arg Val Thr Gly Gly Ile Ala Asn Ala Gln Ala
        195                 200                 205

Trp Phe Ser Leu Thr Tyr Gln
    210                 215

<210> SEQ ID NO 54
<211> LENGTH: 726
<212> TYPE: DNA
<213> ORGANISM: Escherichia coli
<220> FEATURE:
<221> NAME/KEY: CDS
<222> LOCATION: (1)..(726)
<223> OTHER INFORMATION: fimC

<400> SEQUENCE: 54

| gtg agt aat aaa aac gtc aat gta agg aaa tcg cag gaa ata aca ttc | 48 |
| Val Ser Asn Lys Asn Val Asn Val Arg Lys Ser Gln Glu Ile Thr Phe | |
| 1               5                   10                  15     | |

| tgc ttg ctg gca ggt atc ctg atg ttc atg gca atg atg gtt gcc gga | 96 |
| Cys Leu Leu Ala Gly Ile Leu Met Phe Met Ala Met Met Val Ala Gly | |
|             20                  25                  30         | |

| cgc gct gaa gcg gga gtg gcc tta ggt gcg act cgc gta att tat ccg | 144 |
| Arg Ala Glu Ala Gly Val Ala Leu Gly Ala Thr Arg Val Ile Tyr Pro | |
|         35                  40                  45             | |

| gca ggg caa aaa caa gag caa ctt gcc gtg aca aat aat gat gaa aat | 192 |
| Ala Gly Gln Lys Gln Glu Gln Leu Ala Val Thr Asn Asn Asp Glu Asn | |
|     50                  55                  60                 | |

| agt acc tat tta att caa tca tgg gtg gaa aat gcc gat ggt gta aag | 240 |
| Ser Thr Tyr Leu Ile Gln Ser Trp Val Glu Asn Ala Asp Gly Val Lys | |
| 65                  70                  75                  80 | |

| gat ggt cgt ttt atc gtg acg cct cct ctg ttt gcg atg aag gga aaa | 288 |
| Asp Gly Arg Phe Ile Val Thr Pro Pro Leu Phe Ala Met Lys Gly Lys | |
|                 85                  90                  95     | |

| aaa gag aat acc tta cgt att ctt gat gca aca aat aac caa ttg cca | 336 |
| Lys Glu Asn Thr Leu Arg Ile Leu Asp Ala Thr Asn Asn Gln Leu Pro | |
|             100                 105                 110        | |

| cag gac cgg gaa agt tta ttc tgg atg aac gtt aaa gcg att ccg tca | 384 |
| Gln Asp Arg Glu Ser Leu Phe Trp Met Asn Val Lys Ala Ile Pro Ser | |
|         115                 120                 125            | |

| atg gat aaa tca aaa ttg act gag aat acg cta cag ctc gca att atc | 432 |
| Met Asp Lys Ser Lys Leu Thr Glu Asn Thr Leu Gln Leu Ala Ile Ile | |
|     130                 135                 140                | |

| agc cgc att aaa ctg tac tat cgc ccg gct aaa tta gcg ttg cca ccc | 480 |
| Ser Arg Ile Lys Leu Tyr Tyr Arg Pro Ala Lys Leu Ala Leu Pro Pro | |
| 145                 150                 155                 160| |

| gat cag gcc gca gaa aaa tta aga ttt cgt cgt agc gcg aat tct ctg | 528 |
| Asp Gln Ala Ala Glu Lys Leu Arg Phe Arg Arg Ser Ala Asn Ser Leu | |
|                 165                 170                 175    | |

| acg ctg att aac ccg aca ccc tat tac ctg acg gta aca gag ttg aat | 576 |
| Thr Leu Ile Asn Pro Thr Pro Tyr Tyr Leu Thr Val Thr Glu Leu Asn | |
|             180                 185                 190        | |

| gcc gga acc cgg gtt ctt gaa aat gca ttg gtg cct cca atg ggc gaa | 624 |
| Ala Gly Thr Arg Val Leu Glu Asn Ala Leu Val Pro Pro Met Gly Glu | |
|         195                 200                 205            | |

```
agc acg gtt aaa ttg cct tct gat gca gga agc aat att act tac cga    672
Ser Thr Val Lys Leu Pro Ser Asp Ala Gly Ser Asn Ile Thr Tyr Arg
    210                 215                 220 aca ata aat gat tat ggc gca ctt acc ccc aaa atg acg ggc gta atg    720
Thr Ile Asn Asp Tyr Gly Ala Leu Thr Pro Lys Met Thr Gly Val Met
225                 230                 235                 240 gaa taa                                                             726
Glu
```

<210> SEQ ID NO 55
<211> LENGTH: 241
<212> TYPE: PRT
<213> ORGANISM: Escherichia coli

<400> SEQUENCE: 55

```
Val Ser Asn Lys Asn Val Asn Val Arg Lys Ser Gln Glu Ile Thr Phe
1               5                   10                  15

Cys Leu Leu Ala Gly Ile Leu Met Phe Met Ala Met Met Val Ala Gly
                20                  25                  30

Arg Ala Glu Ala Gly Val Ala Leu Gly Ala Thr Arg Val Ile Tyr Pro
            35                  40                  45

Ala Gly Gln Lys Gln Glu Gln Leu Ala Val Thr Asn Asn Asp Glu Asn
        50                  55                  60

Ser Thr Tyr Leu Ile Gln Ser Trp Val Glu Asn Ala Asp Gly Val Lys
65                  70                  75                  80

Asp Gly Arg Phe Ile Val Thr Pro Pro Leu Phe Ala Met Lys Gly Lys
                85                  90                  95

Lys Glu Asn Thr Leu Arg Ile Leu Asp Ala Thr Asn Asn Gln Leu Pro
            100                 105                 110

Gln Asp Arg Glu Ser Leu Phe Trp Met Asn Val Lys Ala Ile Pro Ser
        115                 120                 125

Met Asp Lys Ser Lys Leu Thr Glu Asn Thr Leu Gln Leu Ala Ile Ile
130                 135                 140

Ser Arg Ile Lys Leu Tyr Tyr Arg Pro Ala Lys Leu Ala Leu Pro Pro
145                 150                 155                 160

Asp Gln Ala Ala Glu Lys Leu Arg Phe Arg Arg Ser Ala Asn Ser Leu
                165                 170                 175

Thr Leu Ile Asn Pro Thr Pro Tyr Tyr Leu Thr Val Thr Glu Leu Asn
            180                 185                 190

Ala Gly Thr Arg Val Leu Glu Asn Ala Leu Val Pro Pro Met Gly Glu
        195                 200                 205

Ser Thr Val Lys Leu Pro Ser Asp Ala Gly Ser Asn Ile Thr Tyr Arg
    210                 215                 220

Thr Ile Asn Asp Tyr Gly Ala Leu Thr Pro Lys Met Thr Gly Val Met
225                 230                 235                 240

Glu
```

<210> SEQ ID NO 56
<211> LENGTH: 2637
<212> TYPE: DNA
<213> ORGANISM: Escherichia coli
<220> FEATURE:
<221> NAME/KEY: CDS
<222> LOCATION: (1)..(2637)
<223> OTHER INFORMATION: fimD

<400> SEQUENCE: 56

```
atg tca tat ctg aat tta aga ctt tac cag cga aac aca caa tgc ttg      48
Met Ser Tyr Leu Asn Leu Arg Leu Tyr Gln Arg Asn Thr Gln Cys Leu
1               5                   10                  15 cat att cgt aag cat cgt ttg gct ggt ttt ttt gtc cga ctc gtt gtc      96
His Ile Arg Lys His Arg Leu Ala Gly Phe Phe Val Arg Leu Val Val
            20                  25                  30 gcc tgt gct ttt gcc gca cag gca cct ttg tca tct gcc gac ctc tat     144
Ala Cys Ala Phe Ala Ala Gln Ala Pro Leu Ser Ser Ala Asp Leu Tyr
        35                  40                  45 ttt aat ccg cgc ttt tta gcg gat gat ccc cag gct gtg gcc gat tta     192
Phe Asn Pro Arg Phe Leu Ala Asp Asp Pro Gln Ala Val Ala Asp Leu
    50                  55                  60 tcg cgt ttt gaa aat ggg caa gaa tta ccg cca ggg acg tat cgc gtc     240
Ser Arg Phe Glu Asn Gly Gln Glu Leu Pro Pro Gly Thr Tyr Arg Val
65              70                  75                  80 gat atc tat ttg aat aat ggt tat atg gca acg cgt gat gtc aca ttt     288
Asp Ile Tyr Leu Asn Asn Gly Tyr Met Ala Thr Arg Asp Val Thr Phe
                85                  90                  95 aat acg ggc gac agt gaa caa ggg att gtt ccc tgc ctg aca cgc gcg     336
Asn Thr Gly Asp Ser Glu Gln Gly Ile Val Pro Cys Leu Thr Arg Ala
            100                 105                 110 caa ctc gcc agt atg ggg ctg aat acg gct tct gtc gcc ggt atg aat     384
Gln Leu Ala Ser Met Gly Leu Asn Thr Ala Ser Val Ala Gly Met Asn
        115                 120                 125 ctg ctg gcg gat gat gcc tgt gtg cca tta acc aca atg gtc cag gac     432
Leu Leu Ala Asp Asp Ala Cys Val Pro Leu Thr Thr Met Val Gln Asp
    130                 135                 140 gct act gcg cat ctg gat gtt ggt cag cag cga ctg aac ctg acg atc     480
Ala Thr Ala His Leu Asp Val Gly Gln Gln Arg Leu Asn Leu Thr Ile
145                 150                 155                 160 cct cag gca ttt atg agt aat cgc gcg cgt ggt tat att cct cct gag     528
Pro Gln Ala Phe Met Ser Asn Arg Ala Arg Gly Tyr Ile Pro Pro Glu
                165                 170                 175 tta tgg gat ccc ggt att aat gcc gga ttg ctc aat tat aat ttc agc     576
Leu Trp Asp Pro Gly Ile Asn Ala Gly Leu Leu Asn Tyr Asn Phe Ser
            180                 185                 190 gga aat agt gta cag aat cgg att ggg ggt aac agc cat tat gca tat     624
Gly Asn Ser Val Gln Asn Arg Ile Gly Gly Asn Ser His Tyr Ala Tyr
        195                 200                 205 tta aac cta cag agt ggg tta aat att ggt gcg tgg cgt tta cgc gac     672
Leu Asn Leu Gln Ser Gly Leu Asn Ile Gly Ala Trp Arg Leu Arg Asp
    210                 215                 220 aat acc acc tgg agt tat aac agt agc gac aga tca tca ggt agc aaa     720
Asn Thr Thr Trp Ser Tyr Asn Ser Ser Asp Arg Ser Ser Gly Ser Lys
225                 230                 235                 240 aat aaa tgg cag cat atc aat acc tgg ctt gag cga gac ata ata ccg     768
Asn Lys Trp Gln His Ile Asn Thr Trp Leu Glu Arg Asp Ile Ile Pro
                245                 250                 255 tta cgt tcc cgg ctg acg ctg ggt gat ggt tat act cag ggc gat att     816
Leu Arg Ser Arg Leu Thr Leu Gly Asp Gly Tyr Thr Gln Gly Asp Ile
            260                 265                 270 ttc gat ggt att aac ttt cgc ggc gca caa ttg gcc tca gat gac aat     864
Phe Asp Gly Ile Asn Phe Arg Gly Ala Gln Leu Ala Ser Asp Asp Asn
        275                 280                 285 atg tta ccc gat agt caa aga gga ttt gcc ccg gtg atc cac ggt att     912
Met Leu Pro Asp Ser Gln Arg Gly Phe Ala Pro Val Ile His Gly Ile
    290                 295                 300 gct cgt ggt act gca cag gtc act att aaa caa aat ggg tat gac att     960
Ala Arg Gly Thr Ala Gln Val Thr Ile Lys Gln Asn Gly Tyr Asp Ile
305                 310                 315                 320
```

```
                                                          -continued tat aat agt acg gtg cca ccg ggg cct ttt acc atc aac gat atc tat      1008
Tyr Asn Ser Thr Val Pro Pro Gly Pro Phe Thr Ile Asn Asp Ile Tyr
                325                 330                 335 gcc gca ggt aat agt ggt gac ttg cag gta acg atc aaa gag gct gac      1056
Ala Ala Gly Asn Ser Gly Asp Leu Gln Val Thr Ile Lys Glu Ala Asp
        340                 345                 350 ggc agc acg cag att ttt acc gta ccc tat tcg tca gtc ccg ctt ttg      1104
Gly Ser Thr Gln Ile Phe Thr Val Pro Tyr Ser Ser Val Pro Leu Leu
355                 360                 365 caa cgt gaa ggg cat act cgt tat tcc att acg gca gga gaa tac cgt      1152
Gln Arg Glu Gly His Thr Arg Tyr Ser Ile Thr Ala Gly Glu Tyr Arg
    370                 375                 380 agt gga aat gcg cag cag gaa aaa acc cgc ttt ttc cag agt aca tta      1200
Ser Gly Asn Ala Gln Gln Glu Lys Thr Arg Phe Phe Gln Ser Thr Leu
385                 390                 395                 400 ctc cac ggc ctt ccg gct ggc tgg aca ata tat ggt gga acg caa ctg      1248
Leu His Gly Leu Pro Ala Gly Trp Thr Ile Tyr Gly Gly Thr Gln Leu
                405                 410                 415 gcg gat cgt tat cgt gct ttt aat ttc ggt atc ggg aaa aac atg ggg      1296
Ala Asp Arg Tyr Arg Ala Phe Asn Phe Gly Ile Gly Lys Asn Met Gly
        420                 425                 430 gca ctg ggc gct ctg tct gtg gat atg acg cag gct aat tcc aca ctt      1344
Ala Leu Gly Ala Leu Ser Val Asp Met Thr Gln Ala Asn Ser Thr Leu
435                 440                 445 ccc gat gac agt cag cat gac gga caa tcg gtg cgt ttt ctc tat aac      1392
Pro Asp Asp Ser Gln His Asp Gly Gln Ser Val Arg Phe Leu Tyr Asn
    450                 455                 460 aaa tcg ctc aat gaa tca ggc acg aat att cag tta gtg ggt tac cgt      1440
Lys Ser Leu Asn Glu Ser Gly Thr Asn Ile Gln Leu Val Gly Tyr Arg
465                 470                 475                 480 tat tcg acc agc gga tat ttt aat ttc gct gat aca aca tac agt cga      1488
Tyr Ser Thr Ser Gly Tyr Phe Asn Phe Ala Asp Thr Thr Tyr Ser Arg
                485                 490                 495 atg aat ggc tac aac atc gaa aca cag gac gga gtt att cag gtt aag      1536
Met Asn Gly Tyr Asn Ile Glu Thr Gln Asp Gly Val Ile Gln Val Lys
        500                 505                 510 ccg aaa ttc acc gac tat tac aac ctc gct tat aac aaa cgc ggg aaa      1584
Pro Lys Phe Thr Asp Tyr Tyr Asn Leu Ala Tyr Asn Lys Arg Gly Lys
515                 520                 525 tta caa ctc acc gtt act cag caa ctc ggg cgc aca tca aca ctg tat      1632
Leu Gln Leu Thr Val Thr Gln Gln Leu Gly Arg Thr Ser Thr Leu Tyr
    530                 535                 540 ttg agt ggt agc cat caa act tat tgg gga acg agt aat gtc gat gag      1680
Leu Ser Gly Ser His Gln Thr Tyr Trp Gly Thr Ser Asn Val Asp Glu
545                 550                 555                 560 caa ttc cag gct gga tta aat act gcg ttc gaa gat atc aac tgg acg      1728
Gln Phe Gln Ala Gly Leu Asn Thr Ala Phe Glu Asp Ile Asn Trp Thr
                565                 570                 575 ctc agc tat agc ctg acg aaa aac gcc tgg caa aaa gga cgg gat cag      1776
Leu Ser Tyr Ser Leu Thr Lys Asn Ala Trp Gln Lys Gly Arg Asp Gln
        580                 585                 590 atg tta gcg ctt aac gtc aat att cct ttc agc cac tgg ctg cgt tct      1824
Met Leu Ala Leu Asn Val Asn Ile Pro Phe Ser His Trp Leu Arg Ser
595                 600                 605 gac agt aaa tct cag tgg cga cat gcc agt gcc agc tac agc atg tca      1872
Asp Ser Lys Ser Gln Trp Arg His Ala Ser Ala Ser Tyr Ser Met Ser
    610                 615                 620 cac gat ctc aac ggt cgg atg acc aat ctg gct ggt gta tac ggt acg      1920
His Asp Leu Asn Gly Arg Met Thr Asn Leu Ala Gly Val Tyr Gly Thr
```

```
                625                 630                 635                 640
ttg ctg gaa gac aac aac ctc agc tat agc gtg caa acc ggc tat gcc        1968
Leu Leu Glu Asp Asn Asn Leu Ser Tyr Ser Val Gln Thr Gly Tyr Ala
                        645                 650                 655 ggg gga ggc gat gga aat agc gga agt aca ggc tac gcc acg ctg aat        2016
Gly Gly Gly Asp Gly Asn Ser Gly Ser Thr Gly Tyr Ala Thr Leu Asn
            660                 665                 670 tat cgc ggt ggt tac ggc aat gcc aat atc ggt tac agc cat agc gat        2064
Tyr Arg Gly Gly Tyr Gly Asn Ala Asn Ile Gly Tyr Ser His Ser Asp
        675                 680                 685 gat att aag cag ctc tat tac gga gtc agc ggt ggg gta ctg gct cat        2112
Asp Ile Lys Gln Leu Tyr Tyr Gly Val Ser Gly Gly Val Leu Ala His
    690                 695                 700 gcc aat ggc gta acg ctg ggg cag ccg tta aac gat acg gtg gtg ctt        2160
Ala Asn Gly Val Thr Leu Gly Gln Pro Leu Asn Asp Thr Val Val Leu
705                 710                 715                 720 gtt aaa gcg cct ggc gca aaa gat gca aaa gtc gaa aac cag acg ggg        2208
Val Lys Ala Pro Gly Ala Lys Asp Ala Lys Val Glu Asn Gln Thr Gly
                    725                 730                 735 gtg cgt acc gac tgg cgt ggt tat gcc gtg ctg cct tat gcc act gaa        2256
Val Arg Thr Asp Trp Arg Gly Tyr Ala Val Leu Pro Tyr Ala Thr Glu
                740                 745                 750 tat cgg gaa aat aga gtg gcg ctg gat acc aat acc ctg gct gat aac        2304
Tyr Arg Glu Asn Arg Val Ala Leu Asp Thr Asn Thr Leu Ala Asp Asn
            755                 760                 765 gtc gat tta gat aac gcg gtt gct aac gtt gtt ccc act cgt ggg gcg        2352
Val Asp Leu Asp Asn Ala Val Ala Asn Val Val Pro Thr Arg Gly Ala
        770                 775                 780 atc gtg cga gca gag ttt aaa gcg cgc gtt ggg ata aaa ctg ctc atg        2400
Ile Val Arg Ala Glu Phe Lys Ala Arg Val Gly Ile Lys Leu Leu Met
785                 790                 795                 800 acg ctg acc cac aat aat aag ccg ctg ccg ttt ggg gcg atg gtg aca        2448
Thr Leu Thr His Asn Asn Lys Pro Leu Pro Phe Gly Ala Met Val Thr
                    805                 810                 815 tca gag agt agc cag agt agc ggc att gtt gcg gat aat ggt cag gtt        2496
Ser Glu Ser Ser Gln Ser Ser Gly Ile Val Ala Asp Asn Gly Gln Val
                820                 825                 830 tac ctc agc gga atg cct tta gcg gga aaa gtt cag gtg aaa tgg gga        2544
Tyr Leu Ser Gly Met Pro Leu Ala Gly Lys Val Gln Val Lys Trp Gly
            835                 840                 845 gaa gag gaa aat gct cac tgt gtc gcc aat tat caa ctg cca cca gag        2592
Glu Glu Glu Asn Ala His Cys Val Ala Asn Tyr Gln Leu Pro Pro Glu
        850                 855                 860 agt cag cag cag tta tta acc cag cta tca gct gaa tgt cgt taa            2637
Ser Gln Gln Gln Leu Leu Thr Gln Leu Ser Ala Glu Cys Arg
    865                 870                 875

SEQ ID NO 57

<211> LENGTH: 878
<212> TYPE: PRT
<213> ORGANISM: Escherichia coli

<400> SEQUENCE: 57

Met Ser Tyr Leu Asn Leu Arg Leu Tyr Gln Arg Asn Thr Gln Cys Leu
1               5                   10                  15

His Ile Arg Lys His Arg Leu Ala Gly Phe Phe Val Arg Leu Val Val
            20                  25                  30

Ala Cys Ala Phe Ala Ala Gln Ala Pro Leu Ser Ser Ala Asp Leu Tyr
        35                  40                  45
```

```
Phe Asn Pro Arg Phe Leu Ala Asp Asp Pro Gln Ala Val Ala Asp Leu
     50                  55                  60
Ser Arg Phe Glu Asn Gly Gln Glu Leu Pro Pro Gly Thr Tyr Arg Val
 65                  70                  75                  80
Asp Ile Tyr Leu Asn Asn Gly Tyr Met Ala Thr Arg Asp Val Thr Phe
                 85                  90                  95
Asn Thr Gly Asp Ser Glu Gln Gly Ile Val Pro Cys Leu Thr Arg Ala
            100                 105                 110
Gln Leu Ala Ser Met Gly Leu Asn Thr Ala Ser Val Ala Gly Met Asn
            115                 120                 125
Leu Leu Ala Asp Asp Ala Cys Val Pro Leu Thr Thr Met Val Gln Asp
130                 135                 140
Ala Thr Ala His Leu Asp Val Gly Gln Gln Arg Leu Asn Leu Thr Ile
145                 150                 155                 160
Pro Gln Ala Phe Met Ser Asn Arg Ala Arg Gly Tyr Ile Pro Pro Glu
                165                 170                 175
Leu Trp Asp Pro Gly Ile Asn Ala Gly Leu Leu Asn Tyr Asn Phe Ser
            180                 185                 190
Gly Asn Ser Val Gln Asn Arg Ile Gly Gly Asn Ser His Tyr Ala Tyr
            195                 200                 205
Leu Asn Leu Gln Ser Gly Leu Asn Ile Gly Ala Trp Arg Leu Arg Asp
            210                 215                 220
Asn Thr Thr Trp Ser Tyr Asn Ser Ser Asp Arg Ser Ser Gly Ser Lys
225                 230                 235                 240
Asn Lys Trp Gln His Ile Asn Thr Trp Leu Glu Arg Asp Ile Ile Pro
                245                 250                 255
Leu Arg Ser Arg Leu Thr Leu Gly Asp Gly Tyr Thr Gln Gly Asp Ile
            260                 265                 270
Phe Asp Gly Ile Asn Phe Arg Gly Ala Gln Leu Ala Ser Asp Asp Asn
            275                 280                 285
Met Leu Pro Asp Ser Gln Arg Gly Phe Ala Pro Val Ile His Gly Ile
290                 295                 300
Ala Arg Gly Thr Ala Gln Val Thr Ile Lys Gln Asn Gly Tyr Asp Ile
305                 310                 315                 320
Tyr Asn Ser Thr Val Pro Pro Gly Pro Phe Thr Ile Asn Asp Ile Tyr
                325                 330                 335
Ala Ala Gly Asn Ser Gly Asp Leu Gln Val Thr Ile Lys Glu Ala Asp
            340                 345                 350
Gly Ser Thr Gln Ile Phe Thr Val Pro Tyr Ser Ser Val Pro Leu Leu
            355                 360                 365
Gln Arg Glu Gly His Thr Arg Tyr Ser Ile Thr Ala Gly Glu Tyr Arg
370                 375                 380
Ser Gly Asn Ala Gln Gln Glu Lys Thr Arg Phe Phe Gln Ser Thr Leu
385                 390                 395                 400
Leu His Gly Leu Pro Ala Gly Trp Thr Ile Tyr Gly Gly Thr Gln Leu
                405                 410                 415
Ala Asp Arg Tyr Arg Ala Phe Asn Phe Gly Ile Gly Lys Asn Met Gly
            420                 425                 430
Ala Leu Gly Ala Leu Ser Val Asp Met Thr Gln Ala Asn Ser Thr Leu
            435                 440                 445
Pro Asp Asp Ser Gln His Asp Gly Gln Ser Val Arg Phe Leu Tyr Asn
450                 455                 460
```

```
Lys Ser Leu Asn Glu Ser Gly Thr Asn Ile Gln Leu Val Gly Tyr Arg
465                 470                 475                 480

Tyr Ser Thr Ser Gly Tyr Phe Asn Phe Ala Asp Thr Thr Tyr Ser Arg
                485                 490                 495

Met Asn Gly Tyr Asn Ile Glu Thr Gln Asp Gly Val Ile Gln Val Lys
                500                 505                 510

Pro Lys Phe Thr Asp Tyr Tyr Asn Leu Ala Tyr Asn Lys Arg Gly Lys
            515                 520                 525

Leu Gln Leu Thr Val Thr Gln Gln Leu Gly Arg Thr Ser Thr Leu Tyr
        530                 535                 540

Leu Ser Gly Ser His Gln Thr Tyr Trp Gly Thr Ser Asn Val Asp Glu
545                 550                 555                 560

Gln Phe Gln Ala Gly Leu Asn Thr Ala Phe Glu Asp Ile Asn Trp Thr
                565                 570                 575

Leu Ser Tyr Ser Leu Thr Lys Asn Ala Trp Gln Lys Gly Arg Asp Gln
                580                 585                 590

Met Leu Ala Leu Asn Val Asn Ile Pro Phe Ser His Trp Leu Arg Ser
            595                 600                 605

Asp Ser Lys Ser Gln Trp Arg His Ala Ser Ala Ser Tyr Ser Met Ser
        610                 615                 620

His Asp Leu Asn Gly Arg Met Thr Asn Leu Ala Gly Val Tyr Gly Thr
625                 630                 635                 640

Leu Leu Glu Asp Asn Asn Leu Ser Tyr Ser Val Gln Thr Gly Tyr Ala
                645                 650                 655

Gly Gly Gly Asp Gly Asn Ser Gly Ser Thr Gly Tyr Ala Thr Leu Asn
                660                 665                 670

Tyr Arg Gly Gly Tyr Gly Asn Ala Asn Ile Gly Tyr Ser His Ser Asp
            675                 680                 685

Asp Ile Lys Gln Leu Tyr Tyr Gly Val Ser Gly Gly Val Leu Ala His
        690                 695                 700

Ala Asn Gly Val Thr Leu Gly Gln Pro Leu Asn Asp Thr Val Val Leu
705                 710                 715                 720

Val Lys Ala Pro Gly Ala Lys Asp Ala Lys Val Glu Asn Gln Thr Gly
                725                 730                 735

Val Arg Thr Asp Trp Arg Gly Tyr Ala Val Leu Pro Tyr Ala Thr Glu
                740                 745                 750

Tyr Arg Glu Asn Arg Val Ala Leu Asp Thr Asn Thr Leu Ala Asp Asn
            755                 760                 765

Val Asp Leu Asp Asn Ala Val Ala Asn Val Val Pro Thr Arg Gly Ala
        770                 775                 780

Ile Val Arg Ala Glu Phe Lys Ala Arg Val Gly Ile Lys Leu Leu Met
785                 790                 795                 800

Thr Leu Thr His Asn Asn Lys Pro Leu Pro Phe Gly Ala Met Val Thr
                805                 810                 815

Ser Glu Ser Ser Gln Ser Ser Gly Ile Val Ala Asp Asn Gly Gln Val
                820                 825                 830

Tyr Leu Ser Gly Met Pro Leu Ala Gly Lys Val Gln Val Lys Trp Gly
            835                 840                 845

Glu Glu Glu Asn Ala His Cys Val Ala Asn Tyr Gln Leu Pro Pro Glu
        850                 855                 860

Ser Gln Gln Gln Leu Leu Thr Gln Leu Ser Ala Glu Cys Arg
865                 870                 875
```

<210> SEQ ID NO 58
<211> LENGTH: 531
<212> TYPE: DNA
<213> ORGANISM: Escherichia coli
<220> FEATURE:
<221> NAME/KEY: CDS
<222> LOCATION: (1)..(531)
<223> OTHER INFORMATION: fimF

<400> SEQUENCE: 58

```
atg aga aac aaa cct ttt tat ctt ctg tgc gct ttt ttg tgg ctg gcg      48
Met Arg Asn Lys Pro Phe Tyr Leu Leu Cys Ala Phe Leu Trp Leu Ala
1               5                   10                  15 gtg agt cac gct ttg gct gcg gat agc acg att act atc cgc ggc tat      96
Val Ser His Ala Leu Ala Ala Asp Ser Thr Ile Thr Ile Arg Gly Tyr
            20                  25                  30 gtc agg gat aac ggc tgt agt gtg gcc gct gaa tca acc aat ttt act     144
Val Arg Asp Asn Gly Cys Ser Val Ala Ala Glu Ser Thr Asn Phe Thr
        35                  40                  45 gtt gat ctg atg gaa aac gcg gcg aag caa ttt aac aac att ggc gcg     192
Val Asp Leu Met Glu Asn Ala Ala Lys Gln Phe Asn Asn Ile Gly Ala
    50                  55                  60 acg act cct gtt gtt cca ttt cgt att ttg ctg tca ccc tgt ggt aat     240
Thr Thr Pro Val Val Pro Phe Arg Ile Leu Leu Ser Pro Cys Gly Asn
65                  70                  75                  80 gcc gtt tct gcc gta aag gtt ggg ttt act ggc gtt gca gat agc cac     288
Ala Val Ser Ala Val Lys Val Gly Phe Thr Gly Val Ala Asp Ser His
                85                  90                  95 aat gcc aac ctg ctt gca ctt gaa aat acg gtg tca gcg gct tcg gga     336
Asn Ala Asn Leu Leu Ala Leu Glu Asn Thr Val Ser Ala Ala Ser Gly
            100                 105                 110 ctg gga ata cag ctt ctg aat gag cag caa aat caa ata ccc ctt aat     384
Leu Gly Ile Gln Leu Leu Asn Glu Gln Gln Asn Gln Ile Pro Leu Asn
        115                 120                 125 gct cca tcg tcc gcg ctt tcg tgg acg acc ctg acg ccg ggt aaa cca     432
Ala Pro Ser Ser Ala Leu Ser Trp Thr Thr Leu Thr Pro Gly Lys Pro
    130                 135                 140 aat acg ctg aat ttt tac gcc cgg cta atg gcg aca cag gtg cct gtc     480
Asn Thr Leu Asn Phe Tyr Ala Arg Leu Met Ala Thr Gln Val Pro Val
145                 150                 155                 160 act gcg ggg cat atc aat gcc acg gct acc ttc act ctt gaa tat cag     528
Thr Ala Gly His Ile Asn Ala Thr Ala Thr Phe Thr Leu Glu Tyr Gln
                165                 170                 175 taa                                                                  531
```

<210> SEQ ID NO 59
<211> LENGTH: 176
<212> TYPE: PRT
<213> ORGANISM: Escherichia coli

<400> SEQUENCE: 59

```
Met Arg Asn Lys Pro Phe Tyr Leu Leu Cys Ala Phe Leu Trp Leu Ala
1               5                   10                  15

Val Ser His Ala Leu Ala Ala Asp Ser Thr Ile Thr Ile Arg Gly Tyr
            20                  25                  30

Val Arg Asp Asn Gly Cys Ser Val Ala Ala Glu Ser Thr Asn Phe Thr
        35                  40                  45

Val Asp Leu Met Glu Asn Ala Ala Lys Gln Phe Asn Asn Ile Gly Ala
    50                  55                  60

Thr Thr Pro Val Val Pro Phe Arg Ile Leu Leu Ser Pro Cys Gly Asn
65                  70                  75                  80
```

```
Ala Val Ser Ala Val Lys Val Gly Phe Thr Gly Val Ala Asp Ser His
                85                  90                  95

Asn Ala Asn Leu Leu Ala Leu Glu Asn Thr Val Ser Ala Ala Ser Gly
            100                 105                 110

Leu Gly Ile Gln Leu Leu Asn Glu Gln Gln Asn Gln Ile Pro Leu Asn
        115                 120                 125

Ala Pro Ser Ser Ala Leu Ser Trp Thr Thr Leu Thr Pro Gly Lys Pro
    130                 135                 140

Asn Thr Leu Asn Phe Tyr Ala Arg Leu Met Ala Thr Gln Val Pro Val
145                 150                 155                 160

Thr Ala Gly His Ile Asn Ala Thr Ala Thr Phe Thr Leu Glu Tyr Gln
                165                 170                 175

<210> SEQ ID NO 60
<211> LENGTH: 504
<212> TYPE: DNA
<213> ORGANISM: Escherichia coli
<220> FEATURE:
<221> NAME/KEY: CDS
<222> LOCATION: (1)..(504)
<223> OTHER INFORMATION: fimG

<400> SEQUENCE: 60 atg aaa tgg tgc aaa cgt ggg tat gta ttg gcg gca ata ttg gcg ctc       48
Met Lys Trp Cys Lys Arg Gly Tyr Val Leu Ala Ala Ile Leu Ala Leu
1               5                   10                  15 gca agt gcg acg ata cag gca gcc gat gtc acc atc acg gtg aac ggt       96
Ala Ser Ala Thr Ile Gln Ala Ala Asp Val Thr Ile Thr Val Asn Gly
                20                  25                  30 aag gtc gtc gcc aaa ccg tgt acg gtt tcc acc acc aat gcc acg gtt      144
Lys Val Val Ala Lys Pro Cys Thr Val Ser Thr Thr Asn Ala Thr Val
            35                  40                  45 gat ctc ggc gat ctt tat tct ttc agt ctt atg tct gcc ggg gcg gca      192
Asp Leu Gly Asp Leu Tyr Ser Phe Ser Leu Met Ser Ala Gly Ala Ala
        50                  55                  60 tcg gcc tgg cat gat gtt gcg ctt gag ttg act aat tgt ccg gtg gga      240
Ser Ala Trp His Asp Val Ala Leu Glu Leu Thr Asn Cys Pro Val Gly
65                  70                  75                  80 acg tcg agg gtc act gcc agc ttc agc ggg gca gcc gac agt acc gga      288
Thr Ser Arg Val Thr Ala Ser Phe Ser Gly Ala Ala Asp Ser Thr Gly
                85                  90                  95 tat tat aaa aac cag ggg acc gcg caa aac atc cag tta gag cta cag      336
Tyr Tyr Lys Asn Gln Gly Thr Ala Gln Asn Ile Gln Leu Glu Leu Gln
            100                 105                 110 gat gac agt ggc aac aca ttg aat act ggc gca acc aaa aca gtt cag      384
Asp Asp Ser Gly Asn Thr Leu Asn Thr Gly Ala Thr Lys Thr Val Gln
        115                 120                 125 gtg gat gat tcc tca caa tca gcg cac ttc ccg tta cag gtc aga gca      432
Val Asp Asp Ser Ser Gln Ser Ala His Phe Pro Leu Gln Val Arg Ala
    130                 135                 140 ttg aca gta aat ggc gga gcc act cag gga acc att cag gca gtg att      480
Leu Thr Val Asn Gly Gly Ala Thr Gln Gly Thr Ile Gln Ala Val Ile
145                 150                 155                 160 agc atc acc tat acc tac agc tga                                      504
Ser Ile Thr Tyr Thr Tyr Ser
                165

<210> SEQ ID NO 61
<211> LENGTH: 167
<212> TYPE: PRT
```

```
-continued

<213> ORGANISM: Escherichia coli

<400> SEQUENCE: 61

Met Lys Trp Cys Lys Arg Gly Tyr Val Leu Ala Ala Ile Leu Ala Leu
1               5                   10                  15

Ala Ser Ala Thr Ile Gln Ala Ala Asp Val Thr Ile Thr Val Asn Gly
            20                  25                  30

Lys Val Val Ala Lys Pro Cys Thr Val Ser Thr Thr Asn Ala Thr Val
        35                  40                  45

Asp Leu Gly Asp Leu Tyr Ser Phe Ser Leu Met Ser Ala Gly Ala Ala
    50                  55                  60

Ser Ala Trp His Asp Val Ala Leu Glu Leu Thr Asn Cys Pro Val Gly
65                  70                  75                  80

Thr Ser Arg Val Thr Ala Ser Phe Ser Gly Ala Ala Asp Ser Thr Gly
            85                  90                  95

Tyr Tyr Lys Asn Gln Gly Thr Ala Gln Asn Ile Gln Leu Glu Leu Gln
            100                 105                 110

Asp Asp Ser Gly Asn Thr Leu Asn Thr Gly Ala Thr Lys Thr Val Gln
            115                 120                 125

Val Asp Asp Ser Ser Gln Ser Ala His Phe Pro Leu Gln Val Arg Ala
    130                 135                 140

Leu Thr Val Asn Gly Gly Ala Thr Gln Gly Thr Ile Gln Ala Val Ile
145                 150                 155                 160

Ser Ile Thr Tyr Thr Tyr Ser
                165
```

L-AMINO ACID PRODUCING MICROORGANISM WHICH HAS BEEN MODIFIED TO INACTIVE THE FIMH GENE, AND A METHOD FOR PRODUCING I-AMINO ACID

This application claims priority under 35 U.S.C. §119(a) to JP 2005-009826, filed on Jan. 18, 2005, and JP 2005-120222, filed on Apr. 18, 2005, and under 35 U.S.C. §119(e) to U.S. provisional applications 60/644,040 and 60/673,338, filed on Jan. 18, 2005 and Apr. 21, 2005 respectively, the entireties of all are hereby incorporated by reference. The Sequence Listing on Compact Disk filed herewith is also hereby incorporated by reference in its entirety (File Name: US-202 Seq List; File Size: 115 KB; Date Created: Jan. 17, 2006).

BACKGROUND OF THE INVENTION

1. Field of the Invention

The present invention relates to the fermentation microbiological industry, and specifically to a method for producing an L-amino acid using a bacterium of the Enterobacteriaceae family, wherein the bacterium has been modified so as to not produce type I fimbrial adhesin protein. L-amino acids are employed as components of pharmaceuticals, animal feed additives, seasonings, and various other nutritive mixtures.

2. Brief Description of the Related Art

L-amino acids are industrially produced by fermentation using L-amino-acid producing bacteria such as coryneform bacteria and the genus *Escherichia*. To enhance productivity, artificially mutated strains of these bacteria that have been isolated from nature or transformants in which activity of an L-amino acid biosynthesis enzyme has been increased by genetic recombination have been employed as the L-amino acid producing bacteria. (U.S. Pat. Nos. 5,661,012, 6,040,160, 5,827,698, 5,932,453, and WO01/53459)

In addition to methods of increasing the level of expression of enzymes which are a part of L-amino acid biosynthesis pathways, other methods of increasing the ability to produce L-amino acids such as L-lysine have been developed. Such methods include improving energy efficiency by modifying the energy pathway (EP1170376), increasing the ability to produce nicotinamide adenine dinucleotide phosphoric acid by amplifying the nicotinamide nucleotide transhydrogenase gene (U.S. Pat. No. 5,830,716), and inactivating genes related to flagella production (WO02/097089).

*Escherichia*, *Salmonella*, and *Bacillus* bacteria have fimbriae. Fimbriae can be divided into types I to V which have no direct relation to sexual processes such as conjugation and gene transfer, and sexual fimbriae that are produced on the outer layers of donor bacteria and are essential to conjugation with recipient bacteria and to gene transfer (Shoji Mizushima, Kinichiro Miura, Bacterial Anatomy 129 (1979)).

There are nine genes which contribute to the formation of type I fimbriae, and these genes form an operon. The fimH gene, located downstream within the operon, encodes a type I fimbrial adhesin protein. Type I fimbrial adhesin protein does not contribute to the formation of fimbriae, but is known to specifically recognize the mannosylated proteins of the host. Furthermore, it is known that the capacity for bacterial aggregation can be enhanced by introducing an amino acid substitution into the gene which encodes the type I fimbrial adhesin protein (Mark A. Schenbri, Gunna Christiansen and Per Klemm: FimH-mediated auto aggregation of *Escherichia coli*: Molecular Microbiology (2001) 41 (6), 1419-1430). However, there is no information relating to the relationship between the effect of introducing a mutation which causes reduction in the adhesion activity of type I fimbrial adhesin protein and L-amino acid production.

SUMMARY OF THE INVENTION

Objects of the present invention include enhancing the productivity of L-amino acid producing strains and providing a method for producing an L-amino acid. The above objects were achieved by finding that the bacterium which is modified so as to not produce type I fimbrial adhesion can improve L-amino acid productivity.

It is an object of the present invention to provide an L-amino acid producing bacterium of the Enterobacteriaceae family, wherein the bacterium has been modified so as to not produce type I fimbrial adhesin protein.

It is a further object of the present invention to provide the bacterium as described above, wherein said bacterium has been modified so as to not produce type I fimbrial adhesin protein by introducing a mutation into the gene encoding type I fimbrial adhesin protein on the chromosome and/or into the region regulating expression thereof.

It is a further object of the present invention to provide the bacterium as described above, wherein said bacterium has been modified so as to not produce type I fimbrial adhesin protein by attenuation of the gene encoding type I fimbrial adhesin protein.

It is a further object of the present invention to provide the bacterium as described above, wherein said bacterium has been modified so as to not produce type I fimbrial adhesin protein by inactivation of the gene encoding type I fimbrial adhesin protein on the chromosome.

It is a further object of the present invention to provide the bacterium as described above, wherein the gene encoding type I fimbrial adhesin protein is fimH.

It is a further object of the present invention to provide the bacterium as described above, wherein said gene encoding type I fimbrial adhesin protein is selected from the group consisting of: (a) a DNA comprising the nucleotide sequence of SEQ ID NO: 1, and (b) a DNA that is able to hybridize with the complementary strand of the nucleotide sequence of SEQ ID NO: 1, or a probe prepared from said nucleotide sequence under stringent conditions, and wherein the DNA encodes the type I fimbrial adhesin protein.

It is a further object of the present invention to provide the bacterium as described above, wherein said bacterium of the Enterobacteriaceae family is selected from the group consisting of *Escherichia*, *Pantoea*, and *Enterobacter*.

It is a further object of the present invention to provide the bacterium as described above, wherein said L-amino acid is selected from the group consisting of L-lysine, L-threonine, L-glutamic acid, and combinations thereof.

It is a further object of the present invention to provide a method for producing an L-amino acid comprising cultivating the bacterium as described above in a medium, and collecting said L-amino acid from the medium.

It is a further object of the present invention to provide the method as described above, wherein said L-amino acid is selected from the group consisting of L-lysine, L-threonine, L-glutamic acid, and combinations thereof.

DETAILED DESCRIPTION OF EXEMPLARY EMBODIMENTS

Figure 1:
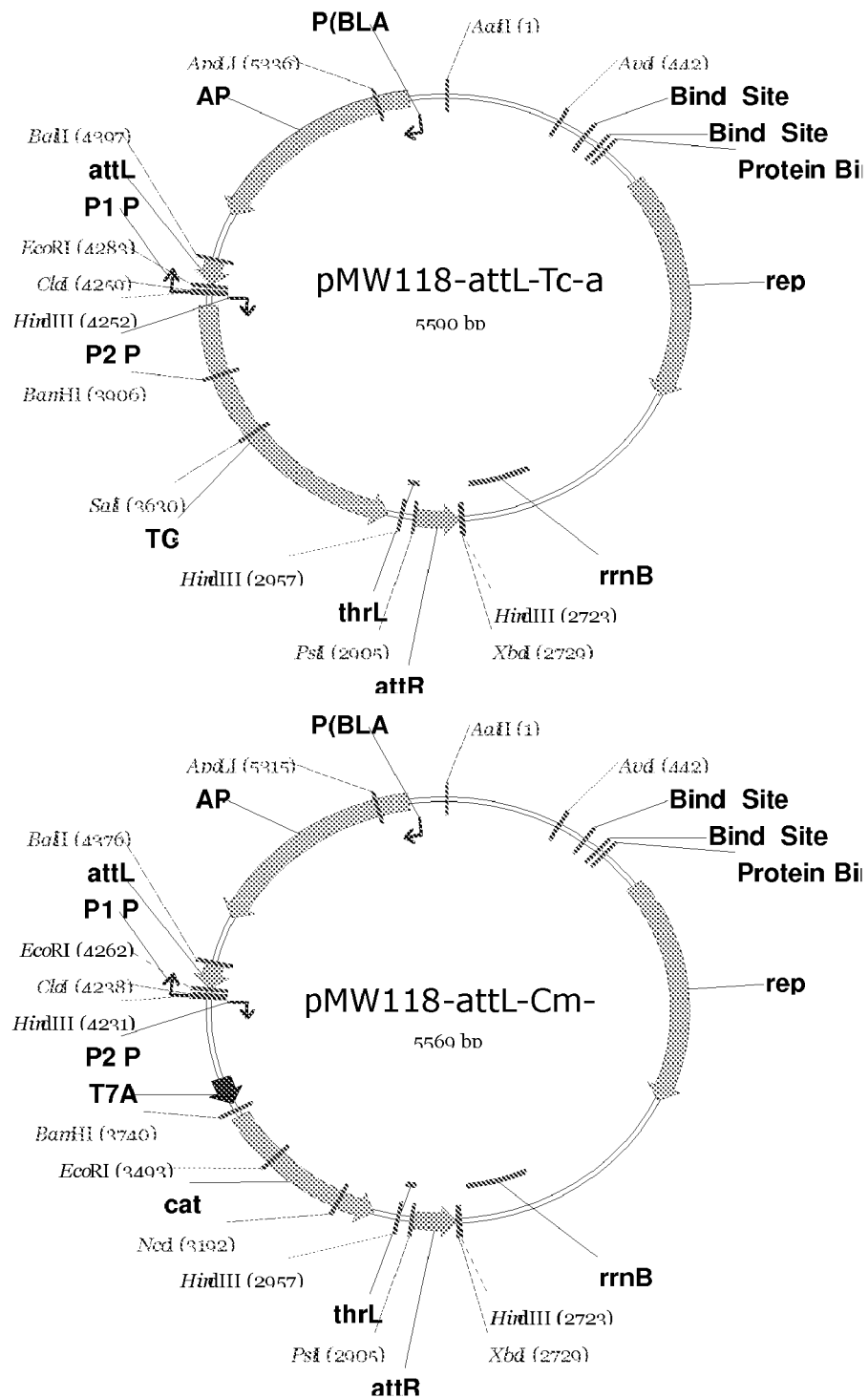
FIG. 1 shows the structure of pMW118-attL-Tc-attR and pMW118-attL-Cm-attR.
Figure 2:
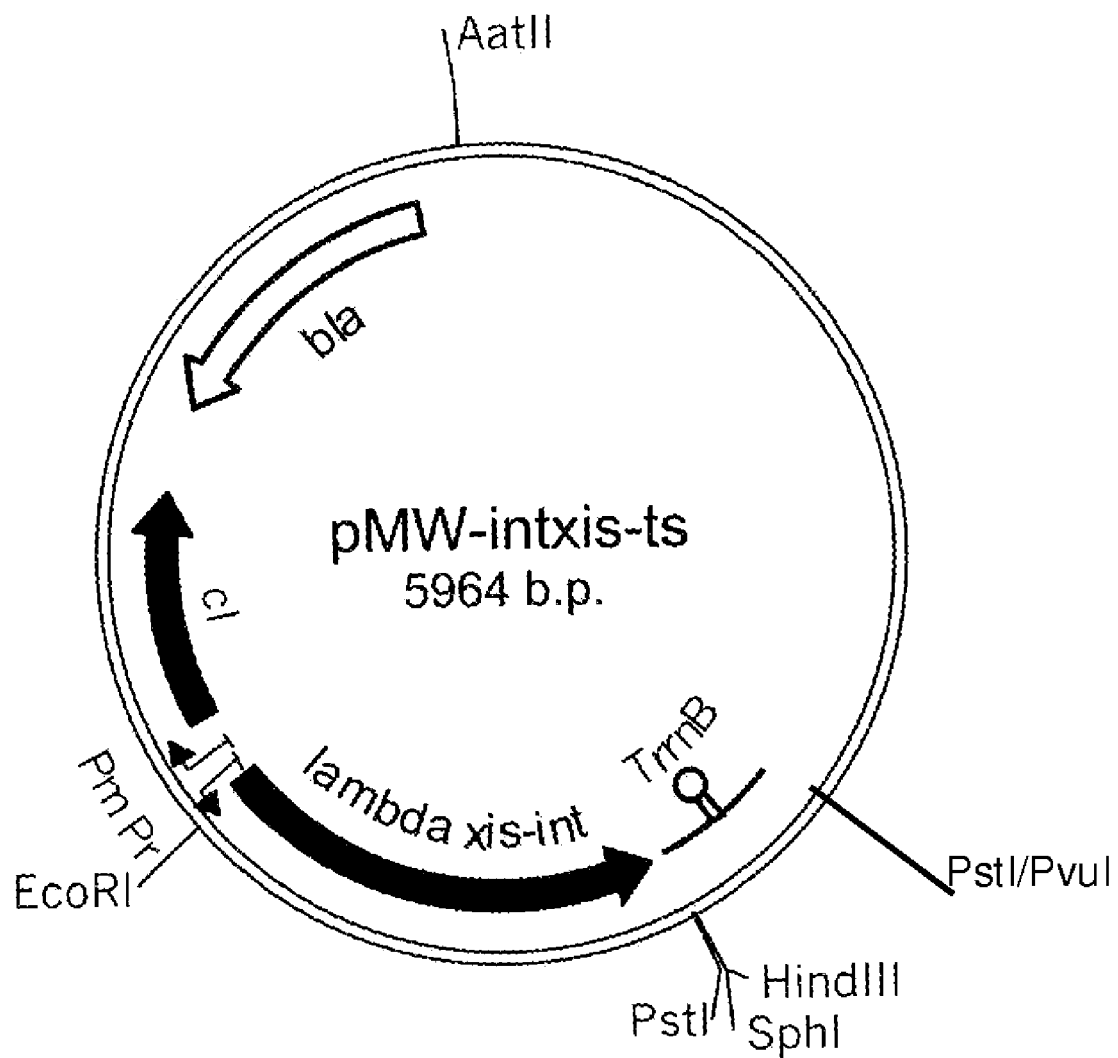
FIG. 2 shows the structure of pMW-intxis-ts.

<1> The Bacterium of the Present Invention

The bacterium of the present invention is a bacterium having the ability to produce an L-amino acid and which belongs to the Enterobacteriaceae family. The bacterium of the present invention has been modified so as to not produce type I fimbrial adhesin protein. The ability to produce L-amino acids may include production of any single L-amino acid, or production of multiple L-amino acids. Examples of produced L-amino acids of the present invention include L-lysine, L-glutamic acid, L-threonine, L-valine, L-leucine, L-isoleucine, L-serine, L-aspartic acid, L-asparagine, L-glutamine, L-arginine, L-cysteine (cystine), L-methionine, L-phenylalanine, L-tryptophan, L-tyrosine, L-glycine, L-alanine, L-proline, L-ornithine, L-citrulline, and L-homoserine. L-lysine, L-threonine, and L-glutamic acid are particularly desirable.

The phrase "ability to produce an L-amino acid" refers to the ability of a bacterium of the Enterobacteriaceae family to produce and cause accumulation of an L-amino acid in the bacterial cells or into a medium to a degree which permits its recovery from the bacterial cells or the medium when the bacterium is cultured in the medium. The bacterium which has this ability may originally have had the ability to produce an L-amino acid, or may be a bacterium, such as those set forth below, that has been modified by a mutation method or recombinant DNA technique to impart the ability to produce an L-amino acid. The bacterium of the present invention may also be one that has had the ability to produce an L-amino acid imparted to it by a modification which results in prevention of production of type I fimbrial adhesin production.

The Enterobacteriaceae family includes bacteria belonging to the genus *Escherichia, Enterobacter, Erwinia, Klebsiella, Pantoea, Photorhabdus, Povidencia, Salmonela, Serratia, Shigella, Morganella,* and *Yersinia,* etc. Specifically, bacteria of the Enterobacteriaceae family which have been classified in the database of the National Center for Biotechnology Information (NCBI) can be employed. Of these, the parent strain from the Enterobacteriaceae family employed for modification is desirably from the genus *Escherichia, Enterobacter,* or *Pantoea.*

The parent strain from the genus *Escherichia* which is used to obtain the bacterium of the present invention is not specifically limited. Specifically, strains described by Neidhardt et al. may be employed (Neidhardt, F. C. et al., *Escherichia coli* and *Salmonella typhimurium,* American Society for Microbiology, Washington D.C., 1029 table 1). Of these, one example is *Escherichia coli.* Specific examples of *Escherichia coli* are *Escherichia coli* W3110 (ATCC 27325) and *Escherichia coli* MG1655 (ATCC 47076), both of which are derived from the prototype wild-type strain K12.

These strains can be obtained from the American Type Culture Collection (P.O. Box 1549, Manassas, Va. 20108 USA, (703) 365-2700) using the assigned registration number (http://www.atcc.org (reference)). The registration number corresponding to each strain is listed at the American Type Culture Collection web site and catalog.

Examples of strains from the genus *Enterobacter* are *Enterobacter agglomerans* and *Enterobacter aerogenes.* An example of a strain from the genus *Pantoea* is *Pantoea ananatis.* In recent years, based on 16S rRNA base sequencing analysis, *Enterobacter agglomerans* has on occasion been reclassified as *Pantoea agglomerans, Pantoea ananatis,* or *Pantoea stewartii.* (Int. J. Syst. Bacteriol., 43, 162-173) For the present invention, any bacterium classified in the Enterobacteriaceae family, whether under genus *Enterobacter* or *Pantoea,* may be employed. Strains *Pantoea ananatis* AJ13355 (FERM BP-6614), AJ13356 (FERM BP-6615), AJ13601 (FERM BP-7207), or any derivative thereof may be employed to breed *Pantoea ananatis* by genetic engineering methods. When isolated, these strains were identified and deposited as *Enterobacter agglomerans.* As stated above, analysis by 16S rRNA base sequencing has caused them to be reclassified as *Pantoea ananatis.*

Methods of imparting the ability to produce an L-amino acid to a bacterium of the Enterobacteriaceae family will be described below.

To impart the ability to produce an L-amino acid, an auxotrophic mutant, an analog-resistant strain, or a metabolic regulation mutant can be obtained, or a recombinant strain having enhanced expression of an L-amino acid biosynthetic enzyme can be created. Conventionally, methods that have been employed to breed coryneform bacteria and bacteria from the genus *Escherichia* can be used (See "Amino Acid Fermentation", the Japan Scientific Societies Press [Gakkai Shuppan Center], 1st Edition, published on May 30, 1986, pp. 77-100). Here, in the breeding of L-amino acid producing bacteria, one or more properties such as an auxotrophic mutation, analog resistance, and a metabolic regulation mutation may be imparted. When a recombinant strain is created, the activity of one or more L-amino acid biosynthetic enzymes may be enhanced. Furthermore, imparting properties such as an auxotrophic mutation, analog resistance, and a metabolic regulation mutation may be combined with the methods for enhancing an activity of one or more L-amino acid biosynthetic enzymes.

An auxotrophic mutant strain, L-amino acid analog resistant strains, or metabolic regulation-mutated strain with the ability to produce an L-amino acid can be obtained by subjecting a parent strain or wild-type strain to a typical mutation treatment, such as exposure to X-rays or UV radiation, or treatment with a mutagenic agent such as N-methyl-N'-nitro-N-nitrosoguanidine(NTG), and selecting from among the obtained mutants those which exhibit an auxotrophic mutation, analog resistance, or a metabolic regulation-mutation and which also have the ability to produce an L-amino acid. Genetic recombination can be employed to enhance the L-amino acid biosynthetic enzyme activity of a bacterium which produces L-amino acids.

Specific examples of L-lysine analog-resistant strains and metabolic regulation-mutated strains which are able to produce L-lysine include *Escherichia coli* strain AJ11442 (FERM BP-1543, NRRL B-12185; see JP56-18596A and U.S. Pat. No. 4,346,170) and *Escherichia coli* strain VL611 (JP 2000-189180A). Strain WC196 (see WO96/17930) may also be employed as an *Escherichia coli* L-lysine producing strain. Strain WC196 was originally bred by imparting resistance to S-(2-aminoethyl)cysteine (AEC) to strain W3110, which is derived from *Escherichia coli* K-12. The resulting strain was also designated as *Escherichia coli* strain AJ13069 and deposited on Dec. 6, 1994, accession number FERM P-14690, at the National Institute of Bioscience and Human-Technology, Agency of Industrial Science and Technology (currently the International Patent Organism Depositary, National Institute of Industrial Science and Technology, an Independent Administrative Institution, Central 6, 1-1-1 Higashi, Tsukuba, Ibaraki, Japan Postal Code 305-8566). Then, the deposit was converted to an international deposit under the provisions of the Budapest Treaty on Sep. 29, 1995, and received an accession number of FERM BP-5252.

Furthermore, enzymatic activity relating to L-lysine biosynthesis can be enhanced to construct a bacterium which produces L-lysine. Examples of genes encoding proteins involved in L-lysine biosynthesis include, but are not limited to, genes encoding diaminopimelic acid pathway enzymes, such as the dihydrodipicolinate synthase gene (dapA), aspartokinase gene (lysC), dihydrodipicolinate reductase gene (dapB), diaminopimelate decarboxylase gene (lysA), diaminopimelate dehydrogenase gene (ddh) (WO96/40934), phosphenolpyruvate carboxylase gene (ppc) (JP60-87788), aspartate aminotransferase gene (aspC) (JP 6-102028), diaminopimelate epimerase gene (dapF) (JP2003-135066), aspartate semialdehyde dehydrogenase gene (asd) (WO00/61723), and genes encoding aminoadipic acid pathway enzymes, such as the homoaconitate hydratase gene (JP2000-157276).

In addition to methods of increasing the level of expression of Lys biosynthesis enzymes, other methods of increasing the ability to produce L-lysine have been developed. Such methods include increasing expression levels of the gene involved in energy efficiency(cyo) (EP1170376), the nicotinamide nucleotide transhydrogenase gene (pntAB)(U.S. Pat. No. 5,830,716), and the ybjE gene(WO2005/073390).

For example, the ability to produce L-lysine can be imparted by introducing a gene encoding a protein involved in L-lysine biosynthesis into a host as set forth below. That is, a gene fragment encoding an L-lysine biosynthesis gene is ligated to a vector which is able to function in a host microorganism which has been employed to produce L-lysine. The chosen vector preferably is a multicopy-type vector, which is then used to transform the host. Since the number of copies of the genes encoding proteins involved in L-lysine biosynthesis increases in the transformed host cell, the expression level is increased and the activity of the enzymes is enhanced.

The genes encoding proteins involved in L-lysine biosynthesis are not specifically limited, other than that they must be able to be expressed in the host microorganism. Examples include genes derived from *Escherichia coli* and coryneform bacteria. Since the genomic sequences of both *Escherichia coli* and *Corynebacterium glutamicum* are known, a primer can be synthesized based on the sequences of the genes, and PCR employing the chromosomal DNA of a microbe such as *Escherichia coli* K-12 can be employed to obtain the genes (Science 277 (5331), 1453-1474 (1997) Proceedings of the 9th International Symposium on the Genetics of Industrial Microorganisms: 21).

The plasmids which may be used for gene cloning may be capable of autonomous replication in the bacteria from the Enterobacteriaceae family; specific examples are pBR322, pTWV228 (Takara-Bio Co.), pMW119 (Nippon Gene Corp.), pUC19, pSTV29 (Takara-Bio Co.), and RSF1010 (Gene vol. 75 (2), p. 271-288, 1989). Phage DNA vectors may also be employed.

To ligate the target gene to the above-described vector to prepare recombinant DNA, the vector is digested with a restriction enzyme matched to the end of the DNA fragment containing the target gene. The ligation is usually conducted with a ligase such as T4 DNA ligase. The target genes may be introduced into a variety of separate vectors, or introduced into a single vector. The usual methods known to those skilled in the art can be employed to digest and ligate DNA, prepare chromosomal DNA, conduct PCR, prepare plasmid DNA, transform hosts, and determine oligonucleotides for use as primers. These methods are described in Sambrook, J., Fritsch, E. F., and Maniatis, T., "Molecular Cloning A Laboratory Manual, Second Edition", Cold Spring Harbor Laboratory Press, (1989). Any method which achieves adequate transformation efficiency can be used to introduce recombinant DNA that has been prepared as set forth above into the microbe. An example is the electroporation method (Canadian Journal of Microbiology, 43. 197 (1997)).

Enhancing expression of the genes encoding proteins involved in L-lysine biosynthesis can be achieved by introducing multiple copies of the target gene into the chromosomal DNA of the microorganism. Multiple copies of the target gene can be introduced into the chromosomal DNA of the microorganism by using a DNA in which multiple copies are present in chromosomal DNA as a target in homologous recombination. Such site-specific introduction of mutations based on genetic recombination using homologous recombination is already established. There is a method employing single strand DNA and a method employing a plasmid containing temperature-sensitive replication origin (U.S. Pat. No. 6,303,383 or JP05-007491A). Repetitive DNA and inverted repeats present on the ends of transposable elements can be employed as sequences in which multiple copies are preset in chromosomal DNA. Alternatively, as disclosed in EP0332488, multiple copies of the target gene can be introduced into a chromosome. With either method, as a result of increasing the number of copies of the target gene in the transformant, the enzymatic activity of L-lysine biosynthesis increases.

In addition to the above-described genetic amplification, L-lysine biosynthesis enzyme activity can be enhanced by replacing the expression regulatory sequence of the promoter of the target gene with a stronger one (JP01-215280A). For example, lac promoter, trp promoter, trc promoter, tac promoter, lambda phage PR promoter, lambda phage PL promoter, tet promoter are all known as strong promoters. Substitution with these promoters enhances the enzymatic activity by increasing expression of the target gene. A paper by Goldstein (Prokaryotic promoters in biotechnology. Biotechnol. Annu. Rev., 1995, 1, 105-128) describes methods of evaluating the strength of promoters and gives examples of strong promoters.

This can also be achieved by modifying factors relating to regulation of expression of the target gene, such as operators and repressors (Hamilton et al; J Bacteriol. 1989 September; 171(9): 4617-22). As is disclosed in WO00/18935, it is possible to introduce a substitution of several bases into the promoter region of a target gene to increase its strength. Furthermore, the substitution of several nucleotides into the spacer between a ribosome binding site (RBS) and a start codon, particularly into the sequence immediately upstream from a start codon, is known to have a strong effect on mRNA translation efficiency. The expression adjustment regions of the promoters or the like of the target gene can be determined using promoter search vectors and gene analysis software such as GENETYX. Substitution of the expression regulating sequence can be conducted, for example, in the same manner as in the above-described gene substitution employing temperature-sensitive plasmids.

Furthermore, the L-lysine producing bacterium of the present invention may have reduced or deficient activity of enzymes which catalyze reactions that branch off from the L-lysine biosynthesis pathway and produce compounds other than L-lysine. Examples of such enzymes are homoserine dehydrogenase, lysine decarboxylase (cadA, ldcC), and malic enzyme. Strains in which the activity of these enzymes is reduced or eliminated are described in WO 95/23864, WO96/17930, and WO2005/010175.

Examples of methods of reducing or eliminating the intracellular activity of an enzyme include mutating or deleting a gene encoding the enzyme in cells of a microorganism so that intracellular activity is reduced or eliminated as compared to a non-mutated strain. For example, this can be achieved by using recombination to inactivate the gene encoding the enzyme on the chromosome, or to modify an expression regulating sequence such as a promoter or the Shine-Dalgarno (SD) sequence. (WO95/34672, Biotechnol Prog 1999, 15,58-64) This can also be achieved by introducing an amino acid substitution (missense mutation) into the region encoding the enzyme on the chromosome, introducing a stop codon (nonsense mutation), introducing or deleting one or two bases to create a frame shift mutation, or partially deleting a portion or a region of the gene, or the entire gene (Journal of Biological Chemistry 272: 8611-8617 (1997), Journal of Antimicrobial Chemotherapy 200 46, 793-79. J. biological Chemistry vol 272 No. 13 pp 8611-8617). Enzymatic activity can also be decreased or eliminated by constructing a gene encoding a mutant enzyme which lacks a coding region, using homologus recombination to replace the normal gene on the chromosome with this gene, and introducing a transposon or IS factor into the gene.

For example, the following methods may be employed to introduce a mutation causing a decrease of, or eliminating, the above enzyme activity by gene recombination. A portion of the sequence of the targeted gene is modified, a mutant gene that does not produce a normally functioning enzyme is prepared, DNA containing this gene is used to transform a microbe from the Enterobacteriaceae family, and the mutant gene is made to recombine with the gene on the chromosome, which results in replacing the target gene on the chromosome with the mutant gene. Such gene substitution using homologous recombination can be conducted by methods employing linear DNA, such as the method known as "Red-driven integration" (Proc. Natl. Acad. Sci. USA, 2000, vol. 97, No. 12, p 6640-6645), and by methods employing a plasmid containing a temperature-sensitive replication (Proc. Natl. Acad. Sci. USA, 2000, vol. 97, No. 12, p 6640-6645, U.S. Pat. No. 6,303,383 or Japanese Patent Application Publication No. Hei 05-007491). Furthermore, the incorporation of a site-specific mutation by gene substitution using homologous recombination such as set forth above can also be conducted with a plasmid lacking the ability to replicate in the host.

The above-described methods of enhancing and decreasing the activity of enzymes relating to L-lysine biosynthesis can also be applied to the breeding of bacteria producing other L-amino acids. Methods of breeding bacteria producing other L-amino acids will be described below.

The L-glutamic acid producing bacterium employed in the present invention can be a microorganism from the Enterobacteriaceae family that has been modified to enhance expression of a gene encoding an enzyme related to L-glutamic acid biosynthesis, for example. Examples of enzymes related to L-glutamic acid biosynthesis are glutamate dehydrogenase (also referred to as "GDH" hereinafter), glutamine synthetase, glutamate synthase, isocitrate dehydrogenase, aconate hydratase, citrate synthase (also referred to as "CS" hereinafter), pyruvate carboxylase, pyruvate dehydrogenase, pyruvate kinase, phosphophenol pyruvate synthase, enolase, phosphoglyceromutase, phosphoglycerate kinase, glyceraldehyde-3-phosphate dehydrogenase, triosephosphate isomerase, fructose bisphosphate aldolase, phosphofructokinase, and glucose phosphate isomerase. Among these enzymes, one or more from among CS, PEPC, and GDH are desirable, with all three being preferred.

For example, U.S. Pat. Nos. 6,197,559 and 6,331,419 and European Patent 0999282 describe microbes from the Enterobacteriaceae family that have been modified by methods such as those set forth above to enhance expression of the citrate synthase gene, phosphenolpyruvate carboxylase gene, and/or glutamate dehydrogenase gene.

A microorganism which has reduced or eliminated activity of enzymes which catalyze reactions that branch off from the L-glutamic acid biosynthesis pathway and produce compounds other than L-glutamic acid may also be employed as the microorganism from the Enterobacteriaceae family which has the ability to produce L-glutamic acid. Examples of enzymes which catalyze reactions that branch off from the L-glutamic biosynthesis pathway and produce compounds other than L-glutamic acid are: 2-oxoglutamate dehydrogenase, isocitrate lyase, phosphate acetyl transferase, acetate kinase, acetohydroxamate synthase, acetolactate synthase, formate acetyl transferase, lactate dehydrogenase, glutamate decarboxylase. Among these, the reduction or elimination of 2-oxoglutamate dehydrogenase activity is desirable.

U.S. Pat. Nos. 6,197,559 and 6,331,419 describe methods of eliminating or reducing the 2-oxoglutamate dehydrogenase activity in a microorganism from the Enterobacteriaceae family. Specific examples of a bacterium from the Enterobacteriaceae family in which 2-oxoglutamate dehydrogenase activity has been eliminated or reduced are:

Pantoea ananatis AJ13601 (FERM BP-7207)
Klebsiella planticola AJ13410 (FERM BP-6617)
Pantoea ananatis AJ13355 (FERM BP-6614)
Escherichia coli AJ12949 (FERM BP-4881).

Strain AJ12949 was deposited on Dec. 28, 1993, as depository number FERM P-14039, at the National Institute of Bioscience and Human-Technology, Agency of Industrial Science and Technology (currently the International Patent Organism Depositary, National Institute of Industrial Science and Technology, an Independent Administrative Institution, Central 6, 1-1-1 Higashi, Tsukuba, Ibaraki, Japan Postal Code 305-8566), and converted to a international deposit under the provisions of the Budapest Treaty on Nov. 11, 1994, and given accession number FERM BP-4881.

The preferred L-tryptophan producing microorganism employed in the present invention enhances the activity of one or more of the following proteins: anthranilate synthase, phosphoglycerate dehydrogenase, and tryptophan synthase. Anthranilate synthase and phosphoglycerate dehydrogenase are subject to feedback suppression by L-tryptophan and L-serine, respectively. Thus, their enzymatic activity can be enhanced by retaining a desensitized mutant enzyme. Specifically, for example, the anthranilate synthase gene (trpE) and/or the phosphoglycerate dehydrogenase gene (serA) can be mutated so as to not be subject to feedback inhibition, and the mutant gene obtained can be introduced into a microorganism of the Enterobacteriaceae family to obtain a microorganism retaining the desensitized enzyme. Specific examples of such microbes are transformed strains obtained by introducing plasmid pGH5 having a mutant form of serA encoding desensitized phosphoglycerate dehydrogenase into *Escherichia coli* SV164 which has retained a desensitized from of anthranilate synthase (WO94/08031).

A microorganism into which a recombinant DNA containing a tryptophan operon has been introduced is a further example of a desirable L-tryptophan-producing bacteria. One specific example is *Escherichia coli* into which a tryptophan operon containing a gene encoding desensitized anthranilate synthase has been introduced (Japanese Patent Application Publication Nos. Sho 57-71397 and Sho 62-244382, and U.S. Pat. No. 4,371,614). Among the tryptophan operons, enhancement of the expression of the gene (trpBA) encoding tryptophan synthase also enhances or imparts L-tryptophan production capability. Tryptophan synthase contains α and β subunits encoded by trpA and trpB, respectively.

Further examples of L-tryptophan producing bacteria are *Escherichia coli* strain AGX17(pGX44) (NRRL B-12263), which requires L-phenylalanine and L-tyrosine, and strain AGX6(pGX50)aroP (NRRL B-12264), which retains a plasmid pGX50 containing a tryptophan operon (see U.S. Pat. No. 4,371,614 for both of these).

Examples of L-phenylalanine-producing strains derived from the K-12 strain include the AJ12739 strain in which the tyrA gene and the tyrR gene are disrupted (tyrA::Tn10, tyrR) (VKPM B-8197), and a strain in which the yddG gene and the yedA gene, which are involved in phenylalanine excretion, are amplified (WO 03/044192).

The strain which is modified to enhance genes which encode proteins involved in aromatic amino acids biosynthesis can also be used as the tryptophan and/or phenylalanine-producing strain, such genes include genes which encode proteins involved in a common pathway for aromatic acids, such as aroF, aroG, aroH, aroB, aroD, aroE, aroK, aroL, aroA, and aroC genes.

A strain having 6-dimethylaminopurine resistance (JP 5-304969A) is desirable as the L-threonine producing bacterium employed in the present invention. Examples of recombinant bacteria of the genus *Escherichia* are a strain in which a mutation producing excessive L-threonine biosynthase has been introduced into the threonine biosynthesis gene and the gene has been amplified on a plasmid (JP 1-29559A and JP5-227977A), a strain in which a threonine operon has been amplified with a plasmid (Japanese Patent Application Publication No. Hei 2-109985), and a strain in which a gene encoding pyruvate carboxylase and a gene encoding nicotinamide nucleotide transhydrogenase have been amplified (JP2002-51787A).

A further example is *Escherichia coli* strain VKPM B-3996 (see U.S. Pat. No. 5,175,107). Strain VKPM B-3996 was deposited on Nov. 19, 1987, with the Russian National Collection of Industrial Microorganisms (VKPM), GNII Genetika, and given deposit number VKPM B-3996. Strain VKPM B-3966 harbors a plasmid pVIC40 (WO90/04636), which is obtained by inserting a threonine biosynthesis gene (threonine operon: thrABC) into a broad host vector plasmid pAYC32 (see Chistorerdov, A. Y., Tsygankov, Y. D. Plasmid, 1986, 16, 161-167) having a streptomycin-resistance marker. In pVIC40, feedback inhibition by L-threonine of the aspartokinase I homoserine dehydrogenase I encoded by thrA in the threonine operon is repressed.

A further example is *Escherichia coli* strain B-5318 (EP 0593792B). Strain B-5318 was deposited on Nov. 19, 1987, with the Russian National Collection of Industrial Microorganisms (VKPM), GNII Genetika, and given deposit number VKPM B-5318. Strain VKPM B-5318 is autotrophic to L-isoleucine. It harbors a recombinant plasmid DNA carrying a threonine operon lacking the attenuator region (the transcription regulating region originally present), that is, a gene related to threonine biosynthesis. The operon is downstream from the N-terminal portion of the Cro protein, PR promoter, and temperature-sensitive C1 repressor of λ phage, with the expression of the gene related to threonine biosynthesis being controlled by the repressor and promoter of the λ phage.

Preferably, the bacterium of the present invention is additionally modified to enhance expression of one or more of the following genes:
the mutant thrA gene which codes for aspartokinase homoserine dehydrogenase I and is resistant to feedback inhibition by threonine;
the thrB gene which codes for homoserine kinase;
the thrC gene which codes for threonine synthase;
the rhtA gene which codes for a putative transmembrane protein;
the asd gene which codes for aspartate-β-semialdehyde dehydrogenase; and
the aspC gene which codes for aspartate aminotransferase (aspartate transaminase);

The thrA gene which encodes aspartokinase homoserine dehydrogenase I of *Escherichia coli* has been elucidated (nucleotide positions 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession NC_000913.2, gi: 49175990). The thrB gene is located between the thrA and thrC genes on the chromosome of *E. coli* K-12. The thrC gene which encodes threonine synthase of *Escherichia coli* has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes functions as a single threonine operon. The regulation sequence which encodes an attenuator and leader peptide is present upstream of the threonine operon. To enhance the expression of threonine operon, a leader sequence and/or an attenuator is desirably removed from said operon. (WO2005/049808, WO2003/097839)

A mutant thrA gene which codes for aspartokinase homoserine dehydrogenase I and is resistant to feedback inhibition by threonine, as well as, the thrB and thrC genes can be obtained as one operon from the well-known plasmid pVIC40 which is present in the threonine producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession NC_000913.1, gi: 16131307), and can be obtained by PCR (polymerase chain reaction; refer to White, T. J. et al., Trends Genet., 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC_000913.1, gi:16128895), and can be obtained by PCR. The aspC genes of other microorganisms can be obtained in a similar manner.

Examples of L-histidine producing bacteria that are desirable for use in the present invention are strains of *Escherichia coli* FERM-P5038 and 5048, both of which incorporate a vector containing DNA encoding an L-histidine biosynthetic enzyme (JP56-005099A), a strain having the vector containing the amino acid export gene rht (European Patent Publication No. 1016710), and *Escherichia coli* strain 80, which is imparted with resistance to sulfaguanidine, D,L-1,2,4-triazole-3-alanine, and streptomycin (VKPM B-7270 Russian Patent Publication No. 2,119,536).

A microorganism with enhanced expression of genes encoding enzymes of the L-histidine biosynthesis pathway may be employed as a microorganism which has the ability to produce L-histidine. Examples of enzymes involved in L-histidine biosynthesis are ATP phosphoribosyltransferase (hisG), phosphoribosyl AMP cyclohydrolase (hisI), phosphoribosyl ATP pyrophosphohydrolase (hisIE), phosphoribosylformimino-5-aminoimidazole carboxamide ribotide isomerase (hisA), amidotransferase (hisH), histidinolphosphate aminotransferase (hisC), histidinolphosphatase (hisB), and histidinoldehydrogenase (hisD).

Desirable examples of the L-cysteine producing bacterium of the present invention are bacteria which have reduced cystathionine-β-lyase activity (JP2003-169668A) and *Escherichia coli* bacteria which retain serineacetyltransferase, the activity of which is decreased by feedback suppression by L-cysteine (JP11-155571A).

Desirable examples of L-proline producing bacterium of the present invention are *Escherichia coli* strain 702 (VKPMB-8011), which is resistant to 3,4-dehydroxyproline and azatadine-2-carboxylate, and strain 702ilvA (VKPMB-8012), which lacks the ilvA of strain 702 (JP2002-300874A).

Examples of a bacterium which produces L-arginine are *Escherichia coli* strains with resistance to α-methylmethionine, p-fluorophenylalanine, D-arginine, arginine hydroxamic acid, S-(2-aminoethyl)cysteine, α-methylserine, β-2-thienylalanine, or sulfaguanidine (JP56-106598A). *Escherichia coli* strain 237 (US Patent Application No. 2003/058315), which is an L-arginine producing bacterium harboring mutant N-acetylglutamate synthass, is also a desirable L-arginine producing strain. This strain was deposited on Apr. 10, 2000, with the Russian National Collection of Industrial Microorganisms (VKPM), GNII Genetika under number VKPM B-7925 and was converted on May 18, 2001 to an International Deposit under the Budapest Treaty. A derivative of strain 237 that produces L-arginine and has enhanced acetic acid utilizing capability, *Escherichia coli* strain 382 (EP1170358A) can also be employed. *Escherichia coli* strain 382 was deposited on Apr. 10, 2000, with the Russian National Collection of Industrial Microorganisms (VKPM) as deposit number VKPM B-7926.

Microorganisms with an enhanced level of expression of genes encoding enzymes related to L-arginine biosynthesis can also be employed as a microorganism having L-arginine production ability. Examples of enzymes related to L-arginine biosynthesis are one or more selected from among N-acetylglutamate synthase (argA), N-acetylglutamylphosphate reductase (argC), ornithine acetyltransferase (argJ), N-acetylglutamate kinase (argB), acetylornithine transferase (argD), acetylornithine deacetylase (argE), ornithinecarbamoyltransferase (argF), argininosuccinate synthase (argG), argininosuccinate lyase (argH), and carbamoylphosphate synthase (carAB).

L-leucine producing bacteria of the present invention include a bacterium of the genus *Escherichia* in which the branched chain amino acid transferase encoded by the ilvE gene is inactivated and the activity of aromatic amino acid transaminase encoded by the tyrB gene is enhanced (JP2004-024259), *Escherichia coli* strain H-9068 (ATCC21530), *Escherichia coli* strain H-9070 (FERM BP-4704), *Escherichia coli* strain 9072 (FERM BP-4706) which is resistant to 4-azoleucine or 5,5,5-trifluoroleucine (U.S. Pat. No. 5,744,331) strains of *Escherichia coli* in which feedback inhibition of isopropylmalate synthase by L-leucine has been repressed (European Patent No. 1067191), and *Escherichia coli* strain AJ11478 which is resistant to β-2-thienylalanine and β-hydroxyleucine (U.S. Pat. No. 5,763,231).

The bacterium of the present invention may be improved by enhancing the expression of one or more genes involved in L-leucine biosynthesis. Examples include genes of the leuABCD operon, which are preferably represented by a mutant leuA gene coding for isopropylmalate synthase freed from feedback inhibition by L-leucine (U.S. Pat. No. 6,403,342). In addition, the bacterium of the present invention may be improved by enhancing the expression of one or more genes coding for proteins which excrete L-amino acid from the bacterial cell. Examples of such genes include the b2682 and b2683 genes (ygaZH genes) (EP 1239041 A2).

Examples of L-isoleucine producing bacteria are *Escherichia coli* variants with resistance to 6-dimethylaminopurine (JP5-304969A), *Escherichia coli* mutants with resistance to L-isoleucine hydroxamate (JP5-130882A), *Escherichia coli* strains with resistance to thiaisoleucine (JP5-130882A), *Escherichia coli* mutants with resistance to DL-ethionine (JP5-130882A), and variants with resistance to arginine hydroxamate(JP5-130882A) with the ability to produce L-isoleucine. Examples of recombinant bacteria of the genus *Escherichia* are strains with genes encoding proteins involved in L-isoleucine biosynthesis, such as threonine deaminase or acetohydroxate synthase enhanced with plasmids (JP2-458A, 2-42988A, and 8-47397A).

An example of a bacterium producing L-valine include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by L-valine that is produced. Furthermore, the ilvA gene in the operon is desirably disrupted so that threonine deaminase activity is decreased.

Examples of parent strains for deriving L-valine-producing bacteria of the present invention also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 113545 Moscow, 1 Dorozhny Proezd.) on Jun. 24, 1988 under accession number VKPM B-4411.

Furthermore, mutants requiring lipoic acid for growth and/or lacking H+-ATPase can also be used as parent strains (WO96/06926).

The microorganism of the present invention can be obtained by modifying a microbe of the Enterobacteriaceae family which has the ability to produce L-amino acid so that it cannot produce type I fimbrial adhesin protein, as set forth above. When breeding a microbe of the Enterobacteriaceae family of the present invention, it makes no difference whether the ability to produce an L-amino acid is imparted first or a modification to prevent production of type I fimbrial adhesin protein is made first. Furthermore, a microbe from the Enterobacteriaceae family which has the ability to produce an L-amino acid may be modified so that it does not produce type I fimbrial adhesin protein, or a microbe from the Enterobacteriaceae family that no longer produces type I fimbrial adhesin protein may be imparted with the ability to produce an L-amino acid. It suffices for the microorganism of the present invention to be modified so that it does not normally produce type I fimbrial adhesin protein in the manner of wild-type strains or unmodified strains. However, it is desirable for the microbe of the present invention to have an ability to cause accumulation of an L-amino acid exceeding that of these strains.

The "fimbriae" of the present invention are filamentous protrusions present on the outer cell membrane of microorganism from the Enterobacteriaceae family. Fimbriae can be divided into two types. One type is the fimbriae which has no direct relation to sexual processes such as conjugation and gene transfer, and the second type is sexual fimbriae that are produced on the outer layer of gene-donor bacteria and are essential to conjugation with gene-recipient bacteria. The "fimbriae" referred to in the present invention are the former, and are not directly related to sexual processes such as conjugation, gene transfer, or the like (Shoji Mizushima, Kinichiro Miura, Bacterial Anatomy 129 (1979)).

In the present invention, the phrase "type I fimbrial adhesin protein" refers to a protein which belongs to a group of proteins which control the formation of fimbriae, and furthermore, the protein has a function of blocking coagulation of red corpuscles by D-mannose.

The phrase "modified so as not to produce type I fimbrial adhesin protein" refers to when the quantity of type I fimbrial adhesin protein that is produced is lower than that in unmodified strains, and when the conformation of the protein is modified so that normal fimbriae cannot be produced by microbes from the Enterobacteriaceae family. For example, wild-type strains such as *Escherichia coli* strain W3110 (ATCC 27325), which is derived from the prototypical wild-type strain K12, and *Escherichia coli* MG1655 (ATCC 47076), are examples of control strains from the genus *Escherichia*. Confirmation of a decrease in the quantity of type I fimbrial adhesin protein which is produced, or the lack of production of type I fimbrial adhesin protein can be determined by the immunofluorescent antibody method, a decrease in the level of coagulation in the presence of D-mannose, or the lack of ability for coagulation (see the methods of Pallesen et al.: Microbiology 141; 2839-2848).

The type I fimbrial adhesin protein (Seq. ID No. 2) from the genus *Escherichia* is encoded by the gene fimH (Seq. ID No. 1). Type I fimbrial adhesin proteins from other microbes of the Enterobacteriaceae family include fimH homologs; for example, such homologs include genes capable of amplification by PCR using synthetic oligonucleotides of Seq. ID Nos. 7 and 8 and templates in the form of microbial chromosomes. Homologs of fimH from Enterobacteriaceae can be obtained by searching for genes having high homology to the gene denoted by Seq. ID No. 1 with BLAST (http://blast.genome.jp).

The GenBank Accession number of the amino acid sequence of the type I fimbrial adhesin protein from *Escherichia* microbes and the fimH gene encoding this protein are given in Table 1. Examples of the group of genes which encode proteins which control formation of fimbriae in the bacteria from genus *Escherichia* are fimB, fimE, fimA, fimI, fimC, fimD, fimF, fimG, and fimH. The amino acid sequences encoded by these genes, their gene sequences, and their GenBank Accession numbers are given in Table 1.

TABLE 1

| Gene | Protein | Function | Amino acid sequence ID | Gene sequence ID | GenBank Accession No. |
|---|---|---|---|---|---|
| fimB | recombinase involved in phase variation; regulator for fimA | regulator; surface structures | Seq. ID No. 47 | Seq. ID No. 46 | NP_418732. |
| fimE | recombinase involved in phase variation; regulator for fimA | regulator; surface structures | Seq. ID No. 49 | Seq. ID No. 48 | NP_418733 |
| fimA | major type 1 subunit fimbrin (pilin) | structural component; surface structures | Seq. ID No. 51 | Seq. ID No. 50 | NP_418734 |
| fimI | fimbrial protein | structural component; surface structures | Seq. ID No. 53 | Seq. ID No. 52 | NP_418735 |
| fimC | periplasmic chaperone, required for type 1 fimbriae | factor; surface structures | Seq. ID No. 55 | Seq. ID No. 54 | NP_418736 |
| fimD | outer membrane protein; export and assembly of type 1 fimbriae, interrupted | membrane; outer membrane constituents | Seq. ID No. 57 | Seq. ID No. 56 | NP_418737. |
| fimF | fimbrial morphology | structural component; surface structures | Seq. ID No. 59 | Seq. ID No. 58 | NP_418738 |
| fimG | fimbrial morphology | structural component; surface structures | Seq. ID No. 61 | Seq. ID No. 60 | NP_418739. |
| fimH | minor fimbrial subunit, D-mannose specific adhesin | structural component, surface structures | Seq. ID No. 2 | Seq. ID No. 1 | NP_418740 (AAA97216) |

An example of the type I fimbrial adhesin protein is, from *Escherichia coli*, one which has the amino acid sequence of Seq. ID No. 2 in Table 1. However, as long as its activity as a type I fimbrial adhesion protein does not change, the amino acid sequence of the type I fimbrial adhesion protein may include one or several amino acid substitutions, deletions, insertions, or additions. Here, the term "one or several" means 1 to 20, desirably 1 to 10, and preferably 1 to 5. The above amino acid substitutions, deletions, insertions, or additions are conservative mutations that maintain the production and activity of type I fimbrial adhesion protein. The term "conservative mutation" means that when the substitution is an aromatic amino acid, substitution of Phe, Trp, and Tyr for each other; when the substitution is a hydrophobic amino acid, substitution of Leu, Ile, and Val for each other; in the case of a polar amino acid, substitution of Gln and Asn for each other; in the case of a basic amino acid, substitution of Lys, Arg, and His for each other; in the case of an acidic amino acid, substitution of Asp and Glu for each other; and in the case of an amino acid having an hydroxyl group, substitution of Ser and Thr for each other. A representative conservative mutation is a conservative substitution. Substitutions that are considered to be conservative substitutions are the substitution of Ala by Ser or Thr; substitution of Asp by Asn, Glu, or Gln; substitution of Cys by Ser or Ala; substitution of Gln by Asn, Glu, Lys, His, Asp, or Arg; substitution of Glu by Asn, Gln, Lys, or Asp; substitution of Gly by Pro; substitution of His by Asn, Lys, Gln, Arg, or Tyr; substitution of Ile by Leu, Met, Val, or Phe; substitution of Leu by Ile, Met, Val, or Phe; substitution of Lys by Asn, Glu, Gln, His, or Arg; substitution of Met by Ile Leu, Val, or Phe; substitution of Phe by Trp Tyr, Met, Ile or Leu; substitution of Ser by Thr or Ala; substitution of Thr by Ser or Ala; substitution of Trp by Phe or Tyr; substitution of Tyr by His Phe, or Trp; and substitution of Val by Met, Ile, or Leu.

Since there may be some differences in DNA sequences between the genera or strains of the Enterobacteriaceae family, the gene encoding the type I fimbrial adhesin protein can be any DNA which hybridizes under stringent conditions with a probe prepared from the base sequence of SEQ. ID. No. 1 or a homologous gene of the SEQ ID No. 1 sequence. The term "stringent conditions" refers to conditions under which specific hybrids form and nonspecific hybrids do not form. By way of example, these are conditions under which highly homologous fragments of DNA, for example, DNA with a degree of homology of not less than 80%, preferably not less than 90%, and most preferably not less than 95% will hybridize. A further example is Southern blot hybridization washing conditions at a temperature and salt concentration corresponding to 60° C., 1×SSC, 0.1 percent SDS, preferably 0.1×SSC, 0.1 percent SDS, and more preferably, 68° C., 0.1×SSC, and 0.1 percent SDS, conducted one, two, or three times. The length of the probe can be suitably selected based on the hybridization conditions, but normally ranges from 100 bp to 1 Kbp.

The phrase "modified so as to not produce type I fimbrial adhesin protein" means a modification that does not destroy the fimbriae, but causes type I fimbrial adhesin protein to not function normally. Such a modification may be the introduction of a mutation into the protein with a drug or the like, weakening adhesion, or the use of genetic engineering or the introduction of a mutation into the gene relating to the formation of type I fimbrial adhesin so as to reduce the level of production of type I fimbrial adhesin protein, or breed a bacterium that does not produce type I fimbrial adhesin protein. For example, in microorganisms of the Enterobacteriaceae family that do not produce type I fimbrial adhesin protein, the transcription or translation of the gene encoding the type I fimbrial adhesin protein may be interfered with, resulting in either in the protein not being produced or being produced at a low level. A mutation may be introduced to the gene encoding the type I fimbrial adhesin protein on the chromosome and/or the region controlling expression of the gene, so that type I fimbrial adhesin proteins do not function properly. Furthermore, a mutation may be introduced into a gene encoding type I fimbrial adhesin protein as to reduce the level of expression of genes coding for type I fimbrial adhesin protein on the chromosome.

Specifically, modification so as to not produce type I fimbrial adhesin can be achieved by deleting the gene encoding type I fimbrial adhesin protein on the chromosome, or by modifying an expression regulating sequence such as a promoter or Shine-Dalgarno (SD) sequence. This can also be achieved by introducing an amino acid substitution (missense mutation) into the coding region of the type I fimbrial adhesin gene on the chromosome, introducing a stop codon (nonsense mutation), adding or deleting one or two bases to create a frame shift mutation, or partially deleting a portion, a region, or the entire gene (Journal of Biological Chemistry 272: 8611-8617 (1997), Proceedings of the National Academy of Sciences, USA 95, 5511-5515 (1998), Journal of Biological Chemistry 266, 20833-20839 (1991)).

Furthermore, modification of the fimH gene so as to not produce type I fimbrial adhesin can also be achieved by introducing the mutation into the gene in table 1 located upstream of the fimH gene.

In *Escherichia coli*, it is possible to identify the fimH gene shown in Table 1 as the chromosomal gene encoding type I fimbrial adhesin protein. To prevent the production of type I fimbrial adhesin protein, the fimH gene can be deleted or a mutation can be introduced into the region encoding fimH, as described above. This can also be achieved by introducing a mutation attenuating the expression of the fimH gene upstream from fimH; for example, a frame shift mutation or nonsense mutation can be introduced into one of the genes upstream from fimH that are indicated in Table 1, or an upstream gene can be partially deleted. More particularly, as is described further below in the embodiments, a transposon or a gene imparting resistance to an antibiotic can be incorporated in the region encoded by fimH, or the mutation described in the Journal of Bacteriology, July, 2001, 4099-4102 or the mutation described in Molecular Microbiology (2001) 41 (6), 1419-1430, can be incorporated. However, the present invention is not limited thereto.

For example, the following methods can be employed to introduce the above-described mutations by genetic recombination. The target gene on the chromosome can be replaced with a mutated gene by introducing a mutation of the sequence of the target gene, preparing a mutant form of the gene that does not produce a properly functioning enzyme, transforming a microorganism from the Enterobacteriaceae family with DNA containing the gene, and introducing the mutation of the gene to recombine with the gene on the chromosome. Such site-specific incorporation of mutations by gene substitution employing homologous recombination is already established. There exists a method employing linear DNA and a method employing a plasmid containing a temperature-sensitive replication origin (U.S. Pat. No. 6,303,383 or JP 05-007491). The introduction of a mutation at a specific site by gene substitution employing homologous recombination as set forth above can also be conducted using a plasmid which is not able to replicate on the chromosome.

Specifically, a gene encoding the type I fimbrial adhesin protein can be obtained by the following methods. Chromosomal DNA can be prepared from a microorganism belonging to the family Enterobacteriaceae, for example, by the method of Saito and Miura (see H. Saito and K. Miura, Biochem. Biophys. Acta, 72, 619 (1963); Book of Bioengineering Experiments, comp. by the Japan Bioengineering Society, p. 97-98, Baifukan, 1992). A gene encoding the type I fimbrial adhesin protein can be obtained by using a known database such as GenBank, preparing an oligonucleotide, and employing PCR. For example, it can be constructed by referring to the sequences of the genus *Escherichia* listed in Table 1.

A gene encoding the type I fimbrial adhesin protein prepared as set forth above, or a portion of such a gene, can be used for gene inactivation. However, since the gene used for gene inactivation need only have a degree of homology adequate to induce homologous recombination with the gene encoding the type I fimbrial adhesin protein on the chromosomal DNA of a microbe of the Enterobacteriaceae family, such a homologous gene may also be employed. Here, the term "degree of homology adequate to undergo homologous recombination" is desirably homology of 80% or more, preferably 90% or more, more preferably 95% or more, and particularly preferably, 97% or more. If the gene is a DNA that will hybridize with the above gene under stringent conditions, homologous recombination will occur. The term "stringent conditions" refers to conditions under which specific hybridization occurs but nonspecific hybridization does not. An example of such conditions is washing once, preferably two or three times, at a salt concentration corresponding to 60° C., 1×SSC, 0.1 percent SDS, preferably 0.1×SSC and 0.1 percent SDS.

The gene encoding type I fimbrial adhesin protein on the chromosome can be inactivated, for example, by deleting part of the sequence of the gene so it is not able to produce a properly functioning type 1 fimbrial adhesin protein, transforming a group of enterobacteria with DNA containing this gene, and causing the deficient gene to recombine with the gene on the chromosome. Such gene inactivation by gene substitution using homologous recombination is already established. There exist methods employing linear DNA such as the method developed by Datsenko and Wanner called "red-driven integration" (Proc. Natl. Acad. Sci. USA, 2000, vol. 97, No. 12, p 6640-6645), and methods employing plasmids containing temperature-sensitive replication (U.S. Pat. No. 6,303,383 or Japanese Patent Application Publication No. Hei 05-007491). Such gene destruction by gene substitution employing homologous recombination as set forth above can also be conducted using a plasmid which is not able to replicate in a host. Examples of deficient genes which have been modified so to not be able to produce type I fimbrial adhesin protein are genes from which all or a part of the region of Seq. ID No. 1 has been deleted, genes incorporating missense mutations, genes into which transposons or marker genes have been inserted, genes incorporating nonsense mutations, and genes incorporating frame shift mutations.

In addition, a method based on a combination of the method called "red-driven integration" and an excision system derived from lambda phage (J. Bacteriol. 2002 September; 184(18): 5200-3) Interactions between integrase and excisionase in the phage lambda excisive nucleoprotein complex. Cho E H, Gumport R I, Gardner J F.) can be used as the method for disrupting a gene on a chromosome (WO2005/010175).

According to the red-driven integration method, a gene-disrupted strain can be constructed in one step by using a PCR product, which is obtained using synthetic oligonucleotides as primers which are designed to include part of a targeted gene at its 5' terminus, and part of an antibiotic resistance gene at its 3' terminus. Furthermore, the integrated antibiotic resistance gene can be removed by introducing attL and attR, which are attachment sites of lambda phage, and the PCR product, and combining the excision system derived from lambda phage with the red-driven integration method.

Specifically, a strain in which the targeted gene is disrupted and the antibiotic resistance gene is removed can be obtained by the following method.

A linear DNA cassette comprising an antibiotic resistance gene, attachment sites of lambda phage and a target gene is initially prepared. This is usually prepared by PCR using a suitably-prepared template.

A template in which attL and attR (SEQ ID NO: 9 (GenBank accession No. M12458 and SEQ ID NO: 10 (GenBank accession No. M12459)) are inserted at respective terminals of an antibiotic resistance gene is used as a template of the linear DNA cassette. The template may be, for example, plasmid pMW118-attL-Tc-attR, pMW118-attL-Cm-attR (FIG. 1), a gene inserted on a chromosome, or a synthetic oligonucleotide.

While the antibiotic resistance gene is preferably a chloramphenicol resistance gene, a streptomycin resistance gene, or an ampicillin resistance gene, any antibiotic resistance gene can be used provided that the gene functions as an antibiotic resistance gene in a bacteria of the Enterobacteriaceae family and is different from a marker gene which may be contained in two helper plasmids as described below. To easily confirm the acquisition of the antibiotic resistance, the antibiotic resistance gene which is employed can be one whereby the expression is increased by replacing a promoter sequence and the like, or one in which a mutation is introduced in its structural gene sequence so that an enzyme activity is increased. The linear DNA cassette is prepared in the following order from the 5'terminus: (targeted gene 5' sequence)-(attL)-(antibiotic resistance gene)-(attR)-(targeted gene 3' sequence).

The linear DNA cassette is integrated into the chromosome. As a helper plasmid for integrating the linear DNA cassette into chromosome, pKD46 can be used (Proc. Natl. Acad. Sci. USA, 2000, 97, 6640-6645). pKD46 includes a temperature-sensitive replication origin and ampicillin resistance gene, a 2,154 nt DNA fragment of lambda phage (GenBank/EMBL accession No. J02459, 31088-33241), which contains the genes (gamma, beta, and exo genes) encoding Red recombinase of the lambda Red homologous recombination system and which is under the control of the arabinose-inducible ParaB promoter.

pKD46 can be introduced into a host by electroporation. The pKD46-amplified strain is cultured with arabinose. The linear DNA cassette is introduced at the logarithmic growth phase and incubated at a high temperature to obtain a gene-disrupted strain which is resistant to an antibiotic by the antibiotic resistance gene in the linear DNA cassette. The confirmation of the gene disruption can be made by PCR or measurement of the concentration of L-lysine or L-threonine produced by the strain.

A helper plasmid for excising the antibiotic resistance gene is then introduced. The helper plasmid harbors a gene encoding integrase (Int) (SEQ ID NO: 13, GenBank accession No. J02459. B [gi:215104]) and a gene encoding excisionase (Xis) (SEQ ID NO: 15, GenBank accession No. J02459 [gi: 215104]) of lambda phage and shows temperature-sensitive replication. By introduction of the helper plasmid, recombination occurs due to recognition of attL (SEQ ID NO: 11) and attR (SEQ ID NO: 12) on the chromosome. The antibiotic resistance gene between attL and attR is excised and as a result, a structure that contains only the attL or attR sequence remains on the chromosome. By incubating at a high temperature, the helper plasmid is lost. Thus, a strain in which the targeted gene is disrupted and the antibiotic gene is eliminated can be obtained.

In addition to the above-described gene manipulation, examples of methods of modification which preclude the production of type I fimbrial adhesin protein are subjecting a group of Enterobacteriaceae family to UV radiation or treating it with N-methyl-N'-nitro-N-nitrosoguanidine (NTG), nitrous acid, or some other mutagenic agent commonly employed in mutation treatments and selecting the strains that are unable to produce type I fimbrial adhesin protein.

<2> Method for Producing L-Amino Acids

The method for producing an L-amino acid of the present invention comprises culturing the microorganism of the present invention in a medium, causing the production and accumulation of L-amino acid in the culture or in the bacterial cell, and recovering the L-amino acid from the culture or bacterial cell. In the present invention, the cultivation, collection, and purification of an L-amino acid from the medium and the like may be performed in a manner similar to conventional fermentation methods wherein an amino acid is produced using a bacterium.

The medium employed can be one that is conventionally employed in the production of L-amino acids by fermentation. The usual medium contains a carbon source, nitrogen source, inorganic ions, and other organic components as needed. Here, exemplary carbon sources include sugar such as glucose, sucrose, lactose, galactose, fructose, or starch hydrolysis product; alcohol such as glycerol or sorbitol; and organic acids such as fumaric acid, citric acid, or succinic acid. Exemplary nitrogen sources include an inorganic ammonium salt such as ammonium sulfate, ammonium chloride, or ammonium phosphate; organic nitrogen such as a soybean hydrolysis product; ammonia gas; ammonia water; or the like. Other nutrients such as vitamin $B_1$ and L-homoserine or yeast extract can be employed in suitable quantities as a source of a trace organic nutrient. In addition, as needed, small amounts of potassium phosphate, magnesium sulfate, iron ions, manganese ions, and the like can be added. So long as the medium employed in the present invention contains a carbon source, nitrogen source, inorganic ions and, as needed, other trace organic components, it does not matter whether it is a natural or a synthetic medium.

Culturing can be conducted for 1 to 7 days under aerobic conditions at a temperature of 24 to 37° C. and at a pH of 5 to 9. Inorganic and organic acidic and alkaline substances as well as ammonia gas can be used to adjust the pH. L-amino acid can be recovered from the fermentation solution by the usual ion-exchange resin method, precipitation method, and combinations of these with other known methods. When L-amino acid accumulates within the bacterial cell, the bacterial cell can be crushed by ultrasonic waves or the like, a supernatant can be centrifugally separated from the bacterial cell, and the supernatant can be subjected to ion-exchange resin to recover the L-amino acid.

A liquid medium can be prepared under conditions which cause L-glutamic acid to precipitate, and the culture can be conducted while L-glutamic acid precipitates. An example of the conditions under which L-glutamic acid will precipitate is a pH of 5.0 to 4.0, preferably pH 4.5 to 4.0, more preferably pH 4.3 to 4.0, and particularly preferably, pH 4.0.

When culturing is conducted under conditions causing L-glutamic acid to precipitate, the L-glutamic acid precipitating out into the culture solution can be collected by centrifugation, filtration, or the like. In that case, the L-glutamic acid dissolved in the medium can be crystallized and then separated.

The present invention is further described below with reference to the following non-limiting examples.

EXAMPLES

Example 1

Construction of a Bacterium which is Modified to not Produce Type I Fimbrial Adhesin Protein <1-1> Construction of a Strain in which the Genes cadA and ldcC Encoding Lysine Decarboxylase are Destroyed First, a strain that does not produce lysine decarboxylase was constructed. Lysine decarboxylase is encoded by the cadA gene (GenBank Accession No. NP_418555, Seq. ID No. 42) and the ldcC gene (GenBank Accession No. NP_414728, Seq. ID No. 44) (see International Application Publication WO96/17930). The parent strain employed here was strain WC196. This strain was named *Escherichia coli* strain AJ13069 and was deposited on Dec. 6, 1994, as deposit number FERM P-14690, at the National Institute of Bioscience and Human-Technology, Agency of Industrial Science and Technology (currently the International Patent Organism Depositary, National Institute of Industrial Science and Technology, an Independent Administrative Institution, Central 6, 1-1-1 Higashi, Tsukuba, Ibaraki, Japan Postal Code 305-8566). This strain was converted on Sep. 29, 1995, to an international deposit under the provisions of the Budapest Treaty and given deposit number FERM BP-5252.

The genes cadA and ldcC encoding lysine decarboxylase were deleted by the method known as "Red-driven integration" developed by Datsenko and Wanner (Proc. Natl. Acad. Sci. USA, 2000, Vol. 97, No. 12, p 6640-6645) and by a λ phage-derived excision system (J. Bacteriol. 2002 September; 184 (18): 5200-3. Interactions between integrase and excisionase in the phage lambda excisive nucleoprotein complex. Cho E H, Gumport R I, Gardner J F.). (WO2005/010175) Based on the "Red-driven integration" method, a synthetic oligonucleotide designed with a part of the target gene on its 5' terminal end and a part of a antibiotic resistance gene on its 3' terminal end was employed as a primer to obtain a PCR product, which was then employed to construct a strain having an inactivated gene in a single step. By further combining this with an excision system derived from λ phage, it was possible to remove from the gene-inactivated strain the integrated antibiotic resistance gene.

(1) Disruption of the cadA Gene

A plasmid pMW118-attL-Cm-attR was employed as PCR template. pMW118-attL-Cm-attR was a plasmid obtained by inserting the attL and attR genes—attachment sites of λ phage—and the cat gene, a gene imparting antibiotic-resistance, into pMW118 (Takara-Bio Co.) in the order attL-cat-attR. The sequence of attL is shown by SEQ. ID No. 11 and the sequence of attR by SEQ. ID No.12.

A synthetic oligonucleotide with Seq. ID Nos. 3 and 4 on its 5' terminal, corresponding to a part of the cadA gene, and sequences corresponding to the both ends of attL and attR on its 3'terminal, was employed as a primer to conduct PCR.

The amplified PCR product was purified on an agarose gel and introduced by electroporation into *Escherichia coli* strain WC196, which contains plasmid pKD46 with a temperature-sensitive replication origin. Plasmid pKD46 (Proc. Natl. Acad. Sci. USA, 2000, Vol. 97, No. 12, p 6640-6645) includes a DNA fragment (GenBank/EMBL Accession No. J02459, Nos. 31088 to 33241) having a total of 2,154 bases of λ-phage containing genes (γ, β, and exo genes) encoding the Red recombinase of the λ Red homologous recombination system controlled by an arabinose-derived $P_{araB}$ promoter. Plasmid pKD46 was required to introduce the PCR product into the chromosome of strain WC196.

Competent cells for electroporation were prepared as follows. The *Escherichia coli* strain WC196 that had been cultured overnight at 30° C. in LB medium containing 100 mg/L of ampicillin was diluted 100-fold with 5 mL of SOB medium (Molecular Cloning: Laboratory Manual, 2$^{nd}$ Ed., Sambrook J. et al., Cold Spring Harbor Laboratory Press (1989)) containing L-arabinose (1 mM) and ampicillin (20 mg/L). The diluted product was cultured until reaching an OD600 of about 0.6 at 30° C., concentrated 100-fold, and readied for electroporation by washing three times in 10 percent glycerol. Electroporation was conducted using 70 μL of competent cells and about 100 ng of the PCR product. Following electroporation, 1 mL of SOC medium (Molecular Cloning: Laboratory Manual, 2$^{nd}$ Ed., Sambrook J. et al., Cold Spring Harbor Laboratory Press (1989)) was added and the cells were cultured for 2.5 hours at 37° C. They were then plate cultured on L-agar medium containing chloramphenicol (Cm, 25 mg/L) at 37° C. and the Cm-resistant recombinants were selected. Next, to remove the pKD46 plasmid, cell were subcultured at 42° C. on Cm-containing L-agar medium and the ampicillin resistance of the colonies obtained was tested. The ampicillin-sensitive strains without pKD46 were collected.

The deletion of the cadA gene in mutants identified based on chloramphenicol resistance gene was confirmed by PCR. The cadA-deficient strain obtained was named strain WC196ΔcadA::att-cat.

The above-described helper plasmid pMW-intxis-ts was employed to remove the att-cat genes that were inserted inside the cadA gene. pMW-intxis-ts is a plasmid which harbors a gene (SEQ. ID No. 13) encoding the integrase (Int) of the λ phage and a gene (SEQ. ID No. 15) encoding the excisionase (Xis) of the λ phage, and which has a temperature-sensitive replication origin. By introducing pMW-intxis-ts, recombination occurs due to the recognition of attL (SEQ. ID No. 11) and attR (SEQ. ID No. 12) on the chromosome, allowing gene excision between attL and attR, leaving behind only the attL or attR sequence on the chromosome.

Competent cells of the strain WC196ΔcadA::att-cat obtained as set forth above were prepared by ordinary methods, transformed with helper plasmid pMW-intxis-ts, and plate cultured on L-agar medium containing 50 mg/L of ampicillin at 30° C. The ampicillin-resistant strains were selected.

Next, to remove the pMW-intxis-ts plasmid, cells were subcultured at 42° C. on L agar medium. The ampicillin resistance and chloramphenicol resistance of the colonies obtained were tested and a strain sensitive to chloramphenicol and ampicillin, which was a cadA-deleted strain which had removed the att-cat and pMW-intxis-ts, was collected. This strain was named WC196ΔcadA.

(2) Strain WC196ΔcadA and Deletion of the ldcC Gene

Deletion of the ldcC gene in strain WC196ΔcadA was conducted using primers with SEQ. ID NO. 5 and 6 to destroy the ldcC by the above-described method. This resulted in a strain in which cadA and ldcC had been deleted, and was designated WC196ΔcadAΔldcC.

(3) Preparation of PCR Template and Helper Plasmid

PCR template pMW118-attL-Cm-attR and helper plasmid pMW-intxis-ts were prepared as set forth below.

(3-1) pMW118-attL-Cm-attR pMW118-attL-Cm-attR was constructed based on pMW118-attL-Tc-attR. The four following DNA fragments were spliced.

1) BglII-EcoRI DNA fragment (120 bp) (SEQ. ID No. 11) containing attL obtained by PCR amplification of a sequence corresponding to the chromosome of *E. coli* strain W3350 (ATCC 31278 containing λ prophage) using primers in the form of oligonucleotides P1 and P2 (SEQ. ID NO. 17 and 18) (these primers contained additional BglII and EcoRI endonuclease recognition sites).

2) PstI-HindIII DNA fragment (182 bp) (SEQ. ID No. 12) containing attR obtained by PCR amplification of a sequence corresponding to the chromosome of *E. coli* strain W3350 (containing λ prophage) using primers in the form of oligonucleotides P3 and P4 (SEQ. ID Nos. 19 and 20) (these primers contained additional PstI and HindIII endonuclease recognition sites).

3) BglII-HindIII large fragment (3,916 bp) of pMW118-ter_rrnB. pMW118-ter_rrn was a fragment obtained by ligation of the following three fragments:

A large fragment (2,359 bp) containing an AatII-EcoRIpol fragment of pMW118 was obtained by cleaving pMW118 with EcoRI restriction endonuclease, processing with the Klenow fragment of DNA polymerase I, and digesting with AatII restriction endonuclease, AatII-BglII small fragment (1194 bp) of pUC19 containing the bla gene of ampicillin resistance (ApR), obtained by employing oligonucleotides P5 and P6 (SEQ. ID Nos. 21 and 22) as primers (these primers contained additional AatII and BglII endonuclease recognition sites) in PCR amplification of the sequence corresponding to the pUC19 plasmid, BglII-PstIpol small fragment (363 bp) of transcription terminator_rrnB obtained by employing oligonucleotides P7 and P8 (SEQ. ID Nos. 23 and 24) as primers (these primers had additional BglII and PstI endonuclease identification sites) in PCR amplification of the region corresponding to the chromosome of *E. coli* strain MG1655.

4) Small EcoRI-PstI fragment (1,388 bp) (SEQ. ID No. 29) of pML-Tc-ter_thrL comprising a tetracycline resistance gene and transcription terminator ter_thrL. pML-Tc-ter-thrL was obtained as follows.

pML-MCS (Mol Biol (Mosk). 2005 September-October; 39(5):823-31 Biotechnologiya (Russian) No. 5: 3-20) was digested with XbaI and BamHI restriction endonucleases and the large fragment (3342 bp) was spliced to an XbaI-BamHI fragment (68 bp) containing terminator ter_thrL. The region of the XbaI-BamHI fragment corresponding to the chromosome of *E. coli* strain MG1655 was amplified by PCR using oligonucleotides P9 and P10 (SEQ. ID Nos. 25 and 26) as primers (these primers contained additional XbaI and BamHI endonuclease recognition sites). The ligated reaction product was named plasmid pML-ter_thrL.

pML-ter_thrL was cleaved with KpnI and XbaI restriction endonucleases, treated with the Klenow fragment of DNA polymerase I, and then ligated to the small EcoRI-Van91I fragment (1,317 bp) of pBR322 containing a tetracycline resistance gene (pBR322 was treated with the Klenow fragment of DNA polymerase I using EcoRI and Van91I restriction endonucleases). The product of the ligation reaction was named plasmid pML-Tc-ter_thrL.

pMW118-attL-Tc-attR was obtained as set forth above.

pMW118-attL-Cm-attR was constructed by ligation the large BamHI-XbaI fragment (4,413 bp) of pMW118-attL-Tc-attR, promoter P$_{42}$ (the initial promoter of T7 phage), the cat gene of chloramphenicol resistance (Cm$^R$), and BglII-XbaI artificial DNA fragment (1,162 bp) comprising the transcription terminator ter_thrL and attR. The artificial DNA fragment (SEQ. ID No. 30) was obtained as follows.

The pML-MSC (Mol Biol (Mosk). 2005 September-October; 39(5):823-31; Biotechnologiya (Russian) No. 5: 3-20.)) was cleaved with KpnI and XbaI restriction endonucleases and ligated to the small KpnI-XbaI fragment (120 bp) containing promoter $P_{A2}$ (the initial promoter of T7 phage). The KpnI-XbaI fragment was obtained by PCR amplification of the region corresponding to T7 phage DNA using oligonucleotides P11 and P12 (SEQ. ID Nos. 27 and 28) as primers (these primers had additional KpnI and XbaI endonuclease recognition sites). The product of the splicing reaction was named plasmid pML-PA2-MCS.

The XbaI site was removed from pML-PA2-MCS. The product obtained was called plasmid pML-PA2-MCS (XbaI-).

The small BglII-HindIII fragment (928 bp) of pML-$P_{A2}$-MCS(XbaI-) containing promoter PA2 (the initial promoter of T7 phage) and the cat gene imparting resistance to chloramphenicol (CmR) was ligated to the small HindIII-HindIII fragment (234 bp) of pMW118-attL-Tc-attR containing transcription terminator ter_thrL and attR.

The targeted artificial DNA fragment (1,156 bp) was obtained by PCR amplification of the splicing reaction mixture with primers in the form of oligonucleotides P9 and P4 (SEQ. ID Nos. 25 and 20) (these primers contained additional HindIII and XbaI endonuclease recognition sites).

(3-2) pMW-intxis-ts

Initially, two DNA fragments were amplified using λ phage DNA (Fermentas) as template. The first fragment was comprised of nt 37168 to 38046 (SEQ. ID No. 39), containing CI repressor, promoters Prm and Pr, and the leader sequence of the cro gene. This fragment was obtained by amplification using oligonucleotides P1' and P2' (SEQ. ID NO. 31 and 32) as primers. The second fragment was comprised of nt 27801 to 29100 (SEQ. ID NO. 40), containing the xis-int genes of λ phage. This fragment was obtained by amplification using oligonucleotides P3' and P4' (SEQ. ID NO. 33 and 34) as primers. All the primers include suitable endonuclease recognition sites.

The PCR amplification fragment containing cI repressor that was obtained was cleaved with ClaI restriction endonuclease, treated with the Klenow fragment of DNA polymerase I, and digested with EcoRI restriction endonuclease. The second PCR amplified fragment was digested with EcoRI and PstI restriction endonucleases. Additionally, plasmid pMW-PlaclacI-ts was digested with BglII endonuclease, treated with the Klenow fragment of DNA polymerase I, and cleaved with PstI restriction endonuclease. The vector fragment of pMWPladlacI-ts was eluted from agarose gel and ligated to the cut PCR amplified fragment. (Biotechnologiya (Russian) No. 5: 3-20.)

Plasmid pMWPlaclacI-ts was derived from pMWPlaclacI, which comprised the following components: 1) a BglII-HindIII artificial DNA fragment comprising PlacUV5 promoter and the lacI gene controlled by the RBS of bacteriophage T7 gene 10; 2) an AatII-BglII fragment containing an ampicillin resistance (ApR) gene, obtained by PCR amplification of the region corresponding to plasmid pUC19 using oligonucleotides P5' and P6' (SEQ. ID Nos. 35 and 36) as primers (these primers contained additional AatII and BglII endonuclease recognition sites); 3) an AatII-BglII fragment containing the AatII-PvuI fragment of recombinant plasmid pMW118-ter_rrnB. Plasmid pMW118-ter_rrnB was constructed in the following manner. The region corresponding to the chromosome of E. coli strain MG1655 was amplified by PCR using oligonucleotides P7' and P8' (SEQ. ID Nos. 37 and 38) containing suitable endonuclease recognition sites as primers, yielding a PstI-HindIII fragment containing terminator ter_rrnB. Before ligation, the pMW118 and the ter_rrnB fragment (complement; SEQ. ID No. 41) were restricted with PvuI and PstI, respectively, treated with the Klenow fragment of DNA polymerase to blunt the ends, and digested with AatII or HindIII endonuclease. To construct a pMWPlaclacI-ts mutant, the AatII-EcoRV fragment of the plasmid pMWPlaclacI was replaced with the AatII-EcoRV fragment of plasmid pMAN997 containing the par, ori, and repAts genes of the pSC101 replicon. (Applied and Environmental Microbiology, June 2005, p. 3228-32)

<1-2> Construction of a Strain which does not Produce type I Fimbrial Adhesin Protein (Strain Deleting the fimH Gene: WC196ΔcadAΔldcCΔfimH Strain) from WC196ΔcadAΔldcC The fimH gene was deleted from the WC196ΔcadAΔldcC strain by the procedure of (1) above; the primers of SEQ. ID Nos. 7 and 8 were employed to delete the fimH gene. This obtained strain did not produce type I fimbrial adhesion protein, and was designated WC196ΔcadAΔldcCΔfimH::Cm.

Strains WC196ΔcadAΔldcC and WC196ΔcadAΔldcCΔfimH::Cm were transformed by the usual methods with plasmid Lys production-plasmid pCABD2 carring dapA, dapB, and LysC genes (WO01/53459), obtaining strains WC196ΔcadAΔldcC/pCABD2 and WC196ΔcadAΔldcCΔfimH::Cm/pCABD2. These strains were cultured at 37° C. in L medium containing 20 mg/L of streptomycin to a final OD600 of about 0.6. A 40 percent glycerol solution was added in a quantity equal to that of the culture solution, the mixture was stirred, and suitable amouts were poured out and stored at –80° C. This was referred to as glycerol stock.

Example 2

Evaluation of the L-Lysine Production of a Strain which does not Produce Type I Fimbrial Adhesin Protein The glycerol stocks of these strains were melted, 100 μL amounts were uniformly plated onto L plates containing 20 mg/L of streptomycin, and the strain were cultured for 24 hours at 37° C. About ⅛ of the bacterial cells obtained on each plate was inoculated onto a 20 mL fermentation culture containing 20 mg/L of streptomycin in a 500 mL Sakaguchi flask and cultured for 48 hours at 37° C. in a reciprocating shaking incubator. After culturing, the amount of L-lysine that had accumulated in the medium was measured by a ordinary method (Sakura Seiki, Biotech Analyzer AS210).

The composition of the fermentation medium is shown below (unit: g/L).

| | |
|---|---|
| Glucose | 40 |
| $(NH_4)_2SO_4$ | 24 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 |
| | Up to 1 L |

The medium was adjusted to pH 7.0 with KOH and sterilized for 10 min at 115° C. in an autoclave (the glucose and $MgSO_4.7H_2O$ were separately sterilized). A 30 g/L quantity of $CaCO_3$ (that had been dry sterilized for 2 hours at 180° C.) was added.

20 mg/L amounts of streptomycin was added as antibiotic. Culturing was conducted for 48 hours under conditions of a temperature of 37° C. with stirring at 115 rpm.

The results are given in Table 2 (OD is the absorbance at 600 nm by the bacterial mass diluted 26-fold, Lys (g/L) is the amount of L-lysine accumulated in the flask, and the yield (%) is the L-lysine yield from sugar). As will be shown in Table 2, strain WC196ΔcadAΔldcCΔfimH::Cm/pCABD2 accumulated more L-lysine than strain WC196ΔcadAΔldcC::Cm/pCABD2, from which the fimH gene had not been deleted.

TABLE 2

|  | OD (×26) | Lys (g/L) | Yield (%) |
| --- | --- | --- | --- |
| WC196ΔcadAΔldcC/pCABD2 | 0.712 | 17.54 | 42.21 |
| WC196ΔcadAΔldcCΔfimH/pCABD2 | 0.710 | 18.19 | 43.77 |

Example 3

Evaluation of the L-Threonine Production of a Strain which does not Produce type I Fimbrial Adhesin Protein B-5318 was employed as the L-threonine-producing parent strain which does not produce type I fimbrial adhesin protein. Strain B-5318 was deposited on Nov. 19, 1987, under registration number VKPM B-5318 with the Russian National Collection of Industrial Microorganisms (VKPM), GNII Genetika. The strain which does not produce type I fimbrial adhesin was constructed from the L-threonine producing bacterium by the same method as in Example 1 by employing synthetic oligonucleotides SEQ. ID Nos. 7 and 8. Specifically, the following fimH deficient strain was constructed. B-5318ΔfimH-cat was derived from strain B-5318 by method (1) in Example 1. Strain B-5318 and strain B-5318ΔfimH-cat were cultured for 24 hours at 37° C. on L agar medium containing 20 mg/L of streptomycin sulfate and L agar medium containing 20 mg/L of streptomycin sulfate and 25 mg/L of chloramphenicol, respectively. One-fifth of the bacterial cell was collected from each of the plates and inoculated onto 50 mL of LB liquid medium containing the above-stated antibiotics and the bacteria were precultured for 3.5 hours at a temperature of 39° C. at 144 rpm.

Following preculturing, a quantity of preculture solution amounting to 10 percent of the volume of the main culture medium was inoculated into a one-liter jar fermenter containing 300 mL of main culture medium and the main culture was cultivated at 40° C. at pH 7.0. The composition of the main culture medium is shown below.

| Composition of Main Culture Medium | |
| --- | --- |
| Glucose | 100 g/L |
| Yeast extract | 1.8 g/L |
| $FeSO_4 \cdot 7H_2O$ | 18 mg/L |
| $MnSO_4 \cdot 4H_2O$ | 18 mg/L |
| $KH_2PO_4$ | 1 g/L |
| $MgSO_4 \cdot 7H_2O$ | 0.36 g/L |
| $(NH_4)_2SO_4$ | 4.5 g/L |
| NaCl | 0.6 g/L |

For strain B5318, 20 mg/L of streptomycin sulfate salt was added, and for strain B-5318ΔfimH-cat, 20 mg/L of streptomycin sulfate salt and 25 mg/L of chloramphenicol were added.

Ammonia gas was added to adjust the culture to pH 7.0. When the glucose was exhausted, culturing was stopped and liquid chromatography was employed to measure the quantity of L-threonine. The results are shown in Table 3. OD is the absorbance at 600 nm by the bacterial mass diluted 101-fold, Thr (g/L) is the amount of L-threonine which had accumulated in the flask, and the yield (%) is the L-threonine yield from sugar.

Use of the B-5318ΔfimH-cat strain, which lacked the fimH gene, enhanced the yield of L-threonine compared with the B-5318 strain, which served as a control.

TABLE 3

| Strain | OD (×101) | Thr (g/L) | Yield (%) |
| --- | --- | --- | --- |
| B-5318 | 0.597 | 32.7 | 32.9 |
| B-5318Δfim-cat | 0.617 | 34.4 | 33.4 |

Example 4

Evaluation of the L-Glutamic Acid Production of a Strain which does not Produce type I Fimbrial Adhesin Protein <4-1> Evaluation of the L-Glutamic Acid Production of a *Escherichia coli* Strain which does not Produce type I Fimbrial Adhesin Protein

*Escherichia coli* strain AJ12949 was employed as the L-glutamic acid-producing parent strain which does not produce type I fimbrial adhesin protein. Strain AJ12949 was deposited on Dec. 28, 1993, as depositary number FERM P-14039, at the National Institute of Bioscience and Human-Technology, Agency of Industrial Science and Technology (currently the International Patent Organism Depositary, National Institute of Industrial Science and Technology, an Independent Administrative Institution, Central 6, 1-1-1 Higashi, Tsukuba, Ibaraki, Japan Postal Code 305-8566), and converted on Nov. 11, 1994, to an international deposit under the provisions of the the Budapest Treaty, and given a deposit number FERM BP-4881.

Culturing was conducted in the following specific manner. Strain AJ12949ΔfimH-cat was derived from strain AJ12949 (BP-4881). Strain AJ12949 and strain AJ12949ΔfimH-cat were cultured for 24 hours at 37° C. in L agar medium containing 50 mg/L of ampicillin and L agar solution containing 50 mg/L of ampicillin and 25 mg/L of chloramphenicol, respectively. One-eighth of the bacterial cells was collected from each plate and inoculated onto 20 mL of fermentation medium containing 50 mg/L of ampicillin in a 500 mL Sakaguchi flask and cultured for 24 hours at 37° C. in a reciprocating shaking incubator. Following culturing, the amount of glutamic acid accumulated in the medium was measured by a known method (Sakura Seiki, Biodex Analyzer AS210).

| The composition of the fermentation medium is given below (unit: g/L) | |
| --- | --- |
| Glucose | 40 |
| Yeast extract | 2 |
| $FeSO_4 \cdot 7H_2O$ | 0.01 |
| $MnSO_4 \cdot 4H_2O$ | 0.01 |
| $KH_2PO_4$ | 1 |
| $MgSO_4 \cdot 7H_2O$ | 1 |
| $(NH_4)_2SO_4$ | 20 |
| Thiamine hydrochloride | 0.01 |

The medium was adjusted to pH 7.0 with KOH and sterilized for 10 min at 115° C. in an autoclave (the glucose and $MgSO_4 \cdot 7H_2O$ were separately sterilized). A 50 g/L quantity of $CaCO_3$ (that had been dry sterilized for 2 hours at 180° C.) was added.

A 50 mg/L quantity of ampicillin was added as an antibiotic for strain AJ12949, and a 50 mg/L quantity of ampicillin and a 50 mg/L quantity of chloramphenicol were added for AJ12949ΔfimH-cat.

The results are given in Table 4 (OD is the absorbance at 600 nm by the bacterial mass diluted 26-fold, Glu (g/L) is the amount of L-glutamine accumulated in the flask, and the yield (%) is the L-glutamic acid yield from sugar). Strain AJ12949ΔfimH-cat, the strain that did not produce type I fimbrial adhesin protein, accumulated more L-glutamic acid than strain AJ12949, from which fimH was not deleted.

TABLE 4

| Strain | OD (×26) | Glu (g/L) | Yield (%) |
|---|---|---|---|
| AJ12949 | 0.698 | 20.50 | 51.25 |
| AJ12949Δfim::Cm | 0.762 | 21.36 | 53.41 |

<4-2> Evaluation of the L-Glutamic Acid Production of a *Pantoea ananatis* Strain which does not Produce Type I Fimbrial Adhesin Protein

*Pantoea ananatis* strain AJ13601 can also be employed as the L-glutamic acid-producing parent strain which does not produce type I fimbrial adhesin protein. *Pantoea ananatis* strain AJ13601 was deposited on Aug. 18, 1999, as depositary number FERM P-17516, at the National Institute of Bioscience and Human-Technology, Agency of Industrial Science and Technology, Ministry of Economy, Trade and Industry (1-1-3 Higashi, Tsukuba, Ibaraki Prefecture, Postal Code 305-8566). This strain was converted on Jul. 6, 2000, to a deposit under the provisions of the Budapest Treaty under deposit number FERM BP-7207. A strain that does not produce type I fimbrial adhesin can be constructed from the L-glutamic acid-producing microbe by the same method as in Example 1 using synthetic nucleotides having SEQ. ID Nos. 7 and 8. A mutant strain can also be constructed by introducing a temperature-sensitive plasmid having a deleted gene encoding type I fimbrial adhesin protein.

The strain not producing type I fimbrial adhesin protein can be cultured in an L-glutamic acid production medium in a reciprocating shaking incubator. Following culturing, the amount of L-glutamic acid which had accumulated in the medium is measured by a ordinary method to confirm an increase in accumulated L-glutamic acid. This method permits the obtaining of a strain that does not produce type I fimbrial adhesin protein and has an enhanced ability to produce L-glutamic acid.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

We claim:

1. A method for producing an L-amino acid, comprising cultivating an *Escherichia coli* in a medium, and collecting said L-amino acid from the medium, wherein the fimH gene of said *Escherichia coli* has been inactivated by a method selected from the group consisting of A) deleting the fimH gene,
B) modifying a promoter or a Shine-Dalgarno sequence of-the fimH gene,
C) introducing a missense mutation into the fimH gene,
D) introducing a nonsense mutation into the fimH gene, and
E) introducing a frame shift mutation into the fimH gene and wherein said fimH gene is selected from the group consisting of:
   (a) a DNA comprising the nucleotide sequence of SEQ ID NO:1, and
   (b) a DNA that is able to hybridize with the complementary strand of the nucleotide of SEQ ID NO:1 under conditions comprising washing at 60° C. and at a salt concentration corresponding to 1×SSC, 0.1 ×SDS, and wherein the DNA encodes fimH.

2. The method according to claim 1, wherein said L-amino acid is selected from the group consisting of L-lysine, L-threonine, L-glutamie acid, and combinations thereof.

* * * * *